US012708302B2

(12) United States Patent
McKinney et al.

(10) Patent No.: US 12,708,302 B2
(45) **Date of Patent: *Aug. 18, 2026**

(54) CATHETER FOR MONITORING PRESSURE

(71) Applicant: Sentinel Medical Technologies, LLC, Boca Raton, FL (US)

(72) Inventors: Timothy McKinney, Boca Raton, FL (US); Marc-Alan Levine, Pottstown, PA (US); Michael Leedle, Audobon, PA (US)

(73) Assignee: Sentinel Medical Technologies, LLC, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/640,067

(22) Filed: Apr. 19, 2024

(65) Prior Publication Data

US 2024/0260873 A1 Aug. 8, 2024

Related U.S. Application Data

(60) Continuation of application No. 18/127,804, filed on Mar. 29, 2023, now Pat. No. 11,969,248, which is a (Continued)

(51) Int. Cl.
*A61B 5/20* (2006.01)
*A61B 5/00* (2006.01)
(Continued)

(52) U.S. Cl.
CPC .............. *A61B 5/205* (2013.01); *A61B 5/036* (2013.01); *A61B 5/6853* (2013.01); (Continued)

(58) Field of Classification Search
None
See application file for complete search history.

(56) References Cited

U.S. PATENT DOCUMENTS 3,721,229 A 3/1973 Panzer
3,866,599 A 2/1975 Johnson
(Continued)

FOREIGN PATENT DOCUMENTS

CA 2961757 3/2016
CN 201267504 7/2009
(Continued)

OTHER PUBLICATIONS

US 11,433,217 B2, 09/2022, Erbey, II et al. (withdrawn)
(Continued)

*Primary Examiner* — Benjamin S Melhus
(74) *Attorney, Agent, or Firm* — Neil D. Gershon

(57) ABSTRACT

A catheter insertable into a patient for monitoring pressure having an expandable outer balloon. An expandable inner balloon is positioned within the lumen of the catheter and has having a second outer wall and forms a gas chamber to monitor pressure within the patient. In response to pressure exerted on the outer wall of the outer balloon, fluid within the outer balloon enters an opening in the wall of the catheter lumen to exert a pressure on the outer wall of the expanded inner balloon to deform the inner balloon and compress the gas within the inner balloon. A pressure sensor communicates with the gas containing chamber for measuring pressure based on compression of gas caused by deformation of the expanded inner balloon resulting from deformation of the expanded outer balloon.

17 Claims, 80 Drawing Sheets

Related U.S. Application Data division of application No. 16/675,358, filed on Nov. 6, 2019, now Pat. No. 11,672,457.

(60) Provisional application No. 62/865,360, filed on Jun. 24, 2019, provisional application No. 62/771,040, filed on Nov. 24, 2018.

(51) Int. Cl.

| | |
|---|---|
| ***A61B 5/03*** | (2006.01) |
| ***A61M 25/00*** | (2006.01) |
| ***A61M 25/10*** | (2013.01) |
| ***A61M 27/00*** | (2006.01) |

(52) U.S. Cl.

CPC ........ *A61M 25/0071* (2013.01); *A61M 27/00* (2013.01); *A61M 2025/0002* (2013.01); *A61M 2025/0003* (2013.01); *A61M 25/1011* (2013.01); *A61M 2025/1068* (2013.01)

(56) References Cited

U.S. PATENT DOCUMENTS

| | | | |
|---|---|---|---|
| 4,192,319 | A | 3/1980 | Hargens et al. |
| 4,335,723 | A | 6/1982 | Patel |
| 4,600,015 | A | 7/1986 | Evans et al. |
| 4,739,769 | A | 4/1988 | Mathews et al. |
| 4,873,986 | A | 10/1989 | Wallace |
| 4,901,731 | A | 2/1990 | Millar |
| 4,924,877 | A | 5/1990 | Brooks |
| 4,976,692 | A | 12/1990 | Atad |
| 5,135,002 | A | 8/1992 | Kirchner et al. |
| 5,167,237 | A | 12/1992 | Rabin et al. |
| 5,171,299 | A | 12/1992 | Heitzmann et al. |
| 5,389,217 | A | 2/1995 | Singer |
| 5,398,692 | A | 3/1995 | Hickey |
| 5,417,207 | A | 5/1995 | Young et al. |
| 5,431,629 | A | 7/1995 | Lampropoulos et al. |
| 5,433,216 | A | 7/1995 | Sugrue et al. |
| 5,447,497 | A | 9/1995 | Sogard et al. |
| 5,551,439 | A | 9/1996 | Hickey |
| 5,566,680 | A | 10/1996 | Urion |
| 5,570,671 | A | 11/1996 | Hickey |
| 5,573,007 | A | 11/1996 | Bobo, Sr. |
| 5,623,940 | A | 4/1997 | Daikuzono |
| 5,697,375 | A | 12/1997 | Hickey |
| 5,707,358 | A | 1/1998 | Wright |
| 5,715,816 | A | 2/1998 | Mainiero et al. |
| 5,902,248 | A | 5/1999 | Millar et al. |
| 5,916,153 | A | 6/1999 | Rhea, Jr. |
| 5,928,155 | A | 7/1999 | Eggers et al. |
| 5,951,497 | A | 9/1999 | Wallace et al. |
| 5,980,485 | A | 11/1999 | Grantz et al. |
| 5,984,879 | A | 11/1999 | Wallace et al. |
| 6,021,781 | A | 2/2000 | Thompson et al. |
| 6,115,624 | A | 9/2000 | Lewis |
| 6,167,886 | B1 | 1/2001 | Engel |
| 6,183,421 | B1 | 2/2001 | Bobo |
| 6,231,524 | B1 | 5/2001 | Wallace et al. |
| 6,248,083 | B1 | 6/2001 | Smith |
| 6,434,418 | B1 | 8/2002 | Neal et al. |
| 6,447,462 | B1 | 9/2002 | Wallace et al. |
| 6,450,971 | B1 | 9/2002 | Andrus et al. |
| 6,461,332 | B1 | 10/2002 | Mosel et al. |
| 6,585,660 | B2 | 7/2003 | Dorando |
| 6,602,243 | B2 | 8/2003 | Noda |
| 6,616,597 | B2 | 9/2003 | Schock et al. |
| 6,648,879 | B2 | 11/2003 | Joye et al. |
| 6,673,022 | B1 | 1/2004 | Bobo et al. |
| 6,689,089 | B1 | 2/2004 | Tiedtke et al. |
| 6,723,053 | B2 | 4/2004 | Ackerman et al. |
| 6,819,951 | B2 | 11/2004 | Patel et al. |
| 6,827,710 | B1 | 12/2004 | Mooney et al. |
| 6,890,307 | B2 | 5/2005 | Kokate et al. |
| 6,935,999 | B2 | 8/2005 | Schock et al. |
| 7,081,096 | B2 | 7/2006 | Brister et al. |
| 7,112,170 | B2 | 9/2006 | Schock et al. |
| 7,229,403 | B2 | 6/2007 | Schock et al. |
| 7,347,822 | B2 | 3/2008 | Brockway et al. |
| 7,381,190 | B2 | 6/2008 | Sugrue et al. |
| 7,654,967 | B2 | 2/2010 | Bobo, Sr. |
| 7,722,544 | B2 | 5/2010 | Williams et al. |
| 7,828,753 | B2 | 11/2010 | Euliano, II et al. |
| 7,959,579 | B2 | 6/2011 | Dijkman |
| 7,976,475 | B2 | 7/2011 | Dijkman |
| 8,007,444 | B2 | 8/2011 | Kokate et al. |
| 8,025,623 | B1 | 9/2011 | Millar |
| 8,192,368 | B2 | 6/2012 | Woodruff et al. |
| 8,235,426 | B2 | 8/2012 | Pisula, Jr. et al. |
| 8,337,411 | B2 | 12/2012 | Nishtala et al. |
| 8,360,988 | B2 | 1/2013 | Bobo, Sr. et al. |
| 8,360,989 | B2 | 1/2013 | de Menezes |
| 8,403,884 | B2 | 3/2013 | Nishtala |
| 8,447,783 | B2 | 5/2013 | Goping |
| 8,491,503 | B2 | 7/2013 | Zaiken et al. |
| 8,535,237 | B2 | 9/2013 | Nishtala |
| 8,596,688 | B2 | 12/2013 | Pisula, Jr. et al. |
| 8,626,316 | B2 | 1/2014 | Mohl |
| 8,636,724 | B2 | 1/2014 | Wiita et al. |
| 8,636,728 | B2 | 1/2014 | Watson |
| 8,646,325 | B2 | 2/2014 | Hoem et al. |
| 8,708,927 | B2 | 4/2014 | Dijkman |
| 8,876,729 | B2 | 11/2014 | Bobo, Sr. et al. |
| 9,046,205 | B2 | 6/2015 | Whitaker et al. |
| 9,055,949 | B2 | 6/2015 | Belfort |
| 9,101,314 | B2 | 8/2015 | Shi |
| 9,107,695 | B2 | 8/2015 | Horton et al. |
| 9,108,000 | B2 | 8/2015 | Kassab |
| 9,126,008 | B2 | 9/2015 | Kim |
| 9,131,898 | B2 | 9/2015 | O'Dea et al. |
| 9,167,973 | B2 | 10/2015 | Steiner et al. |
| 9,278,202 | B2 | 3/2016 | Ranade |
| 9,393,353 | B2 | 7/2016 | Alam et al. |
| 9,439,600 | B2 | 9/2016 | Mohl |
| 9,440,043 | B2 | 9/2016 | Arora et al. |
| 9,510,766 | B2 | 12/2016 | Weed et al. |
| 9,511,209 | B2 | 12/2016 | Drasler et al. |
| 9,534,721 | B2 | 1/2017 | Lombardi, III |
| 9,597,140 | B2 | 3/2017 | Mihalik |
| 9,622,670 | B2 | 4/2017 | Burnett et al. |
| 9,623,201 | B2 | 4/2017 | Gregory et al. |
| 9,655,555 | B2 | 5/2017 | Burnett et al. |
| 9,662,058 | B2 | 5/2017 | Burnett et al. |
| 9,695,966 | B2 | 7/2017 | Lombardi, III et al. |
| 9,713,494 | B2 | 7/2017 | Nabutovsky et al. |
| 9,717,472 | B2 | 8/2017 | Ahmed et al. |
| 9,724,232 | B2 | 8/2017 | Kassab et al. |
| 9,734,706 | B2 | 8/2017 | Moon et al. |
| 9,757,545 | B2 | 9/2017 | Kassab |
| 9,782,115 | B2 | 10/2017 | Shi |
| 9,782,145 | B2 | 10/2017 | Hart et al. |
| 9,848,790 | B2 | 12/2017 | Pintel |
| 9,849,234 | B2 | 12/2017 | Baykal |
| 9,877,660 | B2 | 1/2018 | O'Connell et al. |
| 9,895,103 | B2 | 2/2018 | Hyde et al. |
| 9,913,585 | B2 | 3/2018 | McCaffrey et al. |
| 9,931,044 | B2 | 4/2018 | Burnett et al. |
| 9,931,122 | B2 | 4/2018 | Burnett et al. |
| 9,943,352 | B2 | 4/2018 | Mihalik |
| 10,004,551 | B2 | 6/2018 | Burnett |
| 10,194,813 | B2 | 2/2019 | Bharucha et al. |
| 10,206,575 | B2 | 2/2019 | Al-Mayah |
| 10,238,307 | B2 | 3/2019 | Schlumpf et al. |
| 10,314,488 | B2 | 6/2019 | Samuelsson et al. |
| 10,368,872 | B2 | 8/2019 | Franklin et al. |
| 10,376,679 | B2 | 8/2019 | Cox et al. |
| 10,391,275 | B2 | 8/2019 | Burnett et al. |
| 10,426,919 | B2 | 10/2019 | Erbey, II et al. |
| 10,433,741 | B2 | 10/2019 | Stimpson |
| 10,478,113 | B2 | 11/2019 | Damaser et al. |
| 10,485,483 | B1 | 11/2019 | Brody |
| 10,512,754 | B2 | 12/2019 | Sliwa et al. |
| 10,517,538 | B2 | 12/2019 | Burnett et al. |
| 10,531,834 | B1 | 1/2020 | Smith et al. |

(56) References Cited

U.S. PATENT DOCUMENTS

| | | | |
|---|---|---|---|
| 10,532,193 | B2 | 1/2020 | Fischer, Jr. et al. |
| 10,537,274 | B2 | 1/2020 | Damaser et al. |
| 10,537,308 | B2 | 1/2020 | Zhadkevich |
| 10,542,924 | B2 | 1/2020 | Imran et al. |
| 10,568,686 | B2 | 2/2020 | Lee |
| 10,576,273 | B2 | 3/2020 | Goedeke et al. |
| 10,617,313 | B2 | 4/2020 | Smith |
| 10,631,788 | B2 | 4/2020 | Brody |
| 10,743,780 | B2 | 8/2020 | Hoem et al. |
| 10,750,999 | B2 | 8/2020 | Parks et al. |
| 10,758,135 | B2 | 9/2020 | Burnett et al. |
| 10,765,841 | B2 | 9/2020 | Zhadkevich |
| 10,772,998 | B2 | 9/2020 | Luxon |
| 10,773,059 | B1 | 9/2020 | Sardesai |
| 10,786,651 | B2 | 9/2020 | Edminster et al. |
| 10,813,589 | B2 | 10/2020 | McKinney et al. |
| 10,905,313 | B2 | 2/2021 | McHugh et al. |
| 10,918,831 | B2 | 2/2021 | Smith et al. |
| 10,952,659 | B2 | 3/2021 | Burnett et al. |
| 11,045,128 | B2 | 6/2021 | McKinney et al. |
| 11,045,143 | B2 | 6/2021 | McKinney et al. |
| 11,065,418 | B1 | 7/2021 | Brody |
| 11,077,301 | B2 | 8/2021 | Creasey |
| 11,185,245 | B2 | 11/2021 | McKinney et al. |
| 11,395,616 | B2 | 7/2022 | Kuck et al. |
| 11,406,302 | B2 | 8/2022 | Suehara et al. |
| 11,490,844 | B2 | 11/2022 | Imran et al. |
| 11,529,506 | B2 | 12/2022 | Geva et al. |
| 11,617,543 | B2 | 4/2023 | McKinney et al. |
| 11,648,380 | B2 | 5/2023 | McCloskey |
| 11,660,032 | B2 | 5/2023 | Silverton et al. |
| 11,672,457 | B2 | 6/2023 | McKinney et al. |
| 11,779,263 | B2 | 10/2023 | McKinney |
| 11,813,070 | B2 | 11/2023 | Janssen et al. |
| 11,832,947 | B2 | 12/2023 | McKinney et al. |
| 11,844,948 | B2 | 12/2023 | Chen et al. |
| 11,883,174 | B2 | 1/2024 | Burnett et al. |
| 11,938,277 | B2 | 3/2024 | Waitkus et al. |
| 11,969,248 | B2 | 4/2024 | McKinney et al. |
| 12,016,691 | B2 | 6/2024 | Suehara et al. |
| 12,064,087 | B2 | 8/2024 | Stoyanov et al. |
| 12,070,314 | B2 | 8/2024 | Suehara et al. |
| 2001/0001812 | A1 | 5/2001 | Valley et al. |
| 2002/0143294 | A1 | 10/2002 | Duchon et al. |
| 2002/0183628 | A1 | 12/2002 | Reich et al. |
| 2003/0060800 | A1 | 3/2003 | Ryan |
| 2003/0114835 | A1 | 6/2003 | Noda |
| 2003/0163052 | A1 | 8/2003 | Mott |
| 2003/0181856 | A1 | 9/2003 | Goldman |
| 2004/0077976 | A1 | 4/2004 | Wilson |
| 2004/0127813 | A1 | 7/2004 | Schwamm |
| 2004/0171942 | A1 | 9/2004 | Ackerman et al. |
| 2005/0015047 | A1 | 1/2005 | Shah |
| 2005/0055043 | A1 | 3/2005 | Foltz |
| 2005/0065408 | A1 | 3/2005 | Benderev |
| 2005/0119567 | A1 | 6/2005 | Choi |
| 2005/0187430 | A1 | 8/2005 | Aundal et al. |
| 2005/0197585 | A1 | 9/2005 | Brockway et al. |
| 2005/0215989 | A1 | 9/2005 | Abboud |
| 2005/0240211 | A1 | 10/2005 | Sporri |
| 2005/0283092 | A1 | 12/2005 | Gedebov |
| 2006/0011820 | A1 | 1/2006 | Chow-Shing et al. |
| 2006/0073728 | A1 | 4/2006 | Zaiken |
| 2006/0085022 | A1 | 4/2006 | Hayes |
| 2006/0085024 | A1 | 4/2006 | Pepper |
| 2006/0178571 | A1 | 8/2006 | Barnett |
| 2007/0083126 | A1 | 4/2007 | Marko et al. |
| 2007/0191904 | A1 | 8/2007 | Libbus et al. |
| 2007/0197963 | A1 | 8/2007 | Griffiths et al. |
| 2007/0282219 | A1 | 12/2007 | Holte |
| 2008/0027358 | A1 | 1/2008 | Gregersen et al. |
| 2008/0045822 | A1 | 2/2008 | Phillips et al. |
| 2008/0077043 | A1 | 3/2008 | Malbrain et al. |
| 2008/0103408 | A1 | 5/2008 | Denton et al. |
| 2008/0139967 | A1 | 6/2008 | Euliano |
| 2008/0146990 | A1 | 6/2008 | Jenson et al. |
| 2009/0177183 | A1 | 7/2009 | Pinkernell et al. |
| 2009/0221993 | A1 | 9/2009 | Sohi et al. |
| 2009/0240199 | A1 | 9/2009 | Rahimsobhani |
| 2009/0306539 | A1 | 12/2009 | Woodruff |
| 2009/0326390 | A1 | 12/2009 | Belalcazar et al. |
| 2010/0056952 | A1 | 3/2010 | Liu |
| 2010/0069900 | A1 | 3/2010 | Shirley |
| 2010/0094204 | A1 | 4/2010 | Nishtala |
| 2010/0094328 | A1 | 4/2010 | O'dea et al. |
| 2010/0113939 | A1 | 5/2010 | Mashimo et al. |
| 2010/0113968 | A1 | 5/2010 | Bobo |
| 2010/0121159 | A1 | 5/2010 | Burnett et al. |
| 2010/0168836 | A1 | 7/2010 | Kassab |
| 2010/0249663 | A1 | 9/2010 | Nishtala |
| 2011/0087109 | A1 | 4/2011 | Swann |
| 2011/0098683 | A1 | 4/2011 | Wiita |
| 2012/0010525 | A1 | 1/2012 | Jacofsky et al. |
| 2012/0035595 | A1 | 2/2012 | Goedje |
| 2012/0041334 | A1 | 2/2012 | Goedje et al. |
| 2012/0053441 | A1 | 3/2012 | Kassab |
| 2012/0136369 | A1 | 5/2012 | Gross et al. |
| 2012/0179063 | A1 | 7/2012 | Bharucha et al. |
| 2012/0234434 | A1 | 9/2012 | Woodruff et al. |
| 2012/0271339 | A1 | 10/2012 | O'Beirne et al. |
| 2012/0316460 | A1 | 12/2012 | Stout |
| 2012/0316461 | A1 | 12/2012 | Liu |
| 2013/0030262 | A1 | 1/2013 | Burnett et al. |
| 2013/0046217 | A1 | 2/2013 | Mooney |
| 2013/0066166 | A1 | 3/2013 | Burnett et al. |
| 2013/0079662 | A1 | 3/2013 | Damaser et al. |
| 2013/0085519 | A1 | 4/2013 | Kiminami |
| 2013/0096494 | A1 | 4/2013 | Kassab |
| 2013/0211221 | A1 | 8/2013 | Sunnarborg |
| 2013/0231584 | A1 | 9/2013 | Burnett |
| 2013/0317367 | A1 | 11/2013 | Shuler |
| 2014/0012305 | A1 | 1/2014 | Horton et al. |
| 2014/0052224 | A1 | 2/2014 | Kassab |
| 2014/0094716 | A1 | 4/2014 | Zaiken et al. |
| 2014/0107550 | A1 | 4/2014 | Paulson |
| 2014/0107573 | A1 | 4/2014 | Wiita et al. |
| 2014/0128766 | A1 | 5/2014 | Beran |
| 2014/0155745 | A1 | 6/2014 | Duncan |
| 2014/0163415 | A1 | 6/2014 | Zaiken |
| 2014/0200482 | A1 | 7/2014 | Shi |
| 2014/0243873 | A1 | 8/2014 | Franklin |
| 2014/0364835 | A1 | 12/2014 | Allen |
| 2015/0042406 | A1 | 2/2015 | Kovac et al. |
| 2015/0065807 | A1 | 3/2015 | Greenberg et al. |
| 2015/0133799 | A1 | 5/2015 | O'Connell et al. |
| 2015/0327836 | A1 | 11/2015 | Stone et al. |
| 2015/0342512 | A1 | 12/2015 | Shi |
| 2015/0351649 | A1 | 12/2015 | Bobo, Sr. et al. |
| 2015/0366462 | A1 | 12/2015 | Ramos et al. |
| 2015/0366485 | A1 | 12/2015 | Kassab |
| 2015/0366498 | A1 | 12/2015 | Choi et al. |
| 2016/0029912 | A1 | 2/2016 | Stimpson |
| 2016/0066831 | A1 | 3/2016 | Hyde et al. |
| 2016/0074581 | A1 | 3/2016 | Gerrans |
| 2016/0106323 | A1 | 4/2016 | Ou et al. |
| 2016/0183819 | A1 | 6/2016 | Burnett et al. |
| 2016/0220136 | A1 | 8/2016 | Schultz |
| 2016/0249969 | A1 | 9/2016 | Santoinanni |
| 2016/0256076 | A1 | 9/2016 | Kassab |
| 2016/0310148 | A1 | 10/2016 | Allen |
| 2016/0331294 | A1 | 11/2016 | Imran et al. |
| 2016/0331451 | A1 | 11/2016 | Nabutovsky et al. |
| 2016/0354028 | A1 | 12/2016 | Damaser et al. |
| 2016/0354140 | A1 | 12/2016 | Sharma |
| 2016/0374576 | A1 | 12/2016 | Ziaie et al. |
| 2017/0055874 | A1 | 3/2017 | Papirov et al. |
| 2017/0071566 | A1 | 3/2017 | Hart et al. |
| 2017/0079868 | A1 | 3/2017 | Reid, Jr. et al. |
| 2017/0100561 | A1 | 4/2017 | Burnett |
| 2017/0128012 | A1 | 5/2017 | Parks et al. |
| 2017/0136209 | A1 | 5/2017 | Burnett et al. |
| 2017/0156610 | A1 | 6/2017 | Quackenbush et al. |
| 2017/0156611 | A1 | 6/2017 | Burnett et al. |
| 2017/0160175 | A1 | 6/2017 | Al-Mayah |

(56) References Cited

U.S. PATENT DOCUMENTS

2017/0209048 A1 7/2017 Wiita
2017/0258345 A1 9/2017 Smith
2017/0259035 A1 9/2017 Smith et al.
2017/0273623 A1 9/2017 Chen et al.
2017/0273853 A1 9/2017 Nagata et al.
2017/0332955 A1 11/2017 Burnett et al.
2018/0049658 A1 2/2018 Smith
2018/0177458 A1 6/2018 Burnett et al.
2018/0184929 A1 7/2018 Burnett et al.
2018/0263515 A1 9/2018 Raval
2018/0311469 A1 11/2018 Wiita
2018/0326190 A1 11/2018 Nash
2018/0344183 A1 12/2018 McKinney et al.
2018/0344184 A1 12/2018 McKinney et al.
2018/0344234 A1 12/2018 McKinney et al.
2018/0344249 A1 12/2018 McKinney
2018/0344250 A1 12/2018 McKinney et al.
2019/0133460 A1 5/2019 Wine
2019/0133532 A1 5/2019 Zaiken
2019/0150801 A1* 5/2019 Suehara ............... A61B 5/1459
2019/0282109 A1 9/2019 Schlumpf et al.
2019/0321588 A1 10/2019 Burnett et al.
2019/0343445 A1 11/2019 Burnett et al.
2019/0350634 A1 11/2019 Jung
2019/0380762 A1 12/2019 Dahlen et al.
2020/0029906 A1 1/2020 Smith et al.
2020/0046237 A1 2/2020 Stimpson
2020/0069332 A1 3/2020 Callery
2020/0085378 A1 3/2020 Burnett et al.
2020/0164184 A1 5/2020 McKinney et al.
2020/0197019 A1 6/2020 Harper
2020/0215303 A1 7/2020 Erbey, II et al.
2020/0237242 A1 7/2020 Kaluzny et al.
2020/0253536 A1 8/2020 McKinney
2020/0261695 A1 8/2020 Jaroch et al.
2020/0305742 A1 10/2020 Ghodsain
2020/0324037 A1 10/2020 Bloomberg et al.
2020/0330723 A1 10/2020 Erbey, II et al.
2020/0359920 A1 11/2020 Burnett et al.
2020/0383703 A1 12/2020 Atad
2020/0384241 A1 12/2020 Herrera
2021/0000422 A1 1/2021 McKinney
2021/0015380 A1 1/2021 McKinney et al.
2021/0046277 A1 2/2021 Samoocha
2021/0052873 A1 2/2021 Geva
2021/0085252 A1 3/2021 McKinney et al.
2021/0128413 A1 5/2021 Elia
2021/0170149 A1 6/2021 Erbey, II et al.
2021/0177355 A1 6/2021 Govari
2021/0187240 A1 6/2021 Waitkus
2021/0244473 A1 8/2021 Cook et al.
2021/0244912 A1 8/2021 Paz
2021/0259555 A1 8/2021 Usui
2021/0290243 A1 9/2021 Franklin
2021/0290908 A1 9/2021 Raval
2021/0338126 A1 11/2021 McKinney et al.
2021/0369185 A1 12/2021 Janssen
2022/0000381 A1 1/2022 McKinney et al.
2022/0039751 A1 2/2022 Chey
2022/0047793 A1 2/2022 Manda
2022/0061764 A1 3/2022 Van Der Werf
2022/0134063 A1 5/2022 Kerschbaum
2022/0143372 A1 5/2022 Hvid et al.
2022/0241557 A1 8/2022 Erbey, II et al.
2022/0265914 A1 8/2022 Erbey, II et al.
2022/0273313 A1 9/2022 Ward et al.
2022/0288351 A1 9/2022 Franklin et al.
2022/0362515 A1 11/2022 Erbey, II et al.
2023/0097230 A1 3/2023 Geva et al.
2023/0210466 A1 7/2023 McKinney et al.
2023/0263442 A1 8/2023 Dove et al.
2024/0003868 A1 1/2024 Sawada
2024/0041343 A1 2/2024 Pandolfino et al.
2024/0066275 A1 2/2024 Kim
2024/0099624 A1 3/2024 Sutaria et al.
2024/0260873 A1 8/2024 McKinney et al.
2024/0306929 A1 9/2024 Janssen et al.

FOREIGN PATENT DOCUMENTS

CN 204582261 8/2015
CN 105073040 11/2015
CN 205649494 10/2016
EP 0097454 1/1984
EP 3656297 5/2020
WO WO 94/02195 2/1994
WO WO 1995/012351 5/1995
WO WO 2005/013834 2/2005
WO WO 2006/060248 6/2006
WO WO 2008/042347 4/2008
WO WO 2011/053500 5/2011
WO WO 2012/006624 1/2012
WO WO 2012/006625 1/2012
WO WO 2012/122267 9/2012
WO WO 2014/043650 3/2014
WO WO 2014/160300 10/2014
WO WO 2014/210453 12/2014
WO WO 2015/191125 12/2015
WO WO 2016/049654 3/2016
WO WO 2016/204631 12/2016
WO WO 2017/156451 9/2017
WO WO 2018/136306 7/2018
WO WO 2018/182913 10/2018
WO WO 2022/114542 6/2022
WO WO 2022/135370 6/2022
WO WO 2022/135371 6/2022
WO WO 2022/178032 8/2022
WO WO 2022/198807 9/2022
WO WO 2022/199568 9/2022
WO WO 2022/209694 10/2022
WO WO 2023/154185 8/2023
WO WO 2023/214417 11/2023
WO WO 2024/234016 11/2024
WO WO 2025/016782 1/2025

OTHER PUBLICATIONS

Search Report 18725349, Dated Dec. 10, 2023.

Extended European Search Report mailed Mar. 2, 2020 for European Application No. EP 19210264.8.

A randomized comparison of microtip and air-charged catheter for the measurement of maximum urethral closure pressure, Ginekol Pol. 2012, 83: 586-589.

Abdominal pressure in the critically ill: measurement and clinical relevance, Intensive Care Med, 1999, 25: 1453-1458.

(Abstract only) "Caring for critically injured children: An analysis of 56 pediatric damage control laparotomies". J Trauma Acute Care Surg. May 2017; 82: 901-909.

(Abstract only) "Estimation of Intra-abdominal Pressure by Bladder Pressure Measurement: Validity and Methodology", The Journal of Trauma Injury, Infection, and Critical Care, Feb. 2001, 50: 297-302.

(Abstract only) "Intra-Abdominal Pressure Monitoring in Neonates", Pediatric Critical Car Med. Feb. 2016; 17: 172-173.

(Abstract only) "Saline volume in transvesical intra-abdominal pressure measurement: Enough is enough", Intensive Care Med., Mar. 2006; 32: 455-459.

De Waele J., et al., "Saline volume in transvesical intra-abdominal pressure measurement: Enough is enough", Intensive Care Med.. Mar. 2006; 32: 455-459.

Determination of Intra-abdominal Pressure Using a Transurethral Bladder Catheter: Clinical Validation of the Technique, Anesthesiology, Jan. 1989, 70( 1 ), 47-50.

European Search Report EP 20850354.0 Dated Jul. 15, 2022.

European Search Report EP 20850354, Dated Oct. 6, 2022.

International search report and written opinion for international application PCT/US2018/028687 mailed Sep. 28, 2018.

International search report and written opinion for international application PCT/US2018/028693 mailed Sep. 28, 2018.

(56) References Cited

OTHER PUBLICATIONS

International search report for international application PCT/US2018/032467 mailed Sep. 5, 2018.
International search report for international application PCT/US2018/034781 mailed Sep. 5, 2018.
Is clinical examination an accurate indicator or raised intra-abdominal pressure in critically injured patents? CJS, Jun. 2000, 43, No. 3: 207-211.
Mark A. Fusco, et al.,"Estimation of Intra-abdominal Pressure by Bladder Pressure Measurement: Validity and Methodology", The Journal of Trauma Injury, Infection, and Critical Care, Feb. 2001, 50: 297-302.
Measurement on intra-abdominal pressure in large incisional hernia repair to prevent abdominal compartmental syndrome, G Chir, Jan.-Feb. 2016; 37: 31-36.
Miguel A. Villalobos, et al., "Caring for critically injured children: An analysis of 56 pediatric damage control laparotomies". J Trauma Acute Care Surg. May 2017, 82: 901-909.
Mudit Mathur, MD, "Intra-Abdominal Pressure Monitoring in Neonates", Pediatric Critical Car Med. Feb. 2016; 1 7: 172-173.
Pressure Measurement Techniques for Abdominal Hypertension: Conclusions from an Experimental Model, Crit Care Res Pract., May 2015: 278139.
Product information for Intra Compartment Pressure Wick's / Slit Catheter Set up (Stryker).
Product information for Intra-Compartmental Pressure Monitor System (Stryker).
Product information for Your Continuous Pressure Monitoring System (Mammendorfer Institut für Physik und Medizin GMbH).
Prospective Study of Intra-Abdominal Hypertension and Renal Function after Laparotomy, British Journal of Surgery, 1999, 82, 235-238.
Rudra, Pallab, et al. "Recent Advances in Management of Pre-Eclampsia" Sep. 2011, British Journal of Medical Practitioners, vol. 4, No. 3 (Year: 2011).
Sawchuck, Diane, et al. "Pre-eclampsia renamed and reframed: Intra-abdominal hypertension in pregnancy" Nov. 2014, Medical Hypothese, 83, 619-632 (Year: 2014).
Study of the occurrence of intra-abdominal hypertension and abdominal compartment syndrome in patients of blunt abdominal trauma and its correlation with the clinical outcome in the above patents, World J Emerg Surg. Feb. 11, 2016; 11: 9.
The Measurement of Intra-Abdominal Pressure as a Criterion of Abdominal Re-exploration, 1984 Ann Surg., 199: 28-30.
"The neglected role of abdominal compliance in organ-organ interactions", Critical Care. Mar. 2016; 1-10.
User's Manual for Compartmental Pressure Monitoring System. For continuous measurement of intra compartment pressure (Synthes).
Exam Report EP18733733.2 Dated—Nov. 6, 2024.
Betty Shamaev & May Shoshan, Bones: Custom cushioning helps heal a bad break, May 14, 2015, Science New Explores, health & Medicine, https://www.snexplores.org/article/bones-custom-cushioning-helps-heal-bad-break#:~:text=Two%20teens%20designed%20this,an%2associated%20cast%20(left), 2015 (Year: 2015).
Millar Micro-Tip® Pressure Transducer, Apr. 15, 2005, Millar Micro-Tip® Pressure Transducer, https://www.harvardapparatus.com/media/Harvard/pdf/BS4_J_5.pdf, 2005 (Year: 2005).
U.S. Pat. No. 10,980,989, 06/2005, Zilla, et al. (withdrawn)

* cited by examiner 640
644
646
642
642a

610

644a

602
D
C

B

CATHETER FOR MONITORING PRESSURE

This application is a continuation of application Ser. No. 18/127,804, filed Mar. 29, 2023, which is a divisional of application Ser. No. 16/675,358, filed Nov. 6, 2019, now U.S. Pat. No. 11,672,457, which claims priority from provisional application Ser. No. 62/865,360, filed Jun. 24, 2019 and from provisional application Ser. No. 62/771,040, filed Nov. 24, 2018. The entire contents of each of these applications are incorporated herein by reference.

BACKGROUND OF THE INVENTION

1. Field of the Invention

This application relates to a device and method for monitoring pressure in a body cavity.

2. Background

Traditionally, physicians relied on visual cues or physical examination to detect increase in intra-abdominal pressure (IAP). More recently Dr. Kirkpatrick and colleagues, in an article "Is Clinical Examination an Accurate Indicator of Raised Intra-Abdominal Pressure in Critically Injured Patients," CJS, June 2000, 43, No. 3, 207-211, showed that IAP measured through the patient's bladder was significantly more accurate than physical examination. That is, it was demonstrated that the clinical abdominal examination was insensitive and inaccurate when compared with urinary bladder pressure measurements.

Various tools for measuring IAP have been developed over the years. Many researchers have documented IAP measurements through almost every natural or manmade orifice in the body. Earlier crude forms of measuring IAP used bladder catheters, nasogastric tubes, and rectal tubes attached to a manometer. The nasogastric or the rectal route was better suited in rare cases of bladder rupture or situations where bladder catheters were contraindicated. However, due to local interferences, the nasogastric and the rectal tube measurements were neither reproducible nor logical as were the bladder catheters.

Thus, measuring of IAP through the bladder became more suitable. In 1989 Iberti and colleagues in an article entitled, "Determination of Intra-abdominal Pressure Using a Transurethral Bladder Catheter: Clinical Validation of the Technique," Anesthesiology, January 1989, 70(1), 47-50, validated the correlation of IAP using a catheter inserted in the bladder. Their study was key in using bladder pressure as the gold standard for measuring IAP. In 1995, Kron and colleagues published a study in "The Measurement of Intra-Abdominal Pressure as a Criterion for Abdominal Re-exploration, 1984 Ann Surg., 199, 28-30, comparing catheters in various body locations for measuring IAP. They measured IAP from the stomach using a nasogastric tube, from the rectum using a modified rectal tube, from the bladder using a modified bladder catheter, and direct abdominal pressure using a laparoscopic insufflator needle. They found that the bladder catheter had the best measurement of IAP and that the gastric and the rectal catheter measurements were less reliable due to dependence on the position of the catheter. Thus, clinicians generally agreed that the urinary bladder is the best-suited location for measurement of IAP.

The need for measuring IAP has become more important as physicians increasingly realized that organ failure and death were directly related to increase in IAP in certain high-risk patients. High abdominal pressure has been found to cause a decrease in function of the intestines, liver and blood vessels resulting in adverse consequences for the patients. Consequently, accurate measurement of IAP can help decrease patient morbidity and mortality. It has also been more recently discovered that pediatric and neonate population may also have need for IAP measurement to determine specific conditions.

Currently, there are few products available on the market to measure the IAP through the bladder. One device, the Bard IAP device, has a "valve clamp" which diverts urine from the main catheter drainage channel to measure IAP via converting hydrostatic pressure to a readable pressure gauge. This mechanism of IAP measurements is archaic and does not provide continuous pressure measurement when used with the standard 2-channel bladder drainage catheter. Two other manufacturers, Holtech and ConvaTec, also use a column of urine by connecting their kit to an existing bladder catheter. Their systems are cumbersome and the IAP readings are also not continuous. Biometrix has developed an IAP monitoring device which like other manufacturers relies on tapping into the main bladder drainage catheter, using a valve to measure the hydrostatic pressure. In 2008 Sugrue and colleagues, in an article "Prospective Study of Intra-Abdominal Hypertension and Renal Function after Laparotomy, British Journal of Surgery, 1999, 82, 235-238, suggested the use of 3-channel bladder drainage catheter so that the smaller channel, which was used for bladder irrigation, could be used to attach a pressure-monitoring device. The use of an extra channel made it possible to have continuous bladder drainage while measuring the bladder pressure. However, this bladder catheter did not provide a continuous pressure read because intermittently the operator needed to add 50 ml of water or saline to the bladder to record the IAP pressure. Thus, the pressure reading at best was intermittent since pressure readings were not performed when fluid was being added to the bladder. Consequently, although this was a step toward increasing the amount of pressure readings/recordings, it still was unable to conduct continuous pressure monitoring. Furthermore, it was still the same cumbersome IAP device set up which required a skilled person to add water before each IAP reading. Control of the amount of water added is critical since adding too much water to the bladder can falsely increase the pressure readings and also increase infection risk, thus further complicating the use.

It has also been recognized that most patients that have a need for measurement of IAP also need to have continuous drainage of the urinary bladder and thus devices need to account for this process.

Consequently, current devices placed in the bladder for measuring pressure require a continuous water column to maintain pressure readings. Thus, they fail to measure IAP continuously but only measure pressure intermittently. They also all rely on tapping into an existing bladder drainage catheter, which adds complications. Furthermore, they do not reduce the complexity of the procedure since they require constant retrograde insertion of a relatively large amount of fluid into the bladder, e.g., 50 cc, which increases the ICU workload. Still further, these devices increase the risk of complications and infections associated with fluid injection into the bladder. Fluid injection is also complicated since it needs to be closely monitored since too much fluid in the bladder can give false elevation of IAP readings, causing clinicians to take unnecessary steps in response to what is mistakenly believed is excess IAP.

It would therefore be advantageous to provide a device insertable into the bladder that accurately measures abdominal pressure without requiring adding water to the bladder to obtain such pressure readings. Such device would advantageously avoid the complications and risks associated with such fluid insertion. Furthermore, it would be advantageous if such device could continuously measure bladder pressure without interruption. This would advantageously enable a constant monitoring of IAP so critical time periods are not missed. It would further be advantageous to provide a device that improves the accuracy of the pressure reading in the bladder to more accurately determine IAP so necessary steps can be taken to address IAP only when warranted. Still further, it would be advantageous if such device could satisfy the foregoing needs and provide these enumerated advantages while being simple to use so that so that any of clinical staff with basic knowledge of bladder catheter insertion will be able to insert the device without relying on specially trained staff members. It would also be advantageous to provide such devices with these advantages for insertion into other body cavities for accurately measuring pressure within the cavity without the need for injecting fluid into the cavity.

SUMMARY

The present invention overcomes the deficiencies and disadvantages of the prior art. The present invention advantageously provides a catheter insertable into the cavity of the patient to determine pressure without requiring insertion of water or other fluid into the body cavity. The present invention provides catheters insertable into various regions of the patient such as the bladder to measure intra-abdominal pressure or maternal uterine contraction pressure or the uterine cavity to measure intrauterine pressure, the abdominal cavity, etc. The catheters can be used for example in rectal, abdominal, esophageal, cardiac, etc, procedures. The catheters of the present invention utilize a gas-charged chamber to measure pressure across a large surface area, and thus, accurately determine pressure, and enable pressure to be measured continuously without interruptions to add water to the cavity.

In some embodiments, an outer fluid filled balloon provides a fluid transmission medium for an inner pressure sensing balloon.

Some embodiments of the catheter of the present invention utilize a stabilizing balloon to help retain the catheter in the bladder during the procedure.

In accordance with one aspect of the present invention, a catheter is provided which is insertable into a patient for monitoring pressure. The catheter includes a first lumen having a wall and at least one side opening in the wall and an expandable outer balloon at a distal portion of the catheter. The outer balloon has a first outer wall and receives fluid to move from a first condition to a more expanded condition, and expands radially outwardly with respect to the catheter. An expandable inner balloon is positioned within the first lumen of the catheter and has a second outer wall and an elongated portion extending proximally through the first lumen, and has a gas containing chamber to monitor pressure within the patient. The outer balloon has a circumferential area greater than a circumferential area of the inner balloon wherein in response to pressure exerted on the first outer wall of the expanded outer balloon fluid within the outer balloon enters the at least one opening in the wall of the lumen to exert a pressure on the second outer wall of the expanded inner balloon to deform the inner balloon and compress the gas within the inner balloon. A pressure sensor communicates with the gas containing chamber for measuring pressure based on compression of gas caused by deformation of the expanded inner balloon resulting from deformation of the expanded outer balloon.

In some embodiments, the outer balloon is inflated via a second lumen independent of the first lumen. In some embodiments, the inner balloon in the expanded position remains within the confines of the first lumen.

In some embodiments, a chamber is provided containing a plurality of openings communicating with the interior of the outer balloon.

In some embodiments, the catheter includes an additional lumen and a stabilizing balloon, the additional lumen communicating with the stabilizing balloon to inflate the stabilizing balloon to stabilize the position of the catheter. The stabilizing balloon can be positioned proximal of the outer balloon.

In some embodiments, the inner and outer balloons have a coating to increase impermeability.

In some embodiments, the pressure sensor is contained within a hub and the hub includes an elongated member extending distally therefrom, and connection of the hub to a first port of the catheter automatically inserts the elongated member into the catheter to advance air into the inner balloon to expand the inner balloon.

In some embodiments, the first lumen is not vented to atmosphere when the pressure sensor is connected to the catheter and advances gas to expand the inner balloon.

In some embodiments, the gas within the inner balloon and/lumen is air to provide an air containing chamber.

In some embodiments, an elongated member is positioned within the tubular portion of the inner balloon to decrease the volume of gas within the tubular portion.

In some embodiments, a third balloon is positioned within the outer balloon, the third balloon being less compliant than the outer balloon and forming an inner liner of the outer balloon to maintain an expanded condition of the outer balloon.

In accordance with another aspect of the present invention, a catheter insertable into a patient for monitoring pressure within a body cavity without insertion of fluid into the cavity is provided, the catheter including a wall having at least one side opening and an expandable outer balloon at a distal portion of the catheter having a first outer wall and movable from a first condition to a more expanded condition. An inner balloon is movable to a more expanded condition, the inner balloon having a second outer wall and a gas containing chamber. The second outer wall of the inner balloon is radially spaced from the first outer wall of the outer balloon, the outer balloon acting as a medium for transfer of fluid to a second outer wall of the inner balloon to deform the inner balloon for monitoring fluid pressure. The inner balloon has an elongated portion extending proximally through a lumen of the catheter. In response to pressure exerted on the first outer wall of the expanded outer balloon, fluid within the outer balloon enters the at least one side opening in the wall of the catheter to exert a pressure on the second outer wall of the expanded inner balloon to deform the inner balloon and compress the gas within the inner balloon to provide a pressure measurement. A pressure sensor communicates with the gas containing chamber of thinner balloon for measuring pressure based on compression of gas caused by deformation of the expanded inner balloon resulting from deformation of the expanded outer balloon, the pressure sensor measuring pressure at multiple times during a procedure without injecting fluid within the body cavity as the outer balloon provides the fluid transfer medium.

In some embodiments, the elongated portion of the inner balloon along with an enlarged portion of the inner balloon forms the gas chamber to monitor pressure within the patient. In some embodiments, the second outer wall of the inner balloon does not expand outside the lumen of the catheter when the inner balloon is in the expanded condition.

In accordance with another aspect of the present invention, a method for measuring pressure within a body cavity without insertion of fluid is provided including the steps of:

a) providing a catheter having an inner balloon and an outer balloon, a wall of the inner balloon spaced from a wall of the outer balloon, the inner balloon having a first region with an outer wall to receive fluid thereon from the outer balloon and an elongated region communicating with the first region and extending within a lumen of the catheter;
b) inserting the catheter into the body cavity of a patient;
c) expanding the inner balloon from a first condition to a more inflated condition, an internal space of the balloon forming a gas containing chamber;
d) either before or after step (c) expanding the outer balloon from a first condition to a more inflated condition; and
e) obtaining multiple pressure readings within the body cavity during a procedure based on deformation of the outer balloon which causes deformation of the inner balloon to thereby monitor pressure, the outer balloon providing a medium for transfer of fluid against the outer wall of the inner balloon for multiple pressure measurements without requiring insertion of fluid into the body cavity.

The method can include the step of transmitting the pressure readings to an external monitor.

In some embodiments, deformation of the outer balloon is in response to pressure exerted on an outer wall of the expanded outer balloon and upon such deformation, gas within the outer balloon enters one or more openings in the catheter to communicate with the outer wall of the expanded inner balloon to exert a pressure on and deform the inner balloon and compress the gas within the inner balloon.

The method may further comprise the step of connecting to the catheter a hub containing a pressure transducer to automatically advance gas into the inner balloon to expand the inner balloon. In some embodiments, the step of connecting the hub automatically connects a temperature sensor to a connector within the hub.

In accordance with some aspects of the present invention, catheters are insertable into the bladder and utilized for measuring intra-abdominal pressure. In some such embodiments, the gas containing chamber monitors pressure within the bladder to thereby monitor pressure within an abdomen of the patient. In some embodiments, the pressure transducer measures average pressure continuously throughout insertion of the catheter within the urethra without requiring infusion of water into the bladder.

In some embodiments, a second lumen communicates with the bladder to remove fluid from the bladder. In some embodiments, the second lumen has a side opening distal of the inner and outer balloons; in other embodiments the side opening is proximal of the inner and outer balloons. The catheter can include a third lumen communicating with the outer balloon to expand the outer balloon.

In some embodiments, the catheter has a fourth lumen and a temperature sensor positioned within the fourth lumen to measure core body temperature. A wire can extend from the temperature sensor through the fourth lumen and external of the catheter into the hub connected to the catheter. The hub can have a first opening to receive a connector of the wire to automatically connect the temperature sensor to a cable extendable from the hub and connectable to an external temperature monitor.

In some embodiments, connection of the pressure sensor to the catheter a) automatically connects the temperature sensor to a temperature monitor cable; and b) automatically advances air through the first lumen to expand the inner balloon.

In accordance with another aspect of the present invention, a method for measuring intra-abdominal pressure is provided comprising the steps of:

providing a catheter having first and second lumens, an expandable first balloon and a temperature sensor;
inserting the catheter through the urethra into a bladder of a patient;
connecting a hub containing a pressure transducer to the first lumen to automatically advance air through the first lumen of the catheter to expand the first balloon from a deflated condition to a more expanded condition and to automatically connect the temperature sensor to a connector within the hub;
obtaining a first pressure reading of the bladder based on deformation of the balloon without injecting fluid into the bladder;
transmitting the first pressure reading to an external monitor connected to the hub;
obtaining a second pressure reading of the bladder based on deformation of the balloon without injecting fluid into the bladder;
transmitting the second pressure reading to the external monitor connected to the hub; and
obtaining consecutive continuous pressure readings of the bladder without injecting fluid into the bladder.

The method can further include the step of draining the bladder through the second lumen of the catheter. In some embodiments, the step of obtaining pressure readings obtains average pressure.

In accordance with another aspect of the present invention, a multi-lumen catheter for monitoring intra-abdominal pressure is provided. The catheter includes an elongated body configured and dimensioned for insertion into a bladder of a patient, a first lumen, a second lumen, and a third lumen, the lumens being independent. A first balloon is positioned at a distal portion and the first lumen communicates with the first balloon. The second lumen communicates with the bladder to remove fluid from the bladder. The first balloon and first lumen are filled with a gas to form a gas filled fully closed chamber to monitor pressure within the bladder to thereby monitor pressure within an abdomen of the patient. A pressure sensor measures pressure within the bladder based on deformation of the first balloon in response to pressure within the bladder exerted on an outer wall of the balloon, the pressure sensor measuring bladder pressure continuously and communicating with an external monitor to visually display pressure readings, the sensor providing continuous pressure measurements throughout its duration of insertion without requiring infusion of water into the bladder.

In accordance with another aspect of the present invention, a system for monitoring intra-abdominal pressure is provided comprising a catheter having an elongated body configured and dimensioned for insertion into the bladder of a patient, a first lumen, a second lumen, a third lumen, and a first balloon at a distal portion. The first lumen communicates with the first balloon and the second lumen communicates with the bladder to remove fluid from the bladder. The first balloon and first lumen are filled with a gas to form a gas filled fully closed chamber to monitor pressure within the bladder to thereby monitor pressure within an abdomen of the patient. A pressure sensor measures bladder pressure continuously and communicates with an external monitor to visually display pressure readings, the sensor providing continuous pressure measurements during its insertion without requiring infusion of water into the bladder. An indicator indicates if the measured pressure exceeds a threshold value.

The indicator can be a visual and/or audible indicator.

In accordance with another aspect, the present invention provides a method for measuring intra abdominal pressure comprising the steps of a) providing a catheter having first and second lumens and a balloon; b) inserting the catheter into a bladder of a patient; c) injecting gas into the first lumen of the catheter to expand the balloon from a deflated condition to a partially inflated condition; d) obtaining a first pressure reading of the bladder based on deformation of the balloon without injecting fluid into the bladder; e) transmitting the first pressure reading to an external monitor connected to the catheter; f) obtaining a second pressure reading of the bladder based on deformation of the balloon without injecting fluid into the bladder; g) transmitting the second pressure reading to the external monitor connected to the catheter; and h) obtaining consecutive continuous pressure readings of the bladder without injecting fluid into the bladder.

The method can include measuring the temperature of a body of a patient utilizing a temperature sensor within the first lumen.

In accordance with another aspect of the present invention, a multi-lumen catheter is provided that is insertable into a patient for monitoring pressure. The catheter comprises an expandable outer balloon at a distal portion of the catheter, the outer balloon having a first outer wall and receiving fluid to move from a first condition to a more expanded condition. A chamber is positioned within the outer balloon and contains a plurality of openings communicating with the interior of the outer balloon. An expandable inner balloon is positioned within the chamber and has a second outer wall. A first lumen communicates with the inner balloon, the inner balloon and first lumen forming a gas filled chamber to monitor pressure within the patient, wherein the outer balloon has a circumferential area greater than a circumferential area of the inner balloon, wherein in response to pressure exerted on the first outer wall of the expanded outer balloon fluid within the outer balloon enters one or more of the openings in the chamber to exert a pressure on the second outer wall of the expanded inner balloon to deform the inner balloon and compress the gas within the inner balloon and the first lumen to provide a finer measurement. A pressure sensor communicates with the gas filled chamber for measuring pressure based on compression of gas caused by deformation of the expanded inner balloon resulting from deformation of the expanded outer balloon.

In accordance with another aspect of the present invention, a multi-lumen catheter insertable into a patient for monitoring pressure is provided, the catheter comprising a shaft having first, second and third lumens, an expandable outer balloon at a distal portion of the catheter having an outer wall and receiving fluid via the second lumen to move from a first condition to a more expanded condition and a chamber positioned within the outer balloon containing a plurality of openings communicating with the interior of the outer balloon. An expandable inner balloon is positioned within the chamber and has an outer wall and a tubular portion extending within the first lumen. The outer balloon has a circumferential area greater than a circumferential area of the inner balloon, wherein in response to pressure exerted on the outer wall of the expanded outer balloon, fluid within the outer balloon enters one or more of the openings in the chamber to exert a pressure on the outer wall of the expanded inner balloon to deform the inner balloon and compress the gas within the inner balloon. A pressure sensor communicates with the gas within the inner balloon for measuring pressure based on compression of gas caused by deformation of the expanded inner balloon resulting from deformation of the expanded outer balloon.

In accordance with another aspect of the present invention, a multi-lumen catheter insertable into a patient for monitoring pressure is provided comprising a shaft having a first lumen, a second lumen and a third lumen. The third lumen of the catheter has an opening for drainage of a cavity. An expandable outer balloon is positioned at a distal portion of the catheter, the outer balloon having an outer wall and receiving fluid via the second lumen to move from a first condition to a more expanded condition. A plug is positioned within the third lumen of the catheter to provide a distal region and an expandable inner balloon is positioned within the distal region distal of the plug, the inner balloon having an outer wall and further having a tubular portion extending within the first lumen. The tubular portion has an angled portion so the tubular portion extends from the distal region into the first lumen. The outer balloon has a circumferential area greater than a circumferential area of the inner balloon, wherein in response to pressure exerted on the outer wall of the expanded outer balloon fluid within the outer balloon and exerts a pressure on the outer wall of the expanded inner balloon to deform the inner balloon and compress the gas within the inner balloon. A pressure sensor communicates with the gas within the inner balloon for measuring pressure based on compression of gas caused by deformation of the expanded inner balloon resulting from deformation of the expanded outer balloon.

In accordance with another aspect of the present invention, a multi-lumen catheter insertable into a patient for monitoring pressure is provided. The catheter comprises a catheter shaft having a distal end formed of a first material, an expandable outer balloon at a distal portion of the catheter having an outer wall and receiving fluid to move from a first condition to a more expanded condition, and an expandable inner balloon positioned within the outer balloon, the inner balloon having a second outer wall. A connecting pin is positioned at the distal end of the catheter and is positioned in the distal opening of the catheter extending distally therefrom. The connecting pin is composed of material different than the first material and the inner balloon is composed of material different than the first material and attached to the core pin. A first lumen communicates with the inner balloon and extends through the catheter shaft, the first lumen radially spaced from the connecting pin. The inner balloon and first lumen form a gas filled chamber to monitor pressure within the patient, wherein the outer balloon has a circumferential area greater than a circumferential area of the inner balloon, wherein in response to pressure exerted on the outer wall of the expanded outer balloon a pressure is exerted on the outer wall of the expanded inner balloon to deform the inner balloon and compress the gas within the inner balloon and the first lumen to provide a finer measurement. A pressure sensor communicates with the gas filled chamber for measuring pressure based on compression of gas caused by deformation of the expanded inner balloon resulting from deformation of the outer balloon.

In accordance with another aspect of the present invention, a multi-lumen catheter insertable into a patient for monitoring pressure is provided. The catheter includes a catheter body, a first balloon at a distal portion of the catheter balloon having a first outer wall expandable from a first condition to a more expanded condition and a second balloon having a second outer wall. The first balloon is external of the second balloon and the second balloon forms a fluid containing chamber to monitor pressure within the patient. A third balloon is positioned external of the first balloon such that the first balloon is positioned within the third balloon, the first balloon being less compliant than the third balloon and forming an inner liner of the third balloon to maintain an expanded condition of the third balloon. In response to pressure exerted on an outer wall of the expanded third balloon fluid within the first balloon enters one or more openings in the catheter to exert a pressure on the second outer wall of the expanded second balloon to deform the second balloon and compress the fluid within the second balloon to provide a pressure measurement.

The catheter can include a pressure sensor communicating with the fluid chamber for measuring pressure based on compression of fluids caused by deformation of the expanded second balloon resulting from deformation of the expanded first and third balloons.

In some embodiments the fluid chamber is a gas containing chamber which can in some embodiments be an air containing chamber.

In some embodiments, the catheter has a first lumen and the second balloon has an elongated portion extending through the first lumen and forming an elongated channel, the elongated channel along with the second balloon forming the gas filled chamber to monitor pressure within the patient.

The catheter can include one or more additional lumens to communicate with the bladder to remove fluid from the bladder and/or to inflate a retention balloon and/or inflate the first balloon. Preferably, the inner space of the first and second balloons are not in fluid communication so they are independently inflatable and deflatable.

The second balloon in some embodiments is maintained centered within the first lumen of the catheter so the second outer wall of the second balloon does not contact an inner wall of the first lumen of the catheter.

The catheter can have a sensor to measure core body temperature and a plurality of wires extending from the temperature sensor through the catheter.

In accordance with another aspect of the present invention, a method for measuring intra-abdominal pressure is provided comprising the steps of:

- providing a catheter having an inner balloon, an outer balloon and an intermediate balloon;
- inserting the catheter into a bladder of a patient;
- expanding the inner balloon from a first condition to a more inflated condition, an internal space of the balloon forming a gas containing chamber;
- expanding the intermediate balloon from a first condition to a more inflated condition, wherein expanding the intermediate balloon expands the outer balloon from a first condition to a more inflated condition;
- obtaining a first pressure reading of the bladder based on deformation of the outer balloon which causes deformation of the intermediate balloon which causes deformation of the inner balloon to thereby monitor pressure; and
- transmitting the first pressure reading to an external monitor connected to the catheter.

In some embodiments, deformation of the outer balloon is in response to pressure exerted on an outer wall of the expanded outer balloon, and upon such deformation fluid within the intermediate balloon enters one or more openings in the catheter to communicate with an outer wall of the expanded inner balloon to exert a pressure on and deform the inner balloon and compress the gas within the inner balloon to provide a finer pressure measurement. Preferably, fluid within the intermediate balloon does not enter inside the inner balloon.

Various uses of the catheter are provided including for example, the gas chamber monitoring pressure within a patient's bladder to thereby monitor pressure within an abdomen of the patient, monitoring pressure within a patient's bladder to thereby monitor uterine contraction pressure or monitoring pressure within a uterus of the patient to determine if excessive pressure is being applied to fallopian tubes of the patient.

In some embodiments, connecting a hub containing a pressure transducer to the catheter automatically advances gas into the inner balloon to expand the inner balloon and can also automatically connect a temperature sensor to a connector within the hub.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIGS. 32A, 32B, 32C and 32D illustrate the manufacturing steps of assembly of the catheter of FIG. 30A wherein FIG. 32A shows the connecting pin inserted into the catheter shaft; FIG. 32B shows the inner balloon attached to the connecting pin; FIG. 32C shows the distal tip connected to the pin; and FIG. 32D shows the outer balloon attached to the shaft and distal tip;

FIG. 48A is a perspective view of the distal end of the catheter of FIG. 47A;

DETAILED DESCRIPTION OF PREFERRED EMBODIMENTS

Figure 1A:
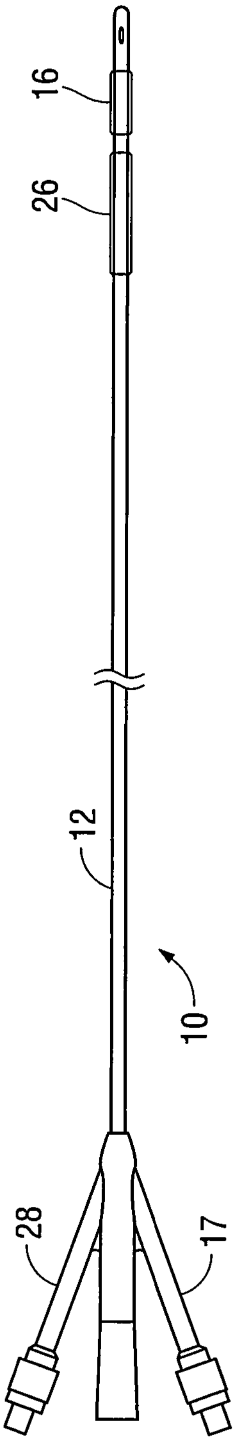
FIG. 1A is a side view of a first embodiment of the catheter of the present invention having a pressure balloon, a stabilizing balloon and a sensor positioned in the air lumen, both balloons shown in the deflated (collapsed) condition.
Figure 1B:
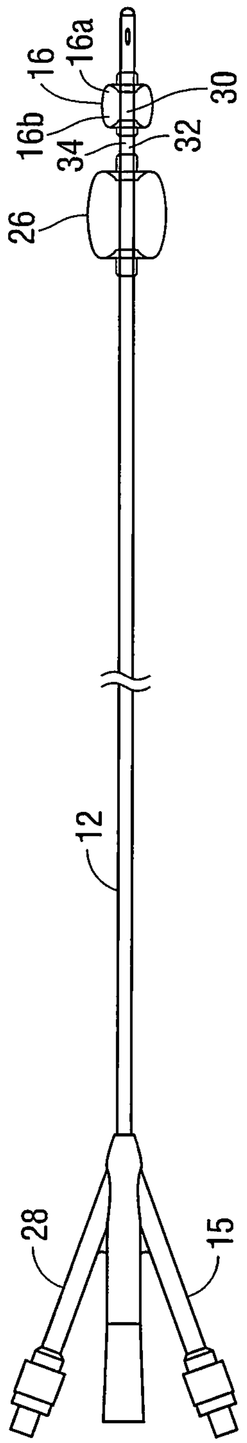
FIG. 1B is a side view similar to FIG. 1A showing the two balloons in the inflated (expanded) condition.

Increased abdominal pressure can cause many adverse conditions including diminishing the function of the intestines, liver, and blood vessels. Simply viewing or feeling the abdomen does not provide sufficient information or reading of health conditions.

It is recognized that urinary bladder pressure directly correlates to the intra-abdominal pressure. Although pressure readings can be determined by access to the esophagus or rectum, the bladder has been found to be the most accurate and the least invasive. In trauma or burn patients for example, time is critical and the less complicated the method for determining bladder pressure the better the clinical results.

The catheters of the present invention measure abdominal pressure via measurement of bladder pressure without filling the bladder with water. This avoids the risks associated with retrograde filling of the bladder with water as such retrograde filling not only increases the complications and workload for the intensive care (IC) staff and can create inaccuracies by providing false elevation of IAP readings, but can adversely affect the patient by increasing the risk of infection. Furthermore, by avoiding refilling of the bladder, bladder pressure can be measured continuously. This is because in devices requiring filling the bladder with water, water needs to be periodically added to the bladder to replace the water drained from the bladder and measurement readings are interrupted during water insertion. Due to these repeated interruptions, pressure cannot be read continuously. Note in some cases, as much as 50 cc of fluid needs to be repeatedly added to the bladder.

The catheters of the present invention efficiently and effectively measure bladder pressure without requiring filling the bladder with water. Also, as will become apparent from the discussion below, the catheters of the present invention provide a more accurate reading of pressure and enable continuous monitoring of the bladder pressure. This is all achieved in an easy to insert device.

It should be noted that the catheters of the present invention can be utilized for measuring other pressure in a patient and are not limited to intra-abdominal pressure. The catheters of the present invention can also be inserted into a variety of body cavities of the patient and can be used for monitoring pressure of various body regions. These catheters can be used in various body cavities for measuring pressure without requiring insertion of water into the body cavity and thus have the numerous advantages associated with requiring water as described herein.

Furthermore, in some embodiments, the catheters of the present invention have a dual sensor to provide a backup pressure reading. In some embodiments, a dual pressure balloon arrangement is provided. These various embodiments are discussed in more detail below.

Referring now to the drawings and particular embodiments of the present invention wherein like reference numerals identify similar structural features of the devices disclosed herein, there is illustrated in FIGS. 1A-5 a catheter of a first embodiment of the present invention. The catheter (device) is designated generally by reference numeral 10 and is configured for insertion into and positioning within the bladder of the patient for measuring intra-abdominal pressure, although it can be used to measure pressure of other body regions and inserted into other body regions. This measurement is to check if the intra-abdominal pressure exceeds a specified threshold since if such threshold is exceeded, there is a risk to the patient as discussed above and steps need to be taken to reduce the pressure such as draining additional fluid from the abdomen, opening the abdomen, etc.

The catheter 10 of the present invention can in some embodiments include an alarm or indicator to alert the user if pressure within the bladder, which correlates to pressure within the abdomen, rises to an unacceptable level, i.e., beyond a threshold or predetermined value (pressure). The indicator or alarm can be on the catheter or alternatively on an external device such as the monitor as discussed in more detail below. The alarm can also be connected via wireless connection to a phone or remote device to alert the appropriate personnel. The indicator or alarm can alternatively or in addition be activated if a change in pressure measurement exceeds a specified rate over a specified period of time.

Turning now to details of the catheter 10, which is also referred to herein as the device 10, and with initial reference to FIGS. 1A, 1B, 3 and 4 the catheter 10 of this embodiment has an elongated flexible shaft 12 having a lumen (channel) 14 extending within the shaft 12 and communicating at its distal region with balloon 16 to fluidly communicate with balloon 16 to inflate the balloon. Balloon 16 is utilized for monitoring pressure and is also referred to herein as the "pressure balloon." A fluid port 15 is positioned at a proximal region 17 of the catheter 10 for communication with an infusion source for infusion of gas, e.g., air, through the lumen 14 and into the balloon 16. The catheter 10 is shown in FIG. 1A with balloon 16 in the deflated condition (position) and in FIG. 1B with the balloon 16 in the inflated condition (position). The shaft 12 also includes a second lumen (channel) 20 and third lumen (channel) 24 extending therein (see also FIG. 5). In a preferred embodiment, the second lumen 20 is the largest lumen and is configured for continuous drainage of bodily contents from the bladder and can be connected to a drainage bag for collection of urine. Second lumen 20 has a side opening 22 at a distal portion, best shown in FIG. 3, communicating with the bladder. The third lumen 24 terminates at its distal end within balloon 26 to fluidly communicate with balloon 26 to inflate the balloon 26. The balloon 26 is inflatable to stabilize the catheter 10 to limit movement of the catheter 10 to keep it in place within the bladder and is also referred to herein as "the stabilizing balloon 26." A fluid port 28 is positioned at a proximal region 17 of the catheter 10 for communication with an infusion source for infusion of fluid through the lumen 24 and into the balloon 26. The balloon 26 can be filled with fluid, e.g., liquid such as water or saline, or a gas, e.g., air. In FIG. 1A, the balloon 26 is shown in the deflated condition and in FIG. 1B in the inflated condition.

Figure 5:
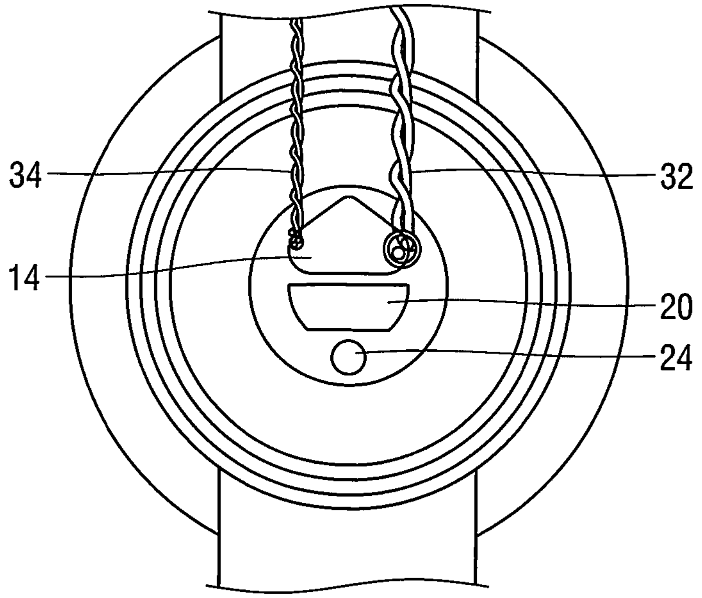
FIG. 5 is an enlarged transverse cross-sectional view of the catheter of FIG. 1.
Figure 6:
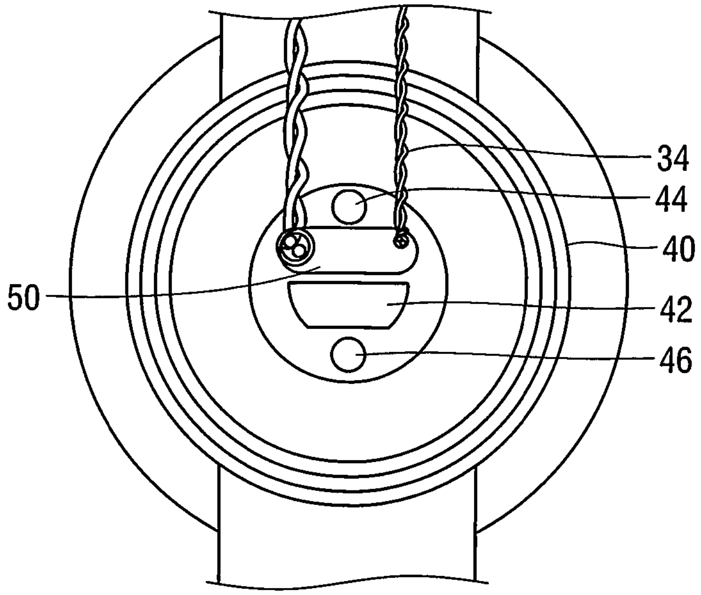
FIG. 6 is an enlarged transverse cross-sectional view of an alternate embodiment of a catheter of the present invention having four lumens.

Note FIG. 5 is a transverse cross-section of the catheter showing the three lumens of various shapes. These cross-sectional shapes of the lumens are provided by way of example as one or more of the lumens can be circular, oval or other symmetrical or asymmetrical shapes in transverse cross section. This also applies to the cross-sectional views of the other embodiments herein, e.g., FIGS. 6, 10B and 23, 30C, 45B, wherein the lumens can be shapes other than those shown. As noted above, preferably the drainage lumen is the largest lumen but in alternate embodiments one or more of the other lumens could be larger than the drainage lumen.

A sensor 30 is positioned within lumen 14 adjacent balloon 16. The wire(s) 32 are shown extending through lumen 14, the sensor 30 and wire(s) 32 being of sufficiently small size so as not to interfere with air flow though lumen 14. The sensor 30 measures pressure of the bladder. The sensor 30 is part of a transducer for converting the variation in pressure to an electrical signal for transmission to an external monitor. The pressure sensor can also include a temperature sensor, or alternatively another sensor for sensing temperature could be provided, to measure core temperature of the body as seen inside the bladder. Transmission wire(s) 34 of the temperature sensor extend adjacent wire 32 through lumen 14 and terminate external of the catheter 10 for connection to an external monitor. The transducer can be wired directly to the monitor or alternatively wired to a converter external of the catheter for converting the signal received by the transducer and transmitting a signal to the monitor, e.g., a bedside monitor, to display the pressure readings. This is shown schematically in FIG. 2. The readings can be displayed in quantitative form, graphical form or other displays to provide an indicator to the clinician of the bladder pressure. The monitor, or a separate monitor, will also display the temperature readings from sensor 30. Alternatively, the sensor/transducer can be connected to the monitor via a Bluetooth wireless connection.

Wires 32 and 34 can extend though lumen 14 and exit side port 15 for connection to a converter or monitor or alternatively can be inserted through the lumen 14, piercing the wall to enter the lumen 14 distal of the side port.

An alarm system can also be provided wherein the system includes a comparator for comparing the measured pressure (and/or temperature) to a threshold (predetermined) value, and if such threshold is exceeded, an indicator, e.g., an alarm, is triggered to indicate to the hospital personnel the excessive pressure and/or temperature. An alarm system can alternatively or in addition be activated if a change in pressure measurement exceeds a specified rate over a specified period of time. This would alert the staff to an imminent risk prior to intra-abdominal pressure exceeding a certain value, e.g., 20 mm hg, since due to this link, the relationship between intra-abdominal pressure and abdominal cavity volume is believed to be linear up to an intra-abdominal pressure of 12-15 mm hg and increasing exponentially thereafter.

Figure 2:
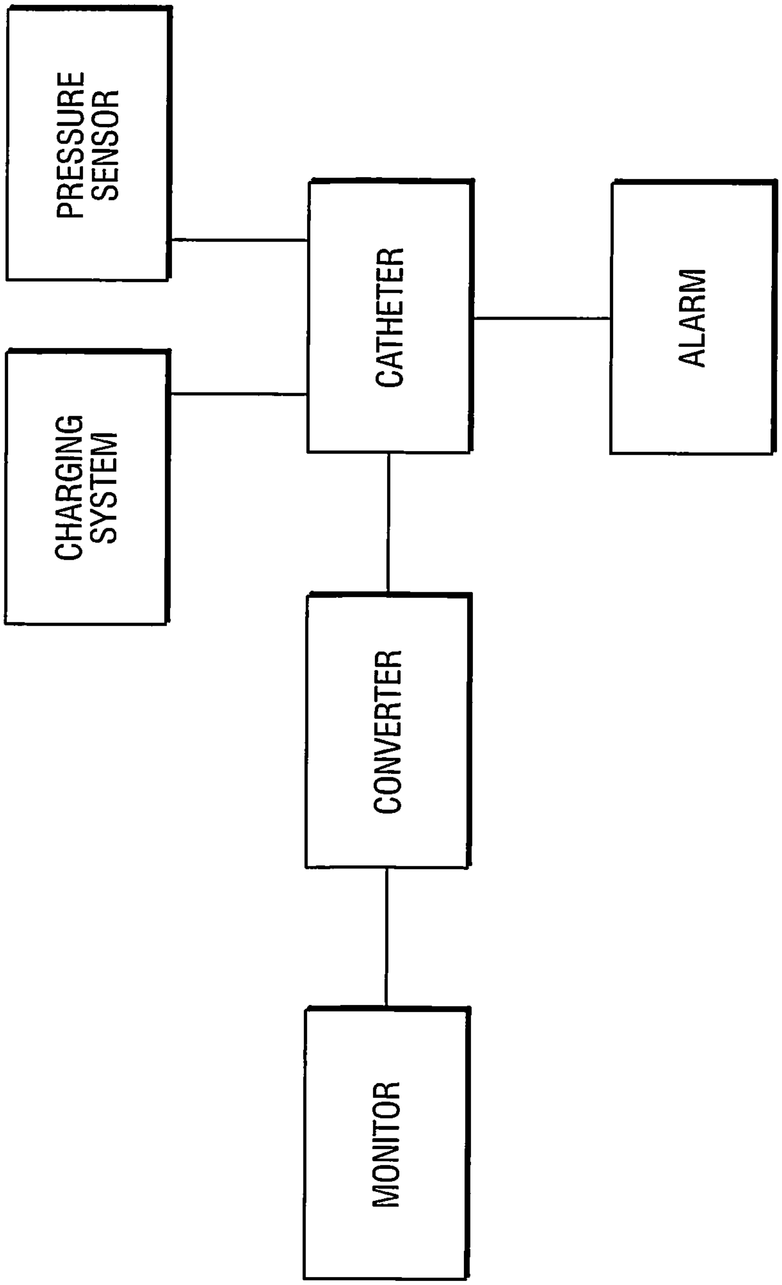
FIG. 2 is a schematic view of the system utilizing the catheter of FIG. 1A with an alarm system.

The alarm system can be part of the catheter (as shown in FIG. 2) or alternatively external to the catheter 10.

The lumen 14 and space 16*a* within balloon 16 together form a closed gas, e.g., air, chamber, i.e., the lumen 14 forming an air column. With the balloon 16 filled with air, pressure on the external wall of the balloon will force the balloon to deform inwardly, thereby compressing the air contained within the balloon space 16*a* and within the lumen 14. The pressure sensor 30 is located in a distal portion of the lumen 14 at the region of the balloon 16 and thus is positioned at the distal end of the air column. Therefore, the pressure is sensed at the distal region as the sensor 30 detects change in air pressure in lumen 14 due to balloon deformation. Placement of the sensor 30 at a distal location provides a pressure reading closer to the source which advantageously increases the accuracy because it reduces the risk of transmission issues by reducing the amount of interference which could occur due to water, air, clots, tissue, etc. if the transmission is down the air lumen (air column).

Additionally, the pressure measurement occurs about a more circumferential area of the balloon 16 providing a pressure reading of a region greater than a point pressure sensor reading. Also, average pressure over an area of the bladder wall can be computed. Thus, the area reading gleans information on pressure over more of the bladder wall. Stated another way, the balloon has a relatively large surface area with multiple reference points to contribute to average pressure readings of the surface around it by the sensor.

The air column is charged by insertion of air through the side port 15 which communicates with lumen 14. The side port 15 includes a valve to provide a seal to prevent escape of air from a proximal end. The balloon 16 can be composed of impermeable material, or in alternative embodiments, a permeable or semi-permeable material with an impermeable coating. This seals the air column at the distal end to prevent escape of air through the distal end, i.e., through the wall of the balloon 16. Thus, with the lumen sealed at the proximal and distal ends, a closed air system is provided, and without the requirement for repeated water insertion, a fully closed unit is provided.

In some embodiments, when the lumen 14 is air charged, the balloon 16 is not fully inflated. This improves the accuracy of the balloon 16 transmitting pressure from external the balloon to the interior of the balloon and into the lumen, i.e., air column, by ensuring the balloon has sufficient compliancy to prevent the balloon from introducing artifact into the pressure reading which would diminish its accuracy.

In some embodiments, the pressure balloon 16 is of a size to receive at least about 3 cc (3 ml) of fluid. However, other sizes/volumes are also contemplated such as about 2 cc or about 1 cc. Additionally, these volumes represent the maximum volume of fluid for the balloon, however, as noted above, in preferred embodiments, the pressure balloon 16 is not fully inflated so it would receive less than the maximum volume. Thus, with a balloon of X volume, the fluid would receive X-Y fluid, with Y representing the amount of desired extra space to achieve desired compliancy of the balloon while still enabling sufficient inflation of the balloon to achieve its pressure induced deformation function.

Note in this embodiment, the stabilizing balloon 26 is positioned proximal of the pressure balloon 16. Also, in this embodiment, the stabilizing balloon 26 is larger than the pressure balloon 16. By way of example, the stabilizing balloon 26 can have a fully expanded diameter of about 23 mm and the pressure balloon 16 can have a fully expanded diameter of about 15 mm, although other dimensions or diameters for these balloons are also contemplated. By way of example, the stabilizing balloon 26 can have a capacity of about 10 cc (10 ml) of air, although other sizes/volumes are also contemplated. Note these sizes/volumes for both balloons are provided by way of example and other sizes are also contemplated. Alternatively, the stabilizing balloon can be the same size or smaller than the pressure balloon. Various shapes of the balloons are also contemplated.

Additionally, although the balloon 26 is positioned proximal of the balloon 16, it is also contemplated that the balloon 26 be positioned distal of balloon 16. The axial spacing of the balloons 16, 26 enable the stabilizing balloon 26 to engage the bladder wall to provide a sufficient radial force thereon for securing/mounting the catheter within the bladder without interfering with the function of balloon 16.

Figure 3:
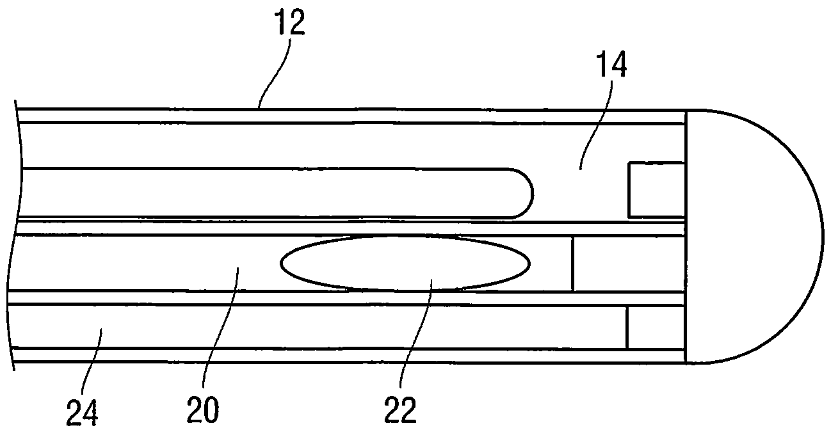
FIG. 3 is a close-up view of the tip of the catheter of FIG. 1A.
Figure 4:
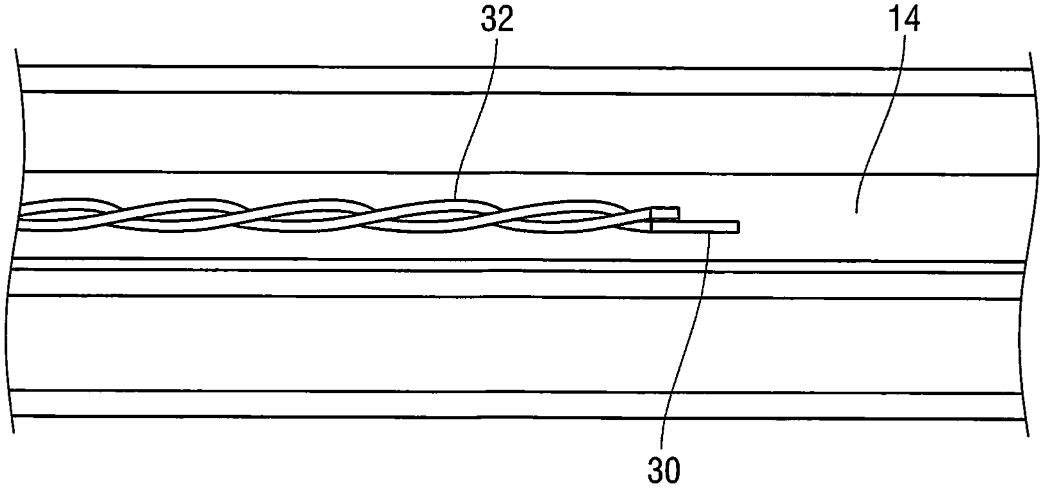
FIG. 4 is a close-up view of the sensor of FIG. 1A within the air lumen.
Figure 7:
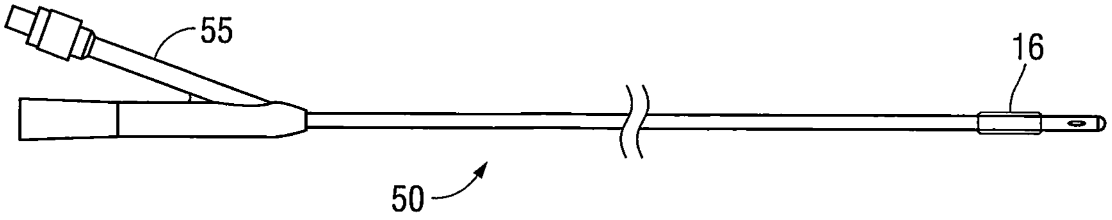
FIG. 7 is a side view of an alternate embodiment of the catheter of the present invention similar to FIG. 1A except having a single balloon, the balloon shown in the inflated condition.

It should be appreciated that although the stabilizing balloon is shown in the embodiment of FIG. 1, it is also contemplated as an alternative that the catheter and system of FIGS. 1 and 2 can be utilized without the stabilizing balloon 26 as shown for example in FIG. 7. Similarly, although the various embodiments (catheter) disclosed herein utilize a stabilizing balloon, it is also contemplated that alternatively the catheter of these various embodiments not include a stabilizing balloon. In the embodiment of FIG. 7, catheter 50 has two lumens: 1) a lumen for drainage of the bladder which has a side opening at a distal end to communicate with the bladder (similar to lumen 20 of FIG. 1A); and 2) an air lumen filling pressure balloon 16 via insertion of air through side port 55. The sensor 30 is positioned within the air lumen in the same manner as sensor 30 is in lumen 14 or in the alternative positions disclosed herein. Thus, the pressure and temperature sensing described in conjunction with FIG. 1 is fully applicable to the embodiment of FIG. 7. Besides the elimination of the stabilizing balloon and its lumen and side port, catheter 50 is the same as catheter 10, Note that although only one sensor is shown in FIG. 3, it is also contemplated that multiple sensors can be provided. Also, note that the sensor 30 is positioned in lumen 14 at a mid-portion of the balloon, i.e., just proximal where the opening in lumen 14 communicates with the interior 16*a* of the balloon 16. It is also contemplated that the sensor can be placed at another portion within the lumen 14, e.g., a more proximal portion, with respect to the lumen opening for the balloon. Also, the lumen opening for the balloon need not be at the mid portion of the balloon and can be at other regions of the balloon to communicate with the interior space 16*a*. Note if multiple sensors are provided, they can be positioned at various locations within the lumen 14.

As shown, the sensor 30 and its transmission wires are located in the same lumen 14 also used for initial inflation gas, e.g., air, for balloon 16 and for the air charged column. This minimizes the overall transverse cross-section (e.g., diameter) of the catheter 10 by minimizing the number of lumens since additional lumens require additional wall space of the catheter. However, it is also contemplated in an alternate embodiment that the sensor is in a dedicated lumen separate from the inflation lumen 14. This can be useful if a larger sensor or additional wires are utilized which would restrict the air lumen if provided therein. This is also useful if a specific sized lumen for the sensor and wires is desired to be different than the sized lumen for the air column. Provision of a separate lumen is shown in the cross-sectional view of FIG. 6 wherein in this alternate embodiment catheter 40 has four lumens: 1) lumen 42 for drainage of the bladder which has a side opening at a distal end to communicate with the bladder (similar to lumen 20 of FIG. 1); 2) lumen 44 for filling pressure balloon 16; 3) lumen 46 for filling stabilizing balloon 26; and 4) lumen 50 in which sensor 30 and its transmission wires 32 and temperature sensor wires 34 are contained. In all other respects catheter 40 is identical to catheter 10 and its balloons, air channel, sensor, etc. would perform the same function as catheter 10. Therefore, for brevity, further details of catheter 40 are not discussed herein as the discussion of catheter 10 and its components and function are fully applicable to the catheter 40 of the embodiment of FIG. 6. As noted above, the cross-sectional shapes of the lumens can be circular, oval, etc, or other symmetrical or asymmetrical shapes.

Turning now to the use of the catheter 10, the catheter 10 is inserted into the bladder. Note catheter 50 would be used in the same manner. The balloon 26 is inflated to secure the catheter 10 in place during the procedure by insertion of a fluid (liquid or gas) through side port 28 which is in fluid communication with lumen 24. The system is charged by inflation of the balloon 16, i.e., preferably partial inflation for the reasons discussed above, by insertion of air via a syringe through port 15 which is in fluid communication with lumen 14. As discussed above, the catheter 10 is a closed system with the balloon 16 sealed so that air inserted through lumen 14 and into balloon 16 cannot escape through balloon 16. Thus, a closed chamber is formed comprising the internal space 16*a* of the balloon 16 and the internal lumen 14 communicating with the internal space 16*a* of balloon 16. With the balloon 16 inflated, pressure monitoring can commence. When external pressure is applied to an outer surface 16*b* of the balloon 16, caused by outward abdominal pressure which applies pressure to the bladder wall and thus against the wall of balloon 16, the gas e.g., air, within the chamber is compressed. The sensor 30 at the distal end of lumen 14 provides continuous pressure readings, converted to an electrical signal by the transducer within the distal end of lumen 14, and then electrically communicates through wire(s) 32 extending through lumen 14, exiting through the proximal side port 15 and connected to an external monitor. Note the wire can terminate at the proximal end in a plug in connector which can be connected directly to the monitor or alternatively plugged into a converter to convert the signals from the transducer in the embodiments wherein the converter is interposed between the wires and monitor (see e.g., the system of FIG. 2) to provide the aforedescribed graphic display. Although, the system is capable of continuous pressure and temperature monitoring, it can also be adapted if desired for periodic monitoring so the pressure and/or temperature readings can be taken at intervals or on demand by the clinician.

In the embodiments wherein an indicator is provided, if the measured pressure exceeds a threshold value, and/or a change in pressure measurement exceeds a specific rate over a specific time period, the indicator would alert the clinician, e.g., via a visual indication or an audible indication that the threshold is exceeded. The indicator in some embodiments can include an audible or visual alarm (shown schematically in FIG. 2). In the embodiments having an indicator, the indicator can be provided on a proximal end of the catheter which extends out of the patient or the indicator can be part of an external component such as the monitor or a separate alarm system. A visual, audible, or other indicator can likewise be provided in any of the other embodiments disclosed herein to indicate if the measured temperature exceeds a predetermined value, and such indicator can include an alarm and can be part of the catheter or a separate component.

Figure 8A:
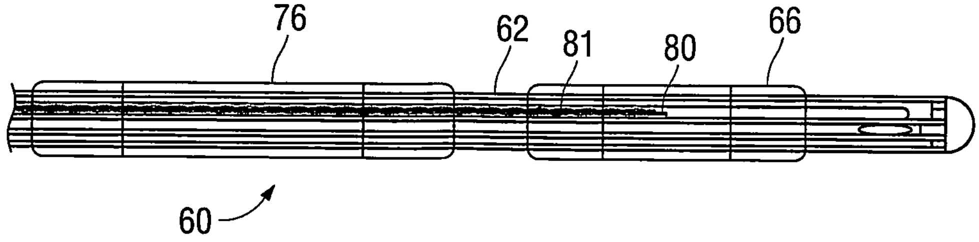
FIGS. 8A and 8B are side views of an alternate embodiment of the catheter of the present invention having two balloons and a pressure sensor and a separate temperature sensor in the air lumen, the two balloons shown in the deflated condition, with FIG. 8A showing the distal end and FIG. 8B showing the proximal end of the catheter.

In the embodiments of FIGS. 1-7, within the distal end of the air lumen 14 is a pressure transducer and pressure sensor 30 which also includes a temperature sensor. In the alternate embodiment of FIGS. 8A-10B, the temperature sensor is separate from the pressure sensor. More specifically, catheter 60 has an elongated flexible shaft 62 having a lumen (channel) 64 extending within the shaft 62 and fluidly communicating at a distal region with balloon 66 to inflate the balloon. Balloon 66 (also referred to as the pressure balloon) is utilized for monitoring pressure. A fluid side port 65 is positioned at a proximal region 67 of the catheter 60 for communication with an infusion source for infusion of gas e.g., air, through the lumen 64 and into the balloon 66. The catheter 60 is shown in FIG. 8A with balloon 66 in the deflated condition (position) and in FIG. 9 with the balloon 66 in the inflated condition (position). The shaft 62 also includes a second lumen (channel) 70 and third lumen (channel) 74 extending therein. The second lumen 70 is preferably the largest lumen and is configured for drainage of the bladder. Second lumen 70 has a side opening 72 at a distal portion communicating with the bladder. The third lumen 74 communicates at a distal region with stabilizing balloon 76 to fluidly communicate with balloon 76 to inflate the balloon. The stabilizing balloon 76 is inflatable to stabilize the catheter 60 to limit movement of the catheter 60 to keep it in place within the bladder. A side fluid port 75 is positioned at a proximal region 67 of the catheter 60 for communication with an infusion source for infusion of fluid through the lumen 74 and into the balloon 76.

Figure 9:
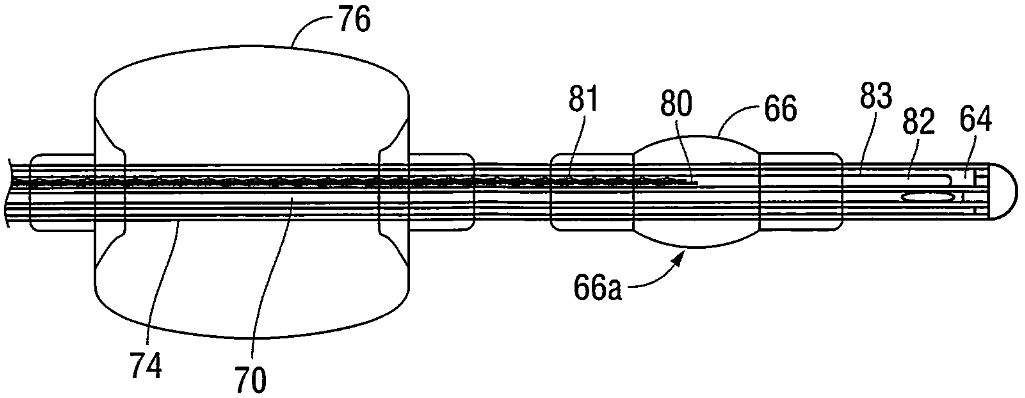
FIG. 9 is a side view similar to FIG. 8A showing the two balloons in the inflated condition.
Figure 10A:
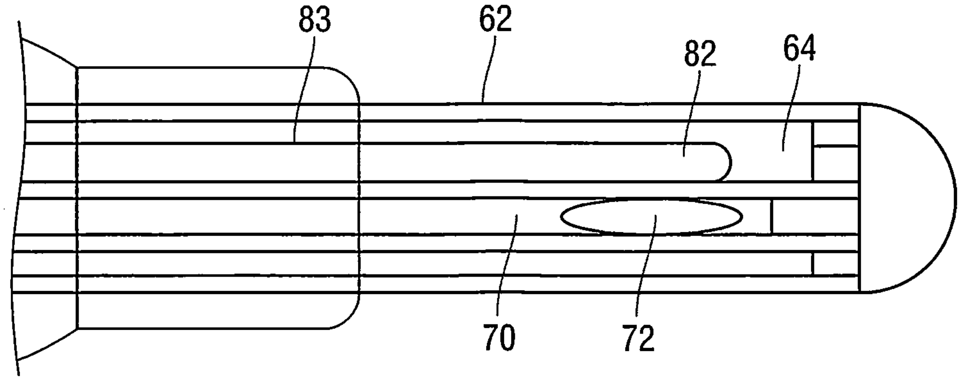
FIG. 10A is a close up view of the distal portion of the catheter of FIG. 8A.
Figure 10B:
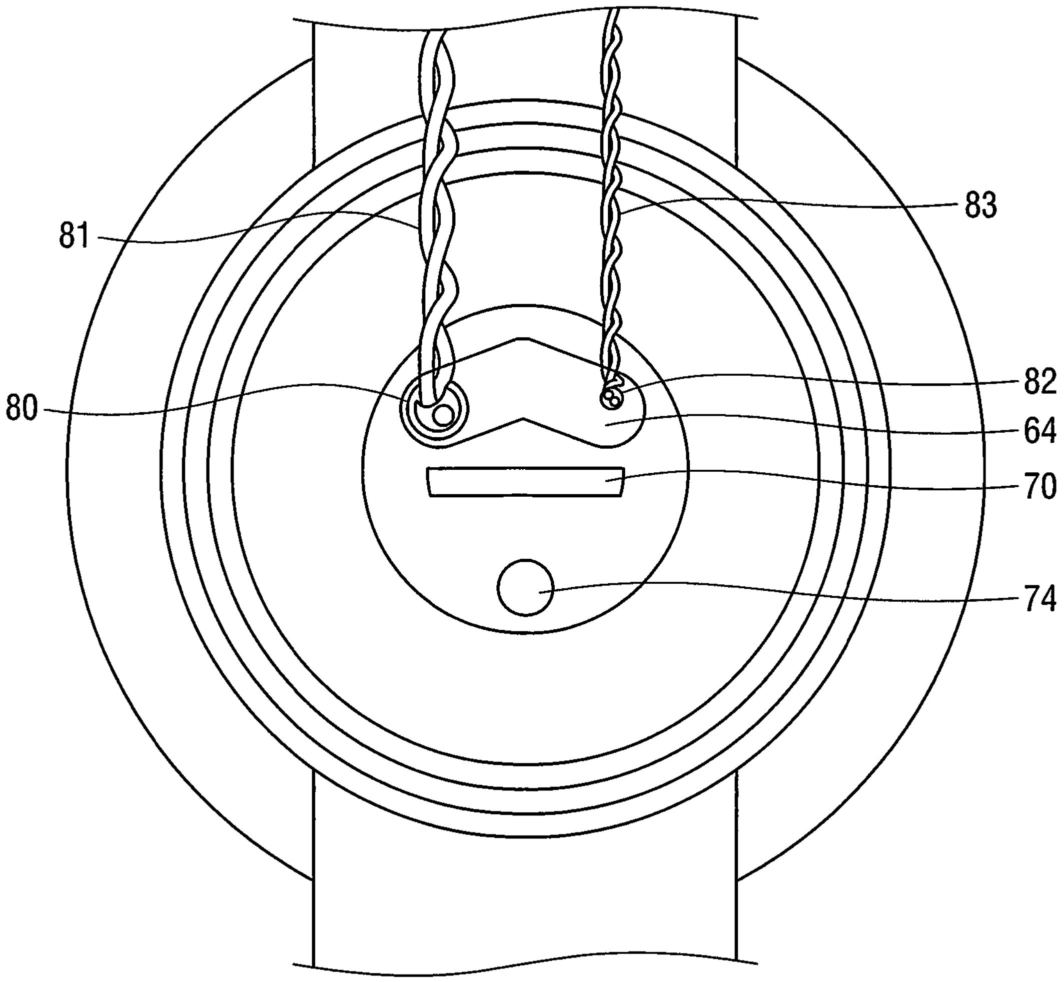
FIG. 10B is an enlarged transverse cross-sectional view of the catheter of FIG. 8A.

Sensor 80 is positioned in lumen 64 for sensing pressure in response to balloon deformation in the same manner as sensor 30. Sensor 82 is positioned in lumen 64 distal of sensor 80 for measuring core temperature. Temperature sensor 82 can be a thermocouple, a thermistor or other types of temperature sensors. As shown in FIG. 9, the temperature sensor is distal of the balloon 66 and its transmission wire(s) 83 extend proximally within lumen 64, exiting a proximal end (through side port 65) for communication with a monitor or alternatively a converter which communicates with the monitor. Wire(s) 81 of sensor 80 also extends through lumen 64, alongside wire 83, exiting through the side port 65 or a proximal end wall or a side wall of the lumen. It is also contemplated that alternatively one or both of sensors 80 and 82, and their associated wires 81, 83, can be positioned in a separate "fourth" lumen such as in the embodiment of FIG. 6 so that the "inflation lumen" and the "sensor lumen" are independent.

In use, catheter 60 is inserted into the bladder and stabilizing balloon 76 is inflated to secure the catheter 60 in place. The system is charged by inflation of the balloon 66, i.e., preferably partially inflated for the reasons discussed above, by insertion of gas, e.g., air, through port 65 which is in fluid communication with lumen 64 in a closed system formed by the internal space 66*a* of the balloon 66 and the internal lumen 64 communicating with the internal space 66*a* of balloon 66. With the balloon 66 inflated, pressure monitoring can commence as external pressure applied to an outer surface of the balloon 66 compresses the gas within the gas containing chamber. The sensor 80 at the distal end of lumen 64 provides continuous pressure readings, converted to an electrical signal by the transducer within the distal end of lumen, and then electrically communicates through wires 82 extending through lumen 64 to an external monitor either directly or via a converter. The sensor 82 at the distal end of lumen 64 provides continuous temperature readings via wires 83 communicating directly or indirectly with the monitor, Although, the system is capable of continuous pressure and continuous temperature monitoring, as with the other systems disclosed herein, it can also be adapted if desired for periodic monitoring so the pressure and/or temperature readings can be taken at intervals or on demand by the clinician.

Figure 8B:
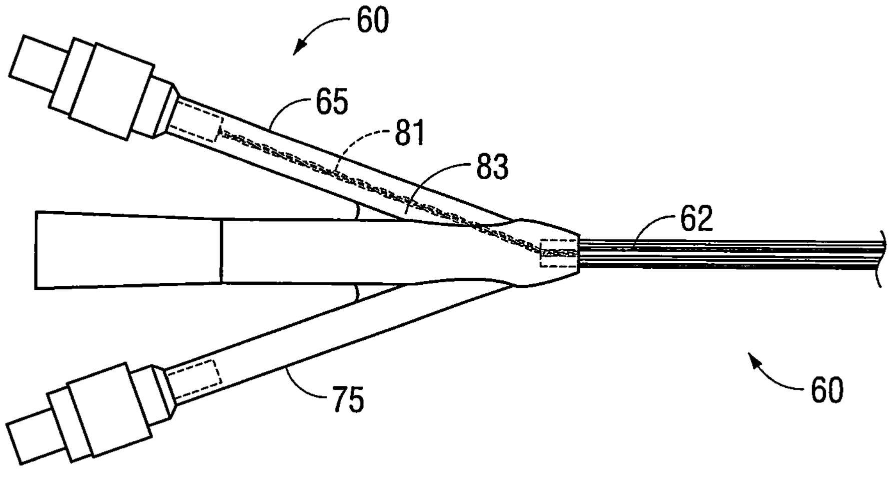
Figure 11:
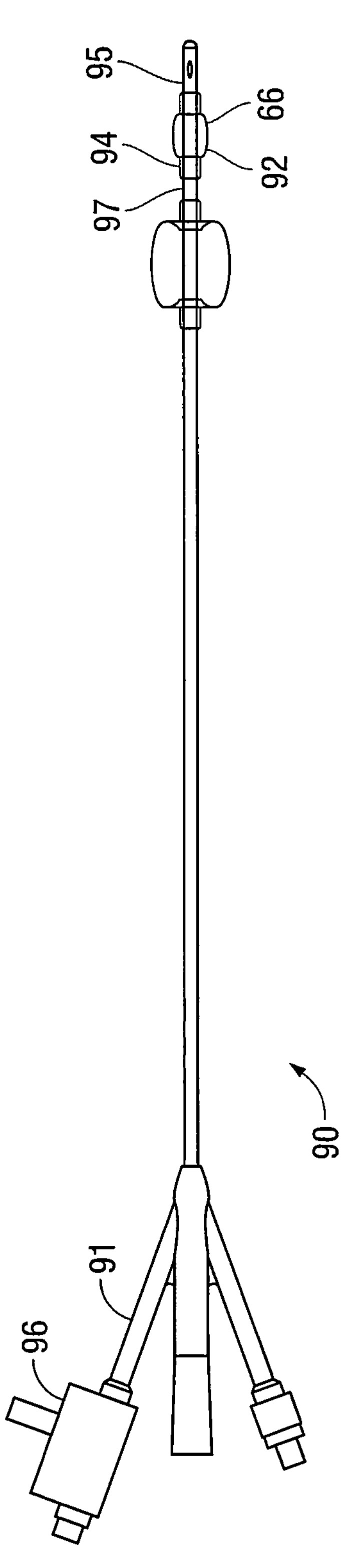
FIG. 11 is a side view of another alternate embodiment of the catheter of the present invention having two balloons, a sensor in the air lumen and an external transducer, the two balloons shown in the inflated condition.

In the alternative embodiment of FIG. 11, catheter 90 is identical to the catheter 60 of FIG. 8 except that the pressure transducer is positioned external of the catheter rather than in the air (or other gas) lumen. That is, instead of the pressure transducer including the sensor being positioned within the distal end of the air lumen, the pressure sensor 92 is positioned within lumen 94 at the distal end of the lumen and transmission wire(s) 93 connect the sensor 92 to the pressure transducer 96 positioned outside of the patient at a proximal region of catheter 90. As shown, the pressure transducer 96 can be positioned in a side port of catheter 90. In alternate embodiments, it is positioned outside the catheter. In alternate embodiments, the pressure sensor acts as a transducer and is positioned outside the patient at a proximal region of the catheter or alternatively positioned in a side port. The temperature sensor 95 is positioned within lumen 94 along with transmission wire 97 in the same manner as temperature 82 and wires 83 are positioned in catheter 60 described above. The temperature sensor 95 can be a separate sensor positioned distal of the pressure sensor 92 as shown or alternatively it can be part of sensor 92 as in the embodiment of FIG. 1. In all other respects, catheter 90 is identical to catheter 60 and therefore for brevity further discussion is not provided since the structure and function of the balloons, the continuous pressure monitoring, etc., as well as the aforedescribed alternative arrangements of catheter 60, are fully applicable to the catheter 90.

Figure 12:
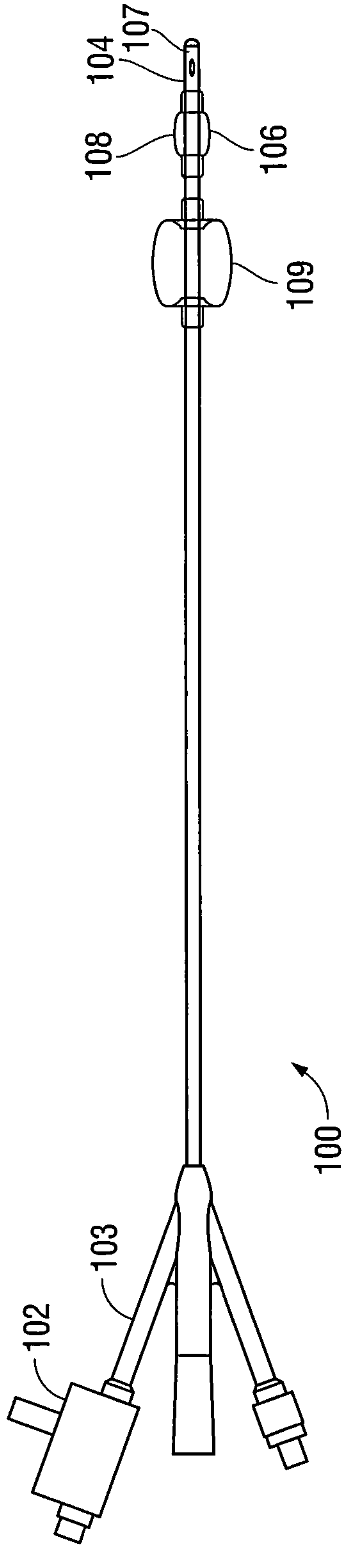
FIG. 12 is a side view of another alternate embodiment of the catheter of the present invention having two balloons, a temperature sensor in the air lumen and the pressure sensor external of the catheter, the two balloons shown in the inflated condition.

In the alternative embodiment of FIG. 12, catheter 100 is identical to catheter 60 of FIG. 8 except that the pressure transducer and pressure sensor are positioned external of the patient at a proximal region of the catheter rather than in the air lumen. That is, instead of the pressure transducer/sensor being positioned within and at the distal end of the air lumen, the transducer/pressure sensor 102 are positioned at a side port 103 of the catheter 100. In alternative embodiments, they are positioned outside the catheter. In yet other embodiments, the pressure sensor/pressure transducer can be positioned within the air (or other gas) lumen at a proximal end of the air lumen. The temperature sensor 107 is positioned within lumen 104 along with transmission wire(s) 108 in the same manner as temperature sensor 82 and wire 83 are positioned in catheter 60 described above. The system is charged by inflation of the balloon 106, i.e., preferably partially inflated for the reasons discussed above, by insertion of air via a syringe or other injection device through the side port 103 which is in fluid communication with lumen 104. The catheter 100 is a closed system with the balloon 106 sealed so that air inserted through lumen 104 and into balloon 106 cannot escape through balloon 106. Thus, a closed chamber is formed comprising the internal space of the balloon 106 and the internal lumen 104 communicating with the internal space of balloon 106. With the balloon 106 inflated, pressure monitoring can commence. When external pressure is applied to an outer surface of the balloon 106, caused by outward abdominal pressure which applies pressure to the bladder wall and thus against the wall of balloon 16, the gas (e.g., air) within the chamber of the balloon 106 is compressed. This compresses the air within the lumen 104 creating an air charged column along the lumen 104. The sensor 102 at the proximal end of catheter 100 measures pressure of the air column at its proximal end and can provide continuous pressure readings, converted to an electrical signal by the transducer at the proximal end or external of the catheter 100, and then electrically communicates through wire(s) to an external monitor. The balloon 106, like balloon 16, balloon 66 and the other pressure balloons described herein, is of sufficiently large size to provide a sufficient circumferential area for detection of pressure changes along several parts of the bladder wall, thereby providing an average pressure and enabling more accurate pressure readings. Balloon 109 is a stabilizing balloon like balloon 76 inflated through a separate lumen.

Note the wire(s) of the sensor 102 can terminate at the proximal end in a plug in connector which can be connected directly to the monitor or alternatively plugged into a converter to convert the signals from the transducer in the embodiments where the converter is interposed between the wires and monitor (see e.g, the system of FIG. 2) to provide the aforedescribed graphic display. Although, the system is capable of continuous pressure and temperature monitoring, it can also be adapted if desired for periodic monitoring so the pressure and/or temperature readings can be taken at intervals or on demand by the clinician. In all other respects, catheter 100 is identical to catheter 60 and therefore for brevity further discussion is not provided since the structure and function of the balloons, the continuous pressure monitoring, etc., as well as the aforedescribed alternative arrangements of catheter 60, are fully applicable to the catheter 100.

Figure 13A:
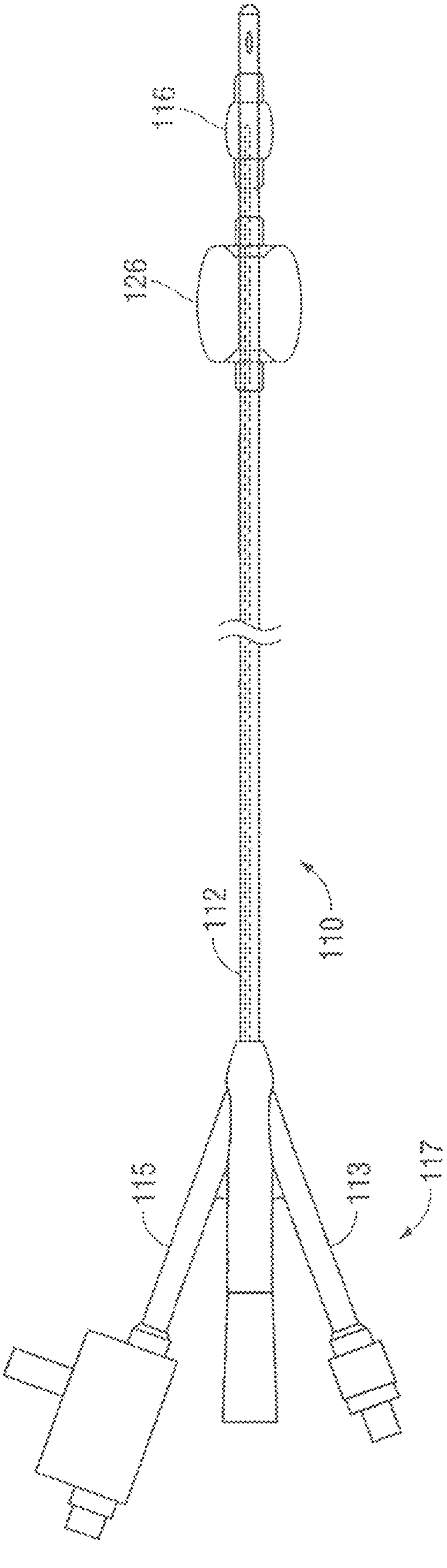
FIG. 13A is a side view of another alternate embodiment of the catheter of the present invention having two balloons and a pressure sensor positioned within the pressure balloon, the two balloons shown in the inflated condition and also showing an optional oxygen sensor.
Figure 13B:
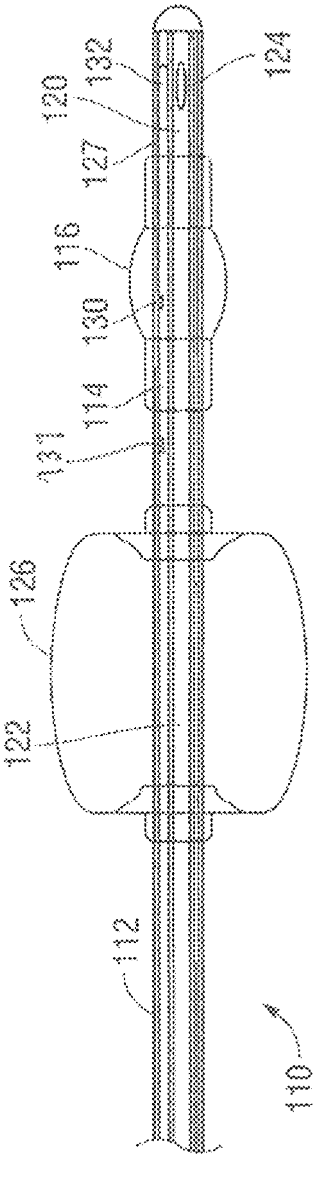
FIG. 13B is an enlarged view of the distal portion of the catheter of FIG. 13A.

FIGS. 13A and 13B illustrate an alternate embodiment wherein catheter 110 includes a pressure sensor within the balloon. More specifically, catheter 110 has an elongated flexible shaft 112 having a lumen (channel) 114 extending within the shaft 112 and communicating at its distal region with balloon 116 to fluidly communicate with balloon 116 to inflate the balloon. Balloon 116 (also referred to as the pressure balloon) is utilized for monitoring pressure. A fluid side port 115 is positioned at a proximal region 117 of the catheter 110 for communication with an infusion source for infusion of gas through the lumen 114 and into the balloon 116. The shaft 112 also includes a second lumen (channel) 120 and third lumen (channel) 122 extending therein. Second lumen 120 has a side opening 124 at a distal portion communicating with the bladder. The third lumen 122 communicates at a distal region with stabilizing balloon 126 to fluidly communicate with balloon 126 to inflate the balloon to limit movement of the catheter 110 to keep it in place within the bladder for drainage. A fluid port 113 is positioned at a proximal region 117 of the catheter 110 for communication with an infusion source for infusion of fluid through the lumen 122 and into the balloon 126.

The pressure sensor 130 is carried by catheter 110 and positioned within the balloon 116 to measure pressure in response to deformation of the balloon in response to pressure exerted on an outer wall of balloon 116. The pressure transducer can include the sensor 130 or can be a separate component positioned at a proximal end of the catheter external of the catheter 110. The temperature sensor 132 can be positioned within the balloon 116, can be part of sensor 130, or alternatively positioned within lumen 114 (as shown in FIG. 13B), with its transmission wire(s) 127 extending within the gas, e.g., air, lumen 114 along with the wires of sensor 130 in the same manner as in catheter 60 described above. An oxygen sensor 131 can be provided.

In all other respects, catheter 110 is identical to catheter 60 and therefore for brevity further discussion is not provided since the structure and function of the balloons, lumens, continuous pressure monitoring, etc. as well as the aforedescribed alternative arrangements of catheter 60, are fully applicable to the catheter 110.

Figure 15:
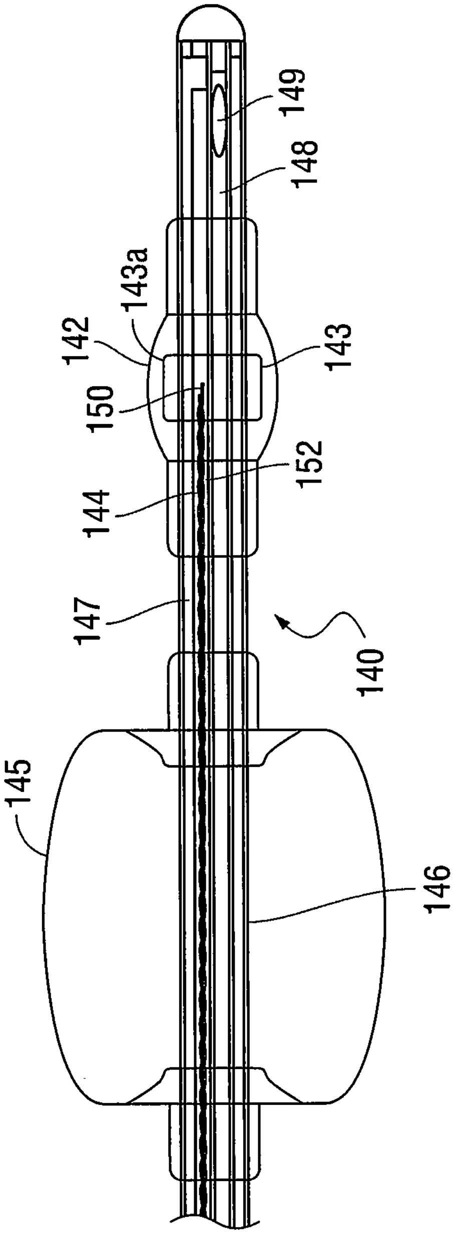
FIG. 15 is a side view of another alternate embodiment of the catheter of the present invention having an outer and inner pressure balloon and a stabilizing balloon, the balloons shown in the inflated condition.

As discussed above, the pressure balloons disclosed herein have a large circumferential area (and large volume) to provide multiple reference points for pressure readings and to provide an average pressure to enable more accurate readings. Thus, the pressure balloon provides for gross measurement. In an alternate embodiment shown in FIG. 15, the pressure balloon for detecting pressure, designated by reference numeral 142, forms an outer balloon of catheter 140. Contained within the outer balloon 142 is an inner balloon 143. The inner balloon 143 provides a smaller diameter balloon and a smaller circumference (and volume) than the outer balloon 14. The inner balloon 143 together with the lumen 144 forms a smaller gas, e.g., air, column than in the embodiments discussed above where the larger balloon internal space communicates directly with the air lumen. This provides finer measurements. Thus, the compliant outer balloon 142 compresses the compliant inner balloon 143 which compresses the air within air lumen 144. The closed system is thereby formed by the internal space of the inner balloon 143 and the lumen 144. In certain instances, the smaller balloon air column can provide a more accurate reading from the average pressure determined by the larger outer balloon 142. Several embodiments of the inner/outer balloon arrangement are discussed herein.

The inner balloon 143 and outer balloon 142 can be separately/independently inflated and closed with respect to each other so there is no communication, e.g. passage of gas or liquid, between the inner and outer balloons 143, 142.

In the embodiments disclosed herein having inner and outer balloons, the outer balloon acts a medium of transmission to the inner pressure balloon. That is, as the outer balloon is deformed, the fluid within the outer balloon acts against the outer wall of the inner balloon to deform the inner balloon and pressurize the gas, e.g., air, within the chamber of the inner balloon for pressure measurement. With the outer balloon functioning as a transmission medium, the bladder (or other body cavity in which the catheter is inserted) does not need to be filled with fluid. Thus, the catheter can be used in a voided cavity, e.g., without interstitial fluid. The radial spacing between the wall of the outer balloon and wall of the inner balloon provides space for transmission of the fluid within the outer balloon to deform the inner balloon. The spacing can be achieved in various ways which are described below and include for example, radial separation, a chamber interposed between the inner and outer balloons, a wall of the catheter interposed between the inner and outer balloons, etc. The advantages of not requiring insertion of fluid during pressure measurement are discussed below.

The pressure transducer and pressure sensor 150 can be positioned within the lumen 144 in the same manner as sensor 30 of FIG. 1 and can function in the same manner. Alternatively, the pressure transducer can be at a proximal end of the catheter 140 as in the embodiment of FIG. 12 or external of the catheter. A temperature sensor can be part of sensor 150 as in the embodiment of FIG. 1 or alternatively it can be a separate component which can be positioned for example distal of the pressure sensor within the gas, i.e., air, lumen as in the embodiment of FIG. 8A. The transmission wires of the pressure sensor 150 and the temperature sensor extend through lumen 144 or alternatively positioned in a separate lumen.

The catheter 140 can optionally include a stabilizing balloon 145 similar to balloon 76 of FIG. 8. The catheter 140 would have a lumen, e.g., lumen 146, to inflate the stabilizing balloon 145. Lumen 148 with side opening 149 provides for drainage of the bladder. Lumen 144 which is used to inflate the inner balloon 143 and create the gas column has an opening at a distal region to communicate with inner balloon 143. A separate lumen 147 has an opening at a distal region to communicate with the outer balloon 142 to fill the outer balloon 142.

In use, catheter 140 is inserted into the bladder and stabilizing balloon 145 is inflated to secure the catheter 140 in place. The system is charged by inflation of the inner balloon 143, i.e., preferably partially inflated for the reasons discussed above, by insertion of air through a side port which is in fluid communication with lumen 144 in a closed system formed by the internal space 143*a* of the inner balloon 143 and the internal lumen 144 communicating with the internal space of inner balloon 143. Outer balloon 142 is filled, i.e., preferably partially inflated for the reasons discussed above, via injection of air through a separate lumen. With the outer balloon 142 inflated, pressure monitoring can commence as external pressure applied to the larger circumferential outer surface of the outer balloon 142 compresses and deforms the outer balloon 142 which compresses the inner balloon 143 as fluid presses the outer wall of the inner balloon. As the inner balloon 143 is compressed and deformed in response to compression/deformation of the outer balloon 142 based on changes to bladder pressure, the sensor 150 at the distal end of lumen 144 provides continuous pressure readings, converted to an electrical signal by the transducer within the distal end of lumen 144, and then electrically communicates through wires 152 extending through lumen 144 to an external monitor either directly or via a converter. Although, the system is capable of continuous pressure and continuous temperature monitoring, as in the other embodiments disclosed herein it can also be adapted if desired for periodic monitoring so the pressure and/or temperature readings can be taken at intervals or on demand by the clinician. Note fluid does not need to be present in the cavity to achieve the pressure readings.

Note that although separate lumens are provided for the inflation of inner balloon 143 and outer balloon 142, in an alternate embodiment, a single lumen can be utilized to inflate both balloons 143 and 142.

Figure 16:
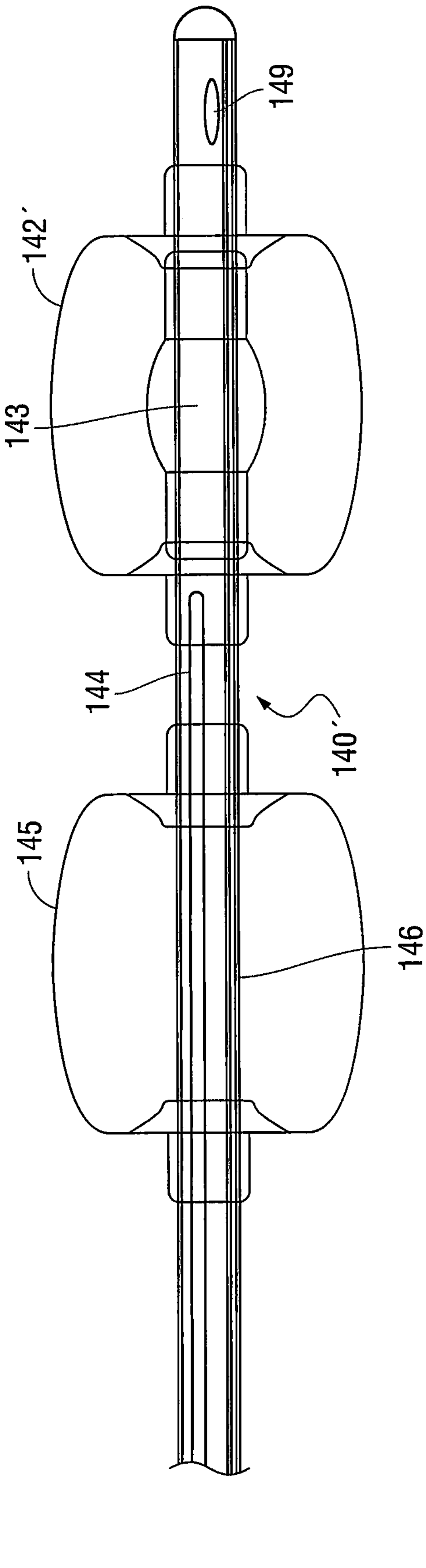
FIG. 16 is a side view similar to FIG. 15 illustrating an alternate embodiment having a larger outer balloon.

FIG. 16 illustrates an alternate embodiment of catheter 140, designated by reference numeral 140'. Catheter 140' is identical to catheter 140 except a larger outer balloon 142' is provided to cover more surface area for pressure readings. In all other respects, catheter 140' is identical to catheter 140 and for brevity further discussion is not provided since the features and functions of catheter 140, and its alternatives such as single or two lumens for inner and outer balloon inflation, are fully applicable to catheter 140'. For ease of understanding, the components of catheter 140' which are identical to catheter 140 are given the same reference numerals as catheter 140.

Note that the larger balloon 142' can be used with the catheters of any of the embodiments described herein. Thus, a pressure balloon of the larger size balloon 142' can be used instead of the smaller pressure balloons illustrated in the drawings. Note the size of the balloons is provided by way of example and are not necessarily drawn to scale comparatively to the other components.

Figure 17A:
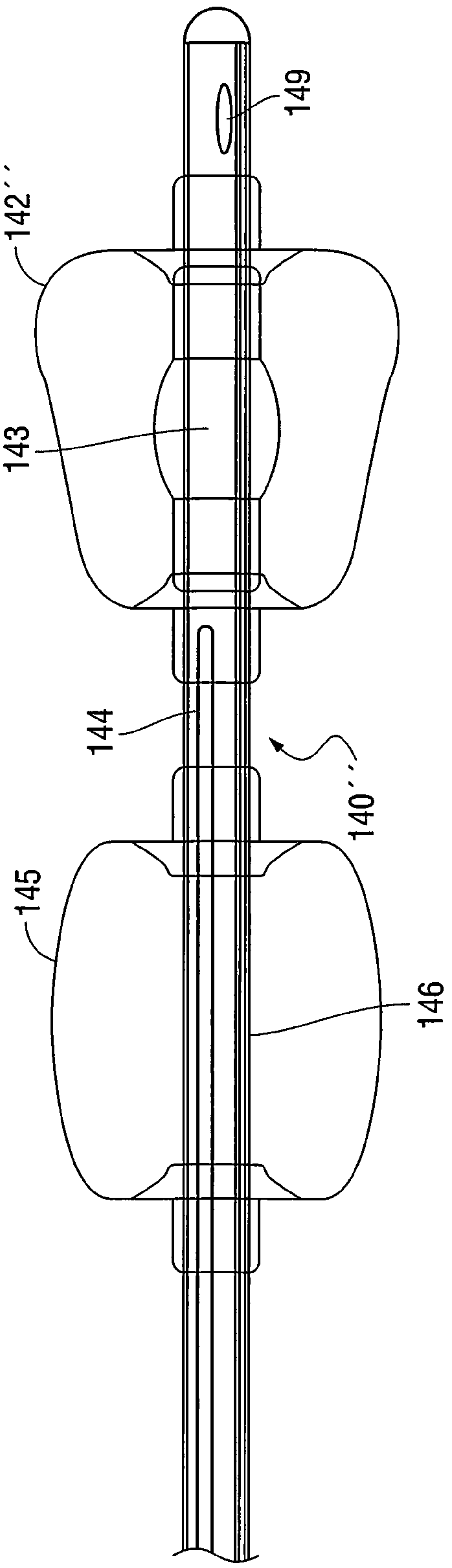
FIG. 17A is a side view similar to FIG. 15 illustrating an alternate embodiment having a pear-shaped outer balloon.
Figure 17B:
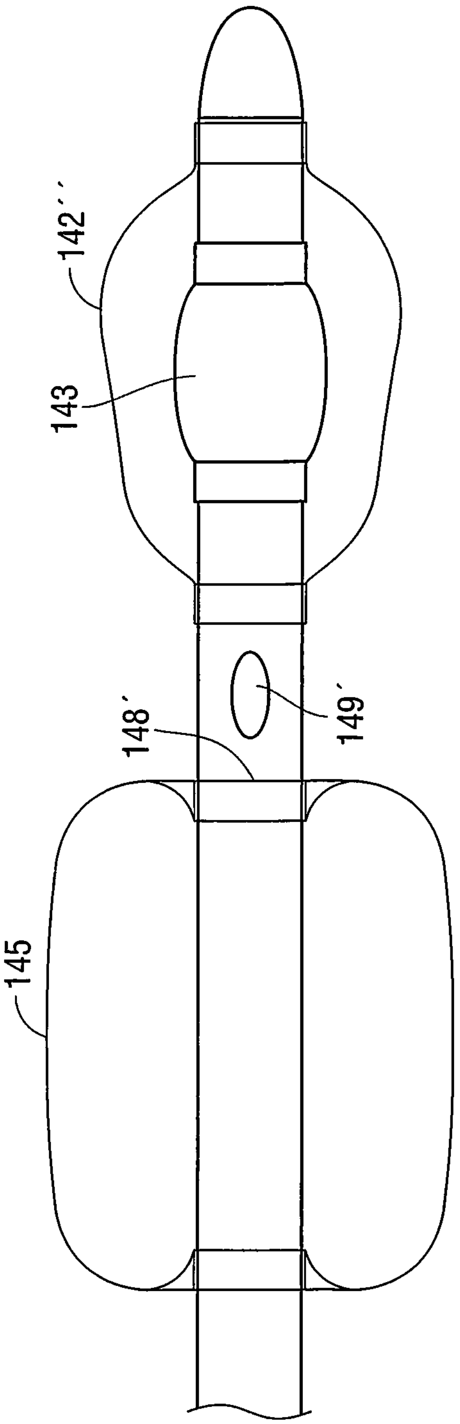
FIG. 17B is a side view similar to FIG. 17A showing an alternate embodiment wherein the drainage opening is between the two balloons and showing an alternate shaped outer balloon.

FIG. 17A illustrates an alternate embodiment of catheter 140, designated by reference numeral 140". Catheter 140" is identical to catheter 140 except a pear shaped larger outer balloon 142" is provided. The larger balloon 142" covers more surface area for pressure readings. The pear shape could in certain applications decrease the risk of obstructing the ureter and provide more tactile continuity of the balloon to the bladder wall giving a better transmission of abdominal pressure to the internal sensor. In all other respects, catheter 140" is identical to catheter 140 and for brevity further discussion is not provided since the features and functions of catheter 140, and its alternatives such as single or two lumens for inner and outer balloon inflation, are fully applicable to catheter 140". For ease of understanding, the components of catheter 140" which are identical to catheter 140 are given the same reference numerals as catheter 140. FIG. 17B illustrates a catheter identical to catheter 140" with identical balloons, the only difference being that the side opening 149' is positioned proximal of the balloon 143 rather than distal of the balloon as in FIG. 17A. That is, opening 149', in communication with the catheter lumen 148' for drainage of the bladder, is positioned between the stabilizing balloon 145 and the outer pressure (and inner)

pressure balloon 142" (and 143). Thus, it is distal of the stabilizing balloon 145 and proximal of the outer balloon 142".

Note that the positioning of the side opening for drainage of FIG. 17B, which communicates with the drainage lumen of the catheter, can be utilized with any of the catheters disclosed herein. Thus, in the catheters disclosed in the various embodiments herein, instead of the drainage opening positioned distal of the pressure balloon(s), it can be proximal of the pressure balloon and distal of the stabilizing balloon so it is between the two balloons.

Note that the pear shaped balloon 142" can be used with the catheters of any of the embodiments described herein. Thus, a pressure balloon of the pear shape of balloon 142", and of larger or smaller size if desirable, can be used instead of the pressure balloons illustrated in the drawings.

FIGS. 18-25B illustrate an alternate embodiment of the catheter of the present invention. The pressure balloon for detecting pressure, designated by reference numeral 202, forms an outer balloon of catheter 200. Contained within the outer balloon 202 is an inner balloon 204. The inner balloon 204 provides a smaller diameter balloon and a smaller circumference (and volume) than the outer balloon 202. The inner balloon 204 together with the lumen 214, which communicates with the inner balloon 204 for inflation thereof, forms a smaller gas, e.g., air, column as in the embodiments of FIGS. 15-17. This provides finer measurements. Thus, the compliant outer balloon 202 fluid or wall compresses the outer wall 205 of the compliant inner balloon 204 which compresses the air (or other gas) within air lumen 214. The closed system is thereby formed by the internal space 204*a* of the inner balloon 204 and the lumen 214. The smaller balloon air column can in certain instances provide a more accurate reading from the average pressure determined by the larger outer balloon 202.

Figure 18A:
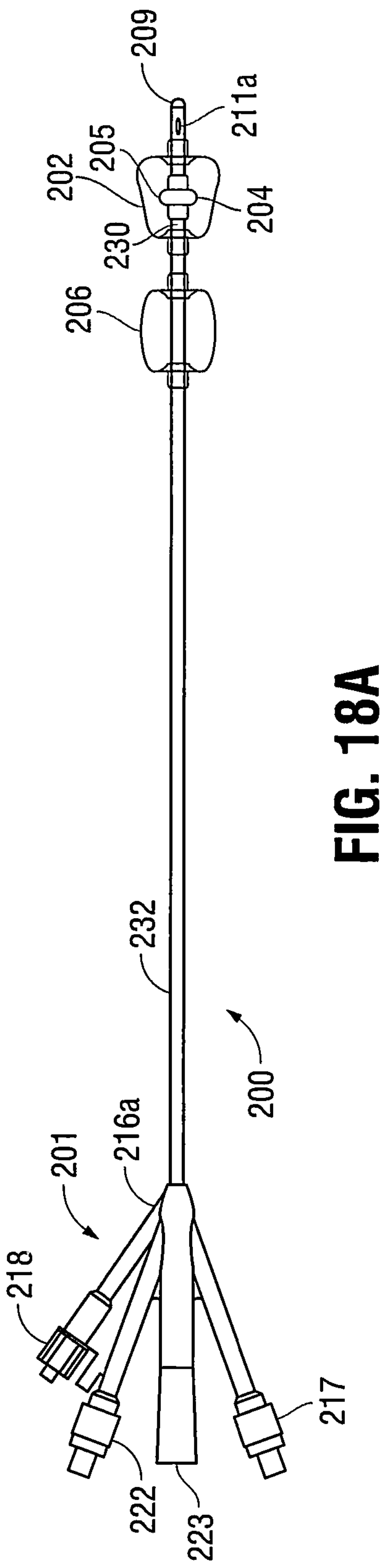
FIG. 18A is a side view of another alternate embodiment of the catheter of the present invention having a port for connection to an external pressure transducer and an outer and inner pressure balloon, the two balloons shown in the inflated condition.
Figure 18B:
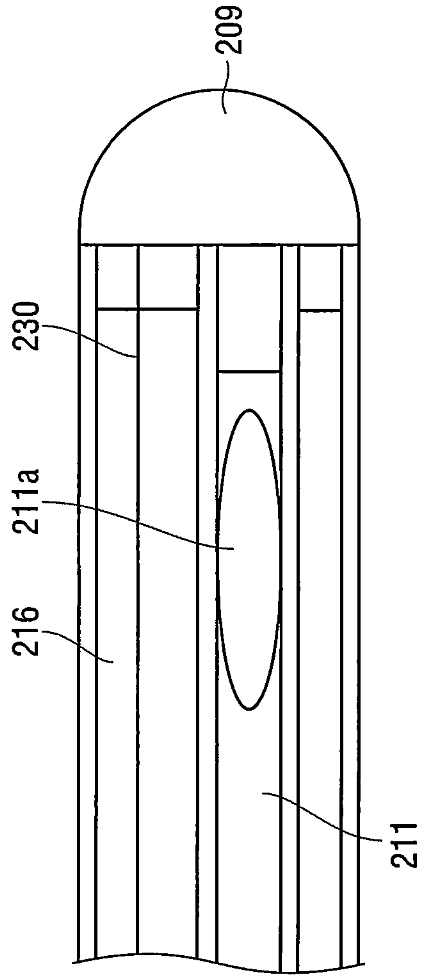
FIG. 18B is close up view of the distal end of the catheter of FIG. 18A.
Figure 19:
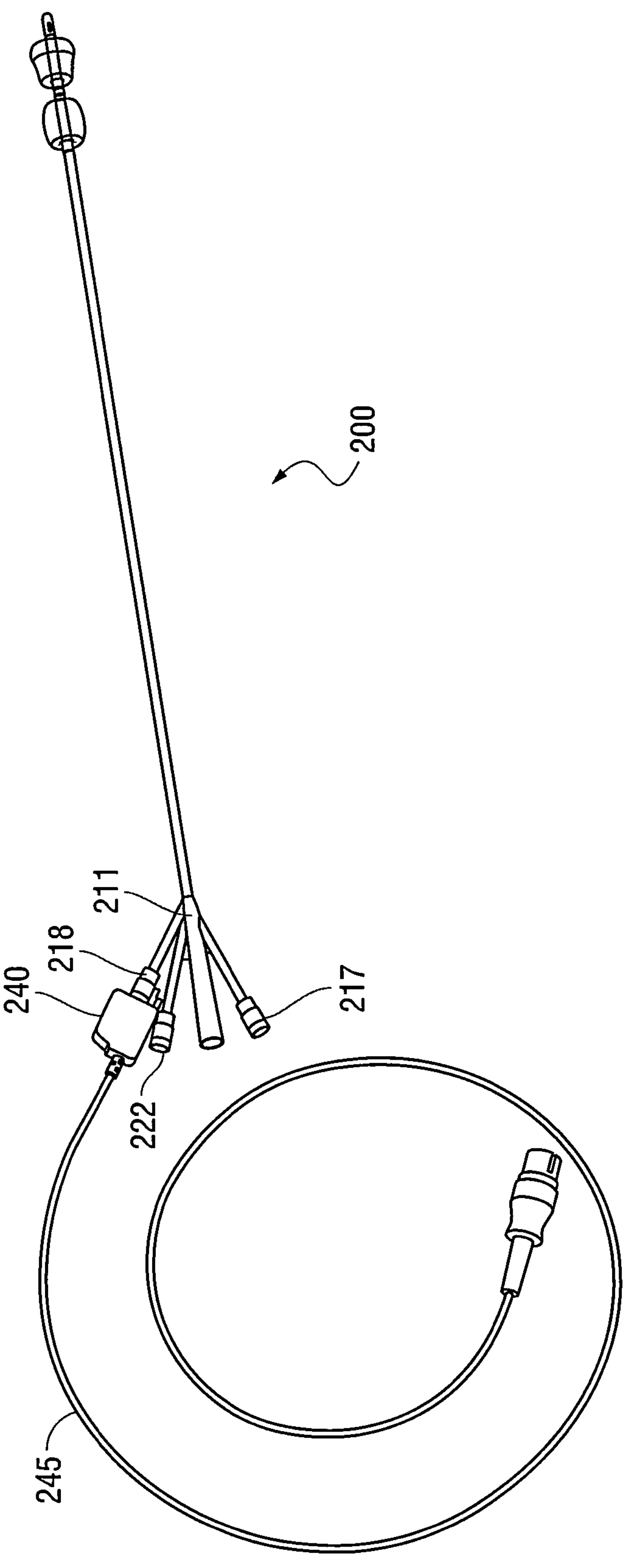
FIG. 19 is a perspective view of the catheter of FIG. 18A with a pressure transducer hub attached to the catheter.

The pressure transducer and pressure sensor are external to catheter 200 and mounted to port 218 at the proximal end 201 of catheter 200. More specifically, a transducer hub or housing, designated generally by reference numeral 240, contains the sensor and pressure transducer and is mounted to the angled side port 218. In the embodiment of FIG. 18A, the hub 240 is mounted over the port 218 and can be locked or secured thereto such as by a friction fit, snap fit, threaded attachment, a latch, etc., maintaining an airtight seal so the air is contained within the lumen 214 and balloon 204. The hub 240 has an elongated (rod-like) member or nose 242 extending distally therefrom (FIG. 24A) dimensioned to be inserted through the proximal opening in port 218 and into air lumen 214. (Note the air lumen 214 as in the other lumens extend into their respective angled side ports). The elongated member 242 also has a channel 244 extending therethrough to allow the pressure wave to travel through to the pressure sensor. Although in preferred embodiments no additional air needs to be injected into inner balloon 204 via lumen 214 after attachment of hub 240, it is also contemplated that a port or opening can be provided in hub 240 to receive an injection device for injection of additional air. Such additional air can communicate with and flow through channel 244 of elongated member 242, into lumen 214 and into inner balloon 204 for inflation, or alternatively, a side port or opening in angled port downstream of the elongated member 242 could be provided.

To charge the system, when the hub 240 is mounted to the side port 218, the elongated member 242 extends into lumen 214 to advance air through the air lumen 214 into inner balloon 204 to expand inner balloon 204. In some embodiments, 2 cc of air can be displaced/advanced by the member 242, although other volumes are also contemplated. Thus, as can be appreciated, mounting of the hub 240 to the catheter 200 automatically pressurizes the air lumen/chamber and expands the inner balloon 204. Note the inner balloon 204 can be partially or fully inflated (expanded), dependent on the amount of air advanced into the inner balloon 204. Further note that the lumen 214 is not vented to atmosphere when the transducer hub 240 is attached and air is advanced through the air lumen. The port 218 can include a closable seal through which the elongated member 242 is inserted but maintains the seal when the elongated member 242 remains in the lumen 214. This maintains a closed system.

Lumen 214 which is used to inflate the inner balloon 204 and create the air column has an opening at a distal region to communicate with the interior of inner balloon 204. Lumen 212 of catheter 200 has an opening at a distal region to communicate with the outer balloon 202 to fill the outer balloon 202. Angled port (extension) 222 at the proximal end of catheter 200 receives an inflation device to inflate, either fully or partially, the outer balloon 202.

Note as in the other embodiments disclosed herein, air is described as the preferred gas for creating the column and expanding the balloon, however, other gasses are also contemplated, for each of the embodiments herein.

Figure 20A:
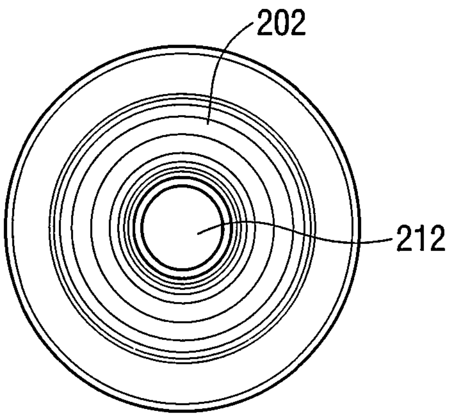
FIGS. 20A, 20B and 20C are enlarged front, side and perspective views of the outer balloon of FIG. 18A in the expanded condition.
Figure 20B:
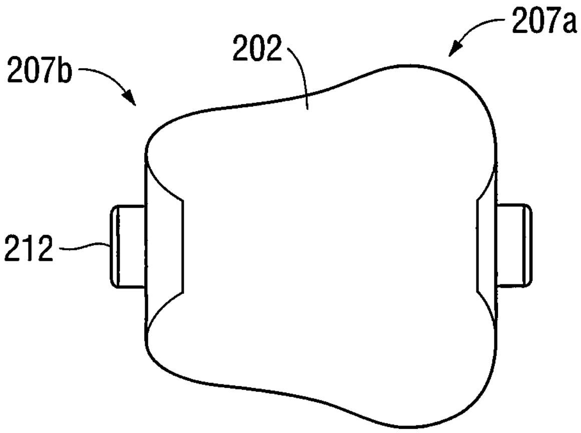
Figure 20C:
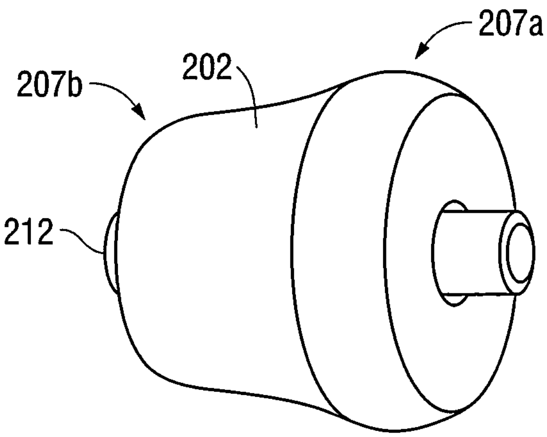
Figure 21A:
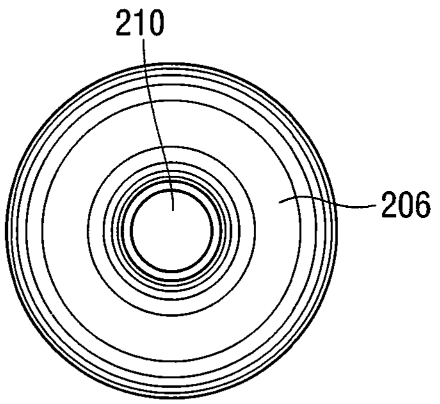
FIGS. 21A, 21B and 21C are enlarged front, side and perspective views of the stabilizing balloon of FIG. 18A in the expanded condition.
Figure 21B:
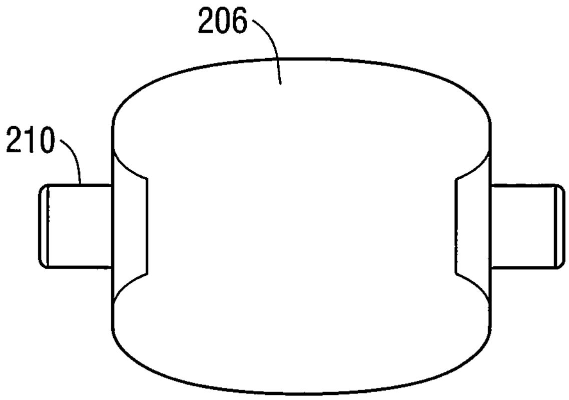
Figure 21C:
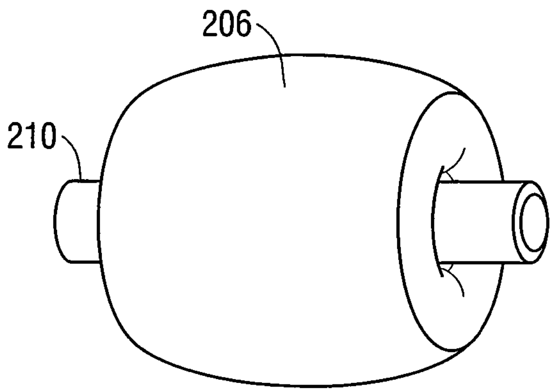
Figure 22A:
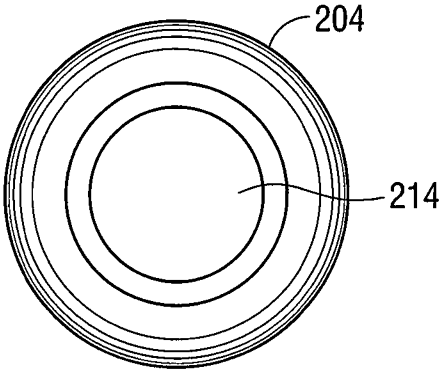
FIGS. 22A, 22B and 22C are enlarged front, side and perspective views of the inner balloon of FIG. 18A in the expanded condition.
Figure 22B:
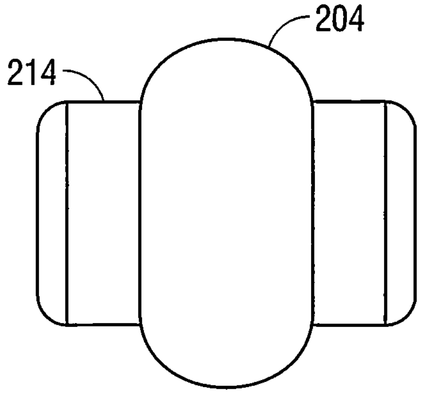
Figure 22C:
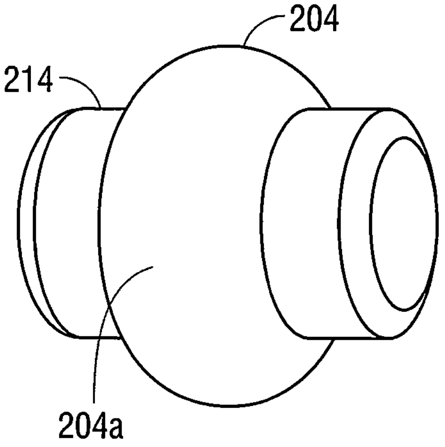

The outer balloon 202 can be shaped such that a distal region 207*a* (FIGS. 20A-20C) has an outer transverse cross-sectional dimension, e.g., diameter, greater than an outer transverse cross-sectional dimension, e.g., diameter, of the proximal region 207*b*. A smooth transition (taper) can be provided between the distal region 207*a* and proximal region 207*b*. Note the balloon 202 can be pear shaped as shown in FIGS. 20B and 20C although other configurations are also contemplated. This pear shape in some applications is designed to conform to the shape of the bladder.

The inner and outer balloons 204, 202 can by way of example be made of urethane, although other materials are also contemplated such as silicone or EVA.

Figure 25A:
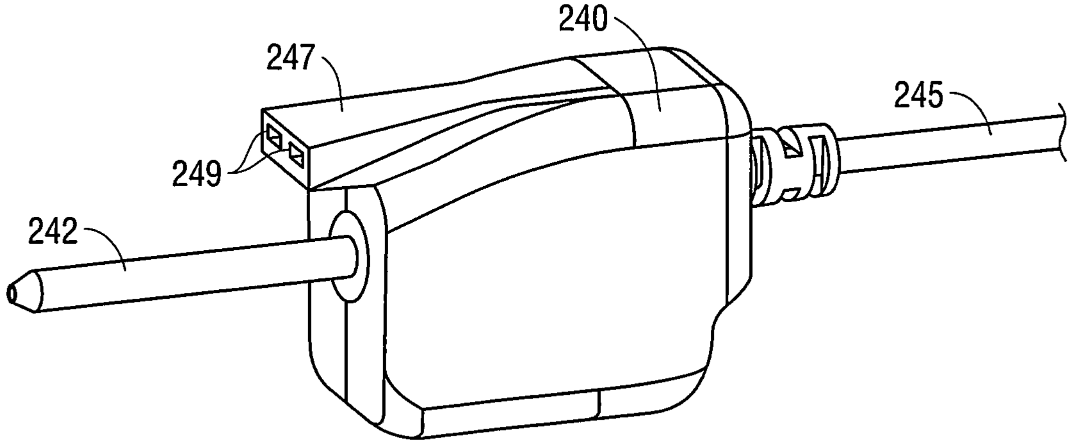
FIG. 25A is a perspective view of the transducer hub of FIG. 24A.
Figure 25B:
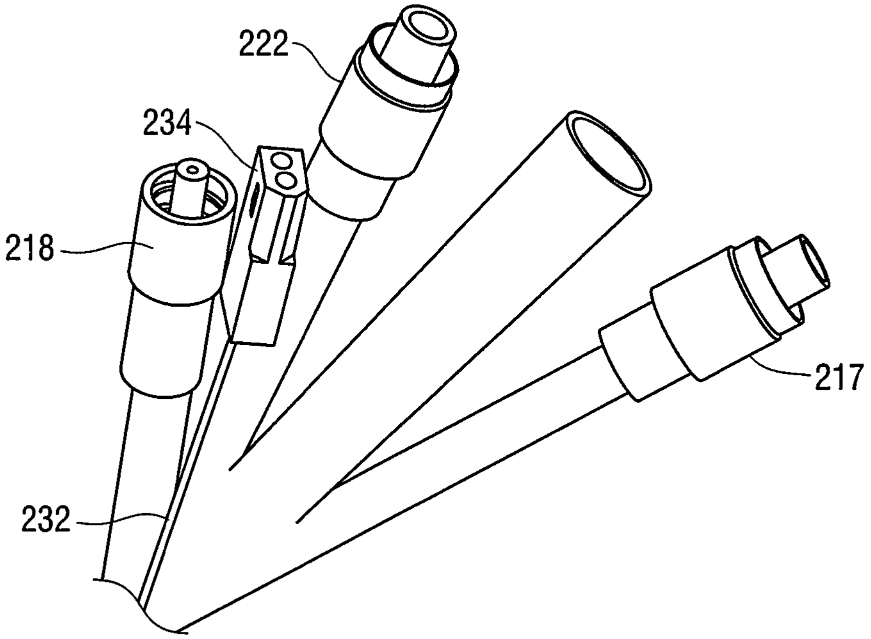
FIG. 25B is a perspective view of the proximal end of the catheter showing a connector for the thermocouple wire.
Figure 26:
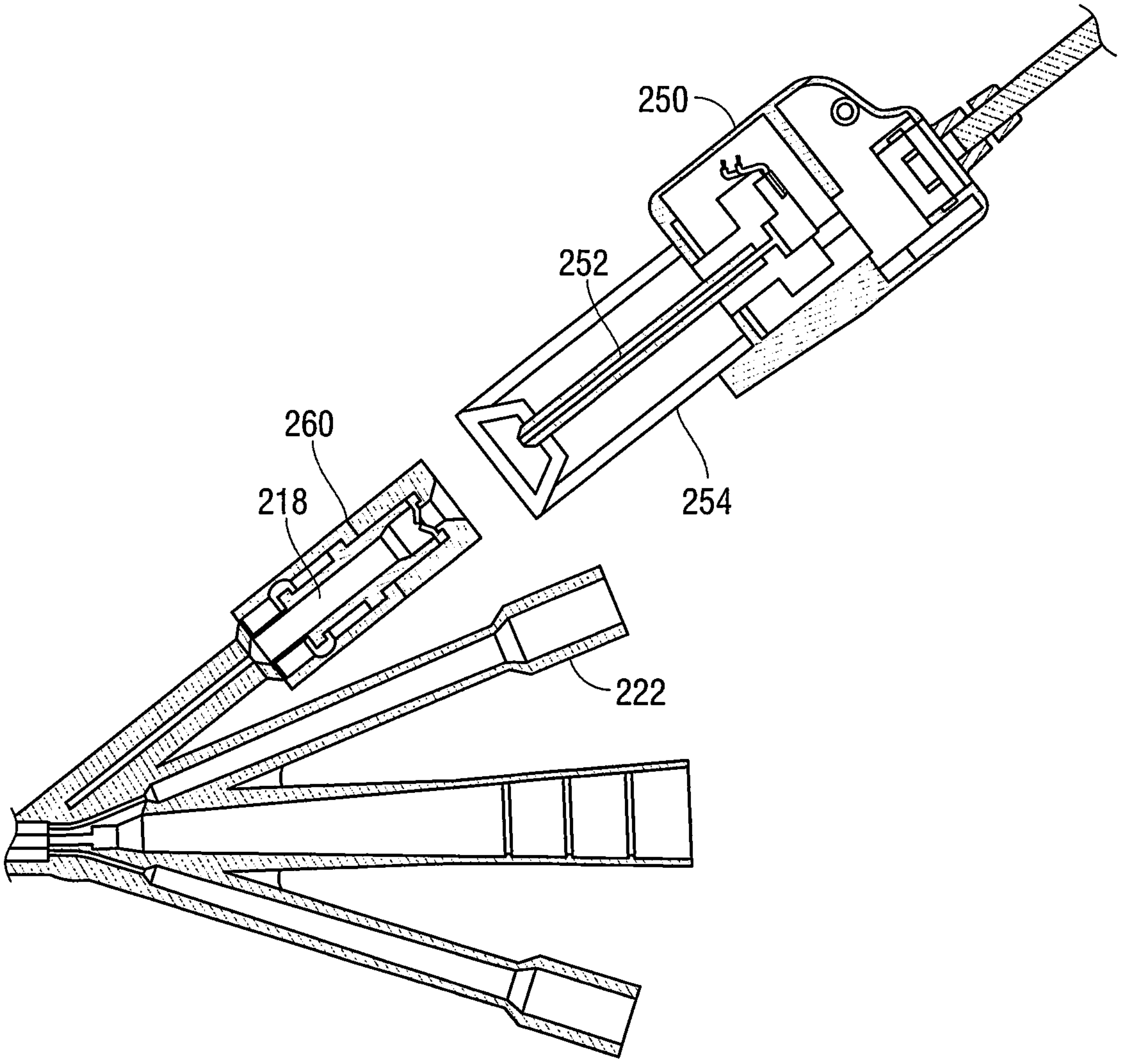
FIG. 26 is a side view of alternate embodiment of the pressure transducer hub having a shroud over the elongated member for snap fitting onto the catheter.
Figure 27:
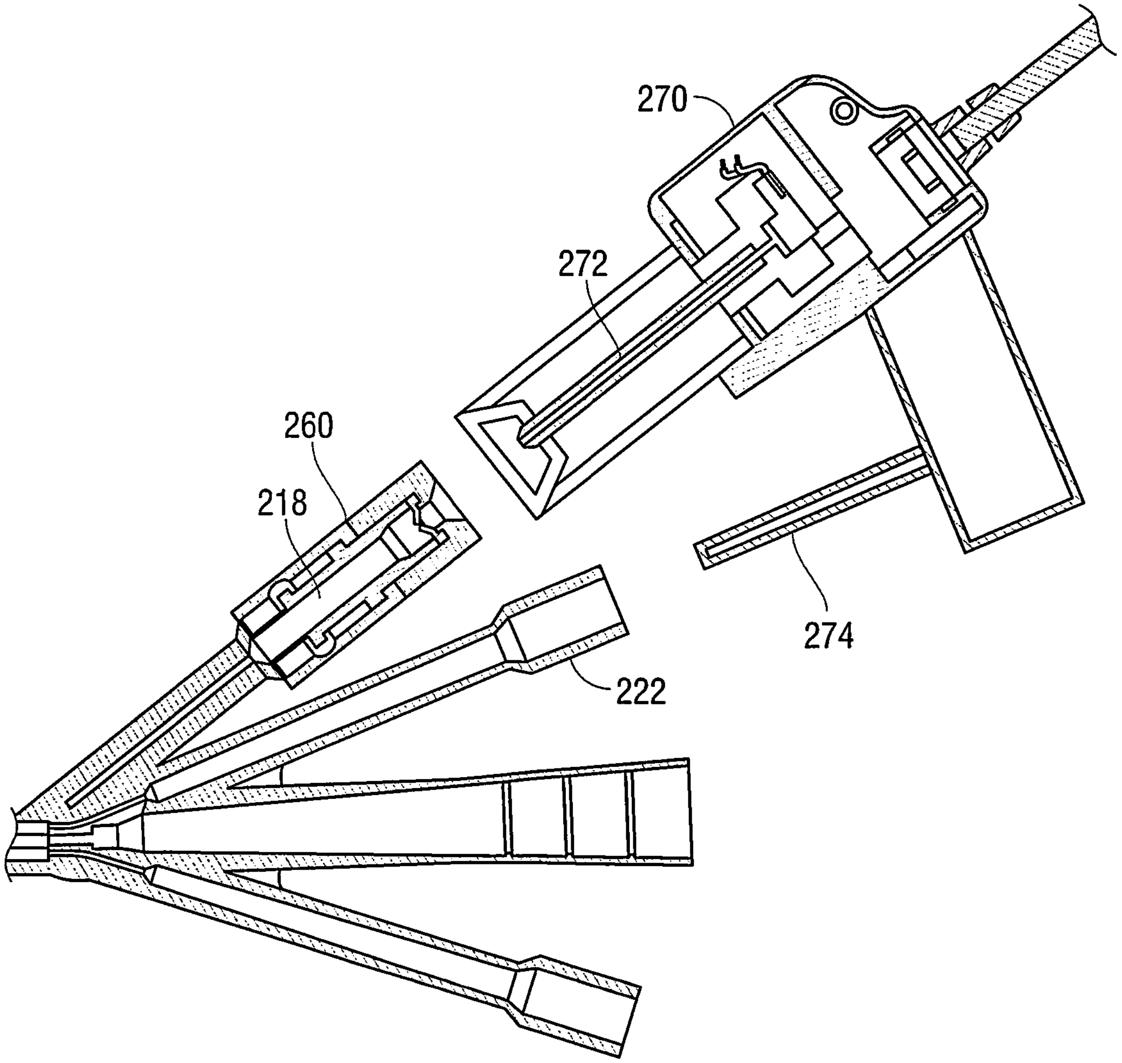
FIG. 27 is a schematic view of an alternate embodiment of the pressure transducer hub extendable into two side ports of the catheter.

A temperature sensor 230 (FIG. 18B), such as a thermocouple, is positioned within the catheter 200 at a distal end to measure core body temperature. The sensor 230 is shown positioned in a lumen 216 separate from the lumens 214 and 212. One or more wires 232 extend from the sensor 230 through the lumen 216, exiting the lumen 216 and catheter 200 at a proximal end between the angled extensions/ports of the catheter 200, e.g., between the port 218 for the inner balloon 204 and the port 222 for the outer balloon 202. A connector 234, e.g., a male connector, is at the proximal terminal end of the wire 232 as shown in FIG. 25B. The transducer hub 240 includes a connector 247 with openings 249 (FIG. 25A) which receive the connector 234 of the wire 232. When the hub 240 is mounted to port 218 of catheter 200, the connector 234 of the wire is automatically connected to a connector carried by or within the hub 240 which is in communication with a temperature monitor. Note the connector, e.g., female connector, within or carried by the hub 240 can already be mounted to an external temperature monitor via a cable when the hub 240 is mounted to catheter 218 or alternatively the hub 240 can first be mounted to port 218 of the catheter 200 and then a cable is connected between the temperature monitor and catheter 200. In the illustrated embodiment of FIG. 25A, the wire connector 234 can plug into the openings 249 of connector 247 positioned on the hub 240. Note the connector 247 can also be internal of the hub 240 with an opening in the wall of the hub to enable access for the wire connector. Also note that alternatively the wire can include a female connector and the hub can have a male connector. Other types of connectors/connections are also contemplated.

As can be appreciated, connection of the transducer hub 240 to the catheter 200 (port 218) a) automatically connects the temperature sensor 230 to a connector for communication with a temperature monitor cable; and b) automatically advances air through the first lumen 214 to expand the inner balloon 204.

The catheter 200 can optionally include a stabilizing balloon 206 similar to balloon 76 of FIG. 8A. The stabilizing balloon 206 can be made of silicone, although other materials are also contemplated. If provided, the catheter 200 would have a lumen, e.g., lumen 210, to inflate the stabilizing balloon 206. Angled side port 217 can be provided in communication with lumen 210 for injection of a liquid or gas to expand the stabilizing balloon 206. The foregoing description of the stabilizing balloons in connection with other embodiments is fully applicable to balloon 206. Catheter 200 also includes a lumen 211 with a distal side opening 211*a* (FIG. 18B) to provide for drainage of the bladder as in the aforedescribed embodiments. In the illustrated embodiment, the side opening 211*a* is distal of outer balloon 202 and inner balloon 204 and distal of the stabilizing balloon 210 which as shown is proximal of outer balloon 202 and inner balloon 204. In alternate embodiments, the side opening for drainage could be proximal of the inner and outer balloons. In alternate embodiments, the stabilizing balloon 206 can be distal of the outer balloon 202.

Figure 23:
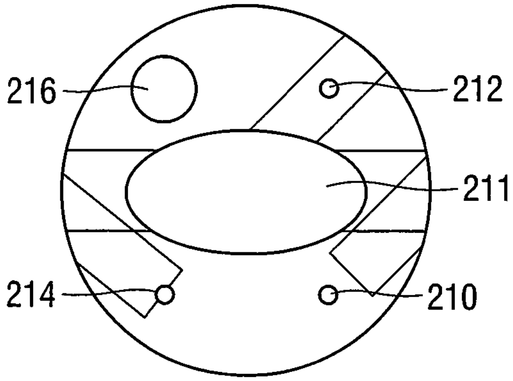
FIG. 23 is a transverse cross-sectional view of the catheter of FIG. 18 illustrating the five lumens of the catheter.
Figure 24A:
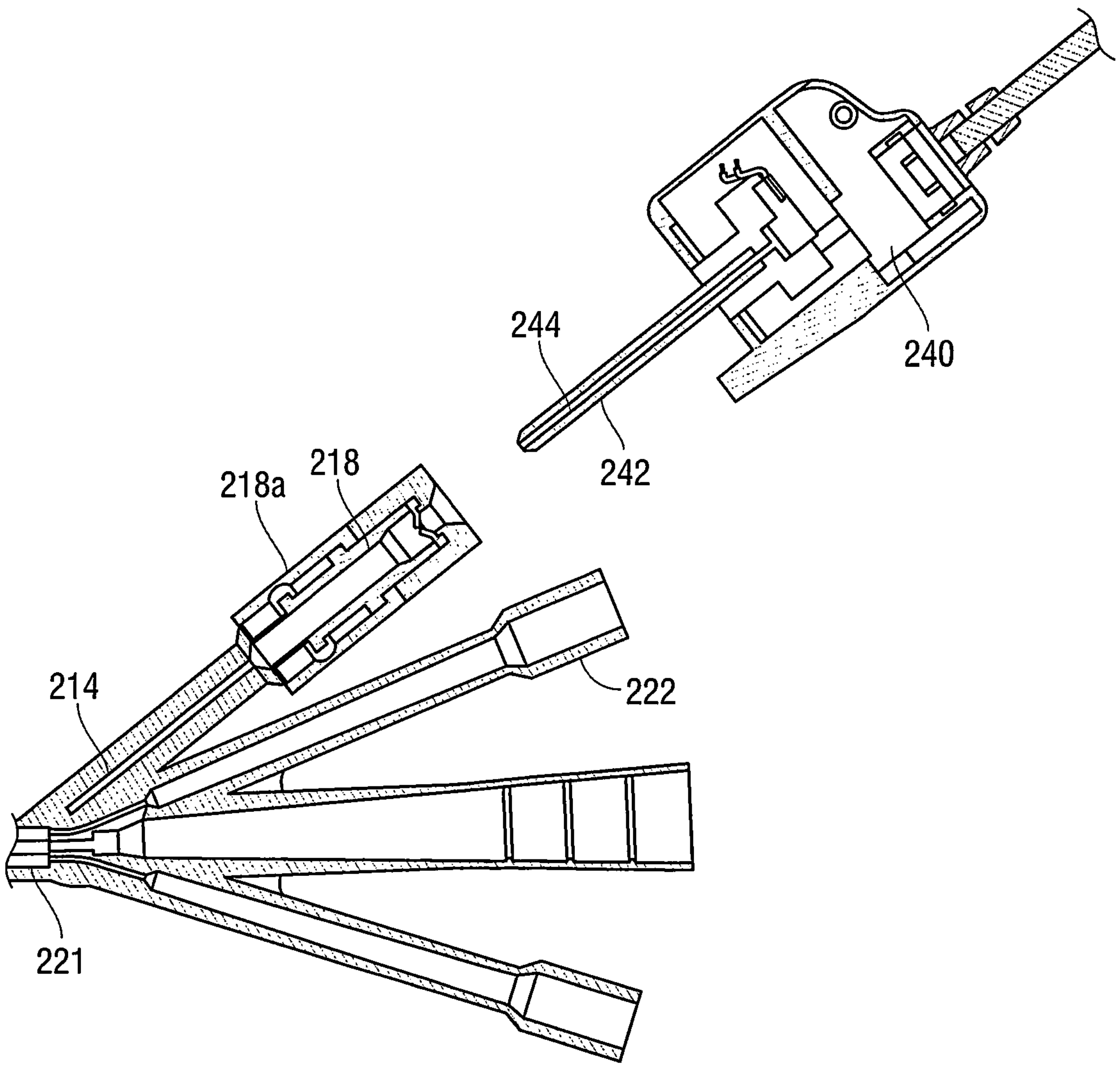
FIG. 24A is a cutaway side view showing the pressure transducer hub prior to connection to the catheter of FIG. 18A, a portion of the hub wall and catheter connector removed to show internal components.
Figure 24B:
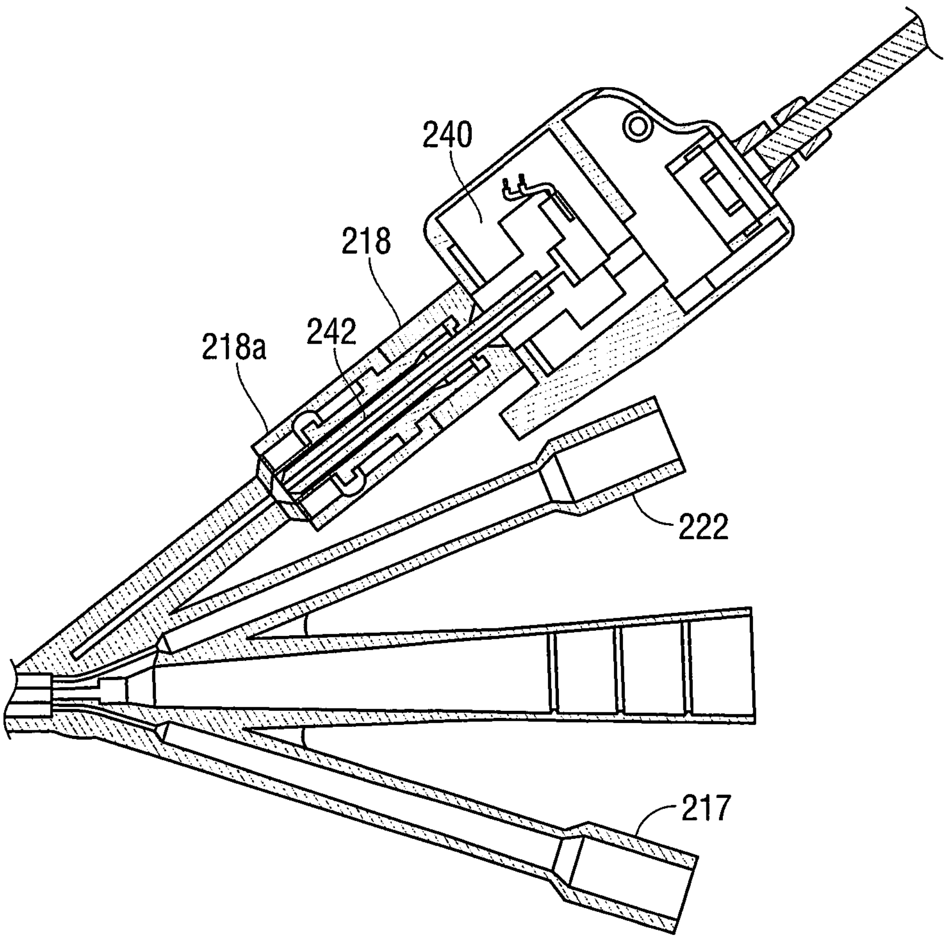
FIG. 24B is a side view similar to FIG. 24A showing the hub attached to the catheter.

In the embodiment of FIG. 18A, catheter 200 has five lumens: 1) lumen 214 communicating with inner balloon 204 to inflate the inner balloon 204 and forming the air filled chamber; 2) lumen 212 communicating with outer balloon 202 for inflating outer balloon 202; 3) lumen 210 communicating with the stabilizing balloon 206 to inflate stabilizing balloon 206; 4) drainage lumen 211 having a side opening 211*a* at a distal end for drainage of the bladder; and 5) lumen 216 for the temperature sensor wire(s) 232. (Note in alternate embodiments, the temperature sensor wires could be located in the lumen 214 so the catheter would not have the additional lumen 216) Catheter 200 also has three angled extensions/ports at its proximal end 201: 1) port 218 for access to lumen 214 to inflate the inner balloon 204; 2) port 222 for access to lumen 212 to inflate outer balloon 202; and 3) port 217 for access to lumen 210 to inflate stabilizing balloon 206. Drainage lumen 211 extends linearly terminating at region 223. Lumen 216 terminates proximally at the region of the angled ports 218, 222 through which wire 232 can exit from the catheter 200 for connection to a temperature monitor via hub 240. Note the location of the ports can vary from that illustrated in FIG. 18. Also, location of the lumens and the cross-sectional dimension and size of the lumen can vary from that shown in FIG. 23 as FIG. 23 provides just one example of the location and size, e.g., diameter, of the lumens as well as the shape/cross-sectional configuration and location. The catheter 200, as in the foregoing embodiments, can have an atraumatic tip 209.

In use, catheter 200 is inserted into the bladder and stabilizing balloon 206 is inflated to secure the catheter 200 in place. The system is charged by inflation of the inner balloon 204, i.e., preferably partially inflated for the reasons discussed above, by advancement of air through lumen 214 upon attachment of the pressure transducer 240 to the port 218 of catheter 200. Such attachment moves elongated member 242 into lumen 214 to displace the air (or other gas) already in the lumen 214 to expand the inner balloon 204. A closed system is formed by the internal space 204*a* of the inner balloon 204 and the internal lumen 214 communicating with the internal space 204*a* of inner balloon 204. In a preferred embodiment, additional air does not need to be added to the balloon 204/lumen 214. Outer balloon 202 is filled, i.e., preferably partially inflated for the reasons discussed above, via injection of air through the separate port 222 which communicates with lumen 212 of catheter 200. With the outer balloon 202 inflated, pressure monitoring can commence as external pressure applied to the larger circumferential outer surface of the outer balloon 202 compresses and deforms the outer balloon 202 which exerts a force on the outer wall of inner balloon 204 (via fluid contact with the outer wall of the inner balloon) and compresses the inner balloon 204. As the inner balloon 204 is compressed and deformed in response to compression/deformation of the outer balloon 202 based on changes to bladder pressure, the pressure sensor within the external hub 240 attached at the proximal end of the catheter 200 provides continuous pressure readings, converted to an electrical signal by the transducer of the sensor within the hub 240, and then electrically communicates through a connector, e.g. cable 245, to an external monitor either directly or via a converter to display pressure readings. Although, the system is capable of continuous pressure and continuous temperature monitoring, it can also be adapted if desired for periodic monitoring so the pressure and/or temperature readings can be taken at intervals or on demand by the clinician. Temperature readings are also taken during the procedure as temperature sensor 230 is connected to a temperature monitor via wire 232 connected to a connector of hub 240 which is connected to the temperature monitor to display temperatures. The temperature monitor can be separate from the pressure display monitor or alternatively integrated into one monitor. Cable 245 can connect to the temperature monitor as well (directly or via a converter) or a separate cable extending from the hub 240 could be provided for connection to the temperature monitor.

Note that although separate lumens are provided for the inflation of inner balloon 202 and outer balloon 204, in an alternate embodiment, a single lumen can be utilized to inflate both balloons 202 and 204. In such embodiment, catheter 200 can have one less angled port and one less lumen since inflation of the outer balloon 202 would be through port 218 and lumen 214.

The proximal and distal end of the inner balloon 204 in the illustrated embodiment are within the confines of the outer balloon 202, i.e., the proximal end of the inner balloon 204 is distal of the proximal end of the outer balloon 202 and the distal end of the inner balloon 204 is proximal of the distal end of the outer balloon 202. Thus, in this illustrated embodiment, the inner balloon 204 is fully encapsulated within the outer balloon 202.

With the inner/outer balloon arrangement, the larger outer surface of the outer balloon 202 takes gross measurements and then the forces are concentrated on the smaller inner balloon 204 to amplify/concentrate pressure on the small area of the inner balloon so small changes can be detected and waves transmitted to the pressure transducer (via the length of the lumen to a proximal transducer, e.g., an external pressure transducer).

As noted above, preferably no additional air needs to be added after mounting of hub 240. However, it is also contemplated that in alternate embodiments a port can be provided in communication with hub 240 to enable subsequent injection of air though lumen 214 and into inner balloon 204. Additionally, outer balloon 202 can in some embodiments receive additional fluid injection via port 222 during the procedure.

FIGS. 30A-34 illustrate an alternate embodiment of the catheter, designated generally by reference numeral 400. The catheter 400 differs from catheter 200 of FIG. 18A in the attachment of the inner and outer balloons to the catheter shaft. The catheter 400 also differs catheter 200 described above in the location of the drainage hole(s). In all other respects catheter 400 is the same as catheter 200 and thus the features and functions of catheter 200, and its alternatives disclosed herein, are fully applicable to catheter 400.

Catheter 400 has a shaft 402 having a distal region (portion) 402*a* terminating in a distal opening 402*b*. Distal opening 402*b* receives core pin 410 therein. Core pin 410, also referred to as a bonding pin or a connecting pin, has a proximal end 414*a* dimensioned for insertion in a press fit through opening 402*b* and into the lumen in distal region 402*a* of shaft 402. In the illustrated embodiment, the proximal end 414*a* has a non-circular shape, e.g., a triple lobe or Y shape, corresponding to the shape of the opening 402*b*. The distal end of the pin 410 has a reduced diameter cylindrical portion 414*b* which receives thereover a distal tip 412 (also referred to herein as a distal plug).

Catheter 400 further has a retention (stabilizing) balloon 404, an inner balloon 408 and an outer balloon 406. The retention balloon 404 is spaced proximally of the outer balloon 406 and inner balloon 408. The outer balloon 406 encapsulates the inner balloon 408 such that the inner wall 408*c* of the inner balloon 408 is contained within the outer balloon 406. The outer wall 406*c* of outer balloon 40*c* is exposed to the patient, e.g., the bladder. The retention balloon 404 functions in the same way as the retention (stabilizing) balloons described above and can be of varying shapes as described herein. The inner and outer balloons 408, 406 function in the same way as the inner and outer balloons 204, 202 of catheter 200.

Figure 30A:
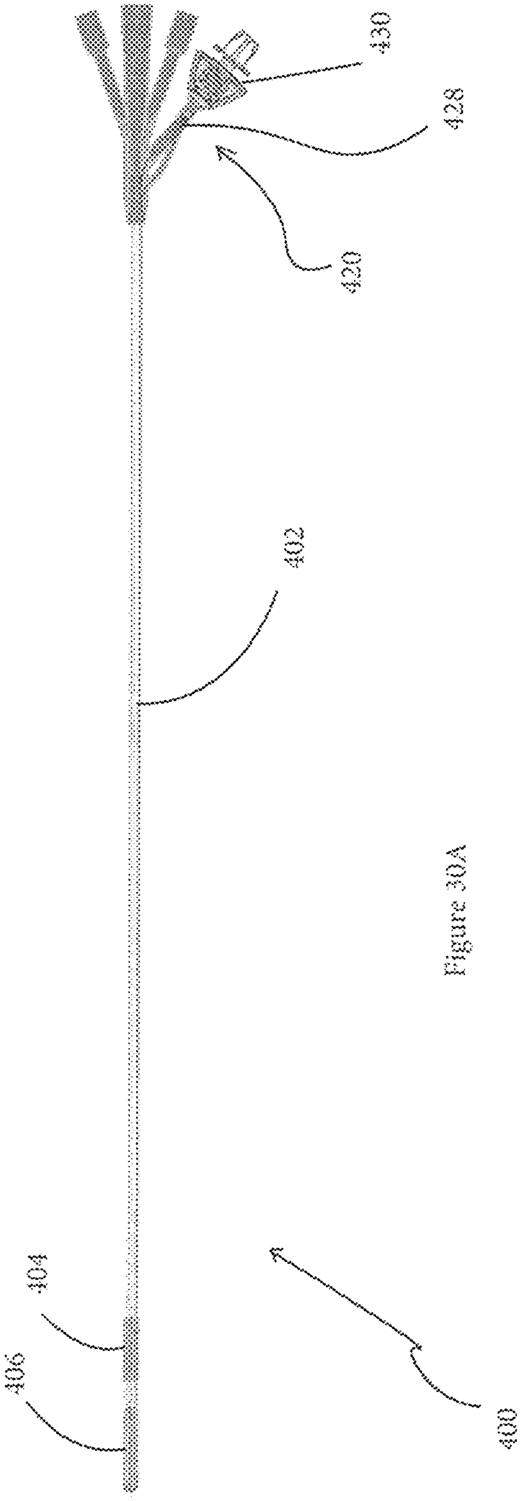
FIG. 30A is a side view of an alternate embodiment of the catheter of the present invention.
Figure 30B:
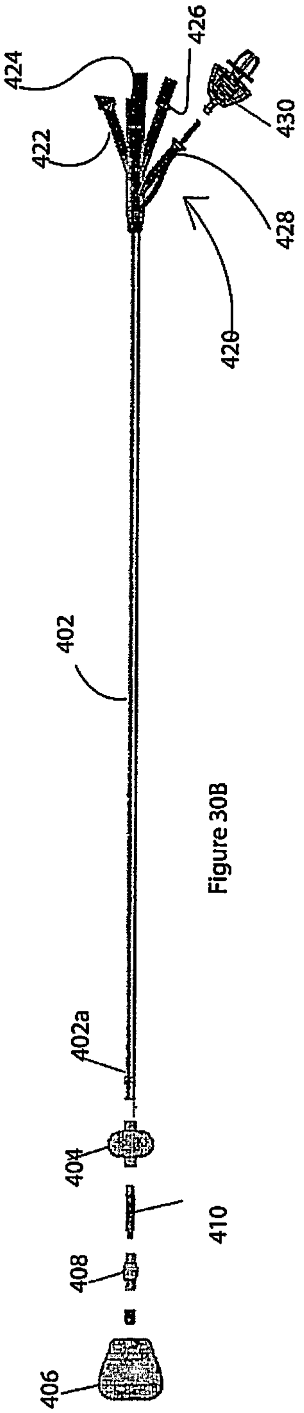
FIG. 30B is an exploded side view of the catheter of FIG. 30A.
Figure 30C:
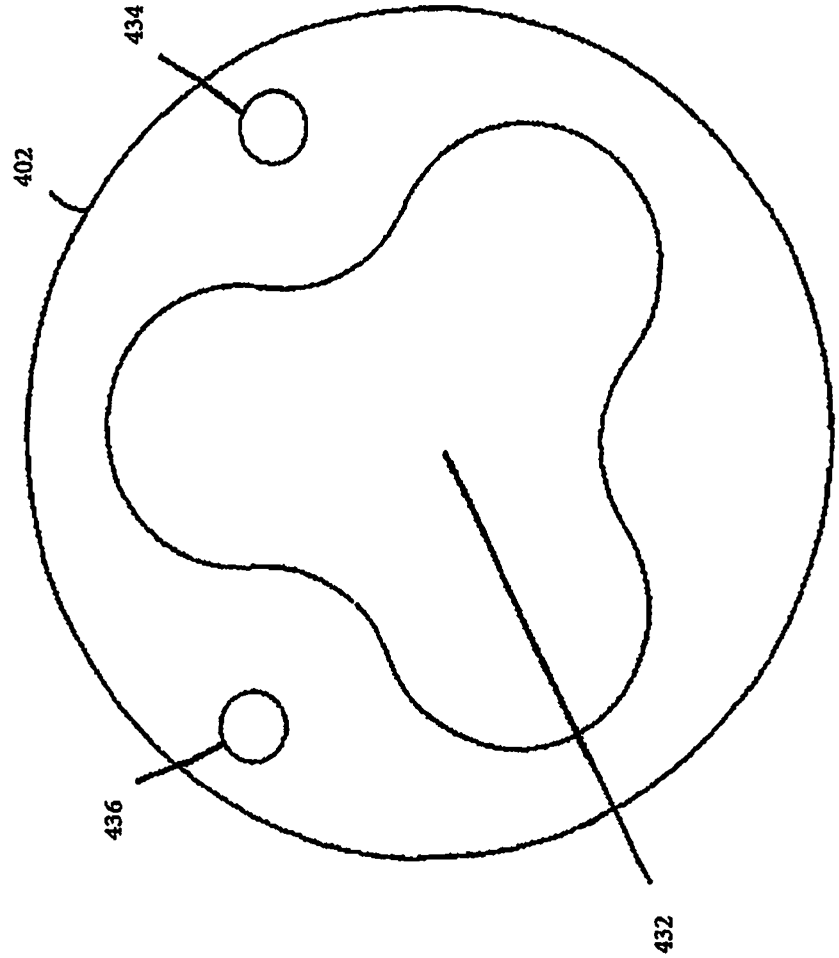
FIG. 30C is an enlarged transverse cross-sectional view of the catheter of FIG. 30A.
Figure 31:
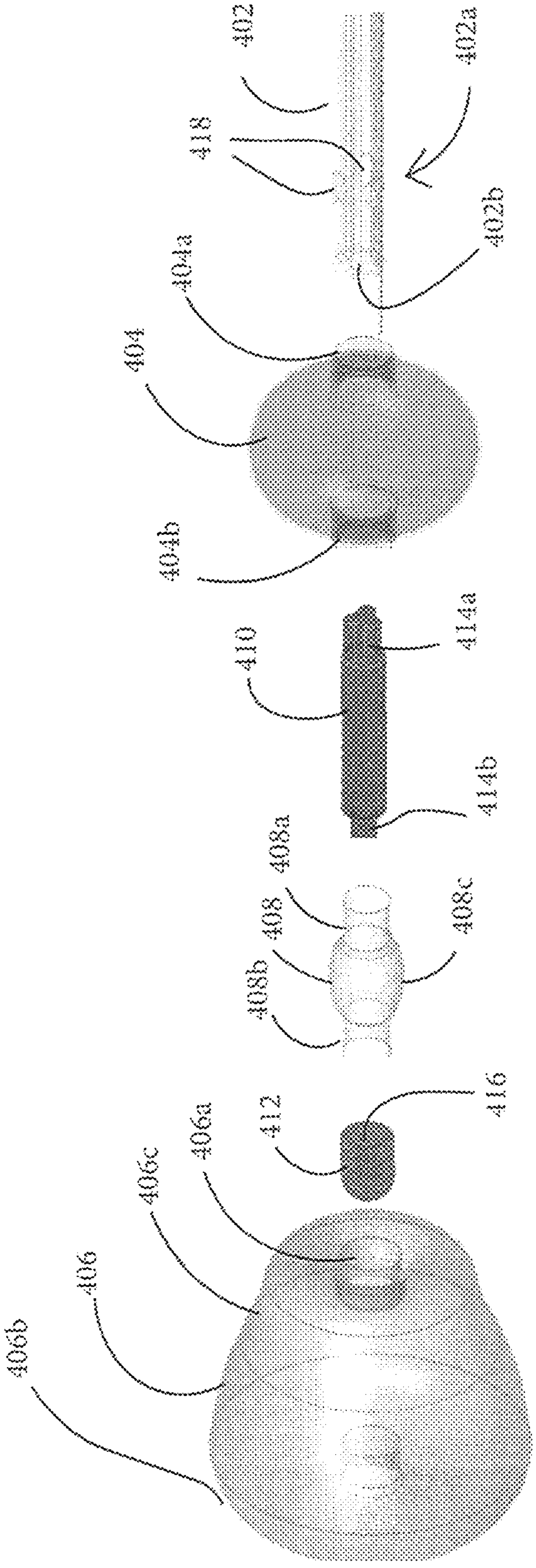
FIG. 31 is a close up exploded view of the distal end of the catheter of FIG. 30A.

As shown in the cross-sectional view of FIG. 30C, the catheter shaft 402 has four lumens: 1) lumen 438 communicating with inner balloon 408 to inflate the inner balloon 408 and forming the gas, e.g., air, filled chamber; 2) lumen 434 communicating with outer balloon 406 for inflating outer balloon 406; 3) lumen 436 communicating with the retention balloon 404 to inflate retention balloon 404; and 4) drainage lumen 432 having one or more side openings 418 (FIG. 32C) at a distal region of the catheter for drainage of the bladder. The lumens 438, 434 and 436 terminate inside of their respective balloons 402, 406 and 404. The side opening(s) 418 for drainage are positioned between the outer/inner balloon 406, 408 and the retention balloon 404 such that the outer balloon 406 and inner balloon 408 are distal of the side opening(s) 418 and the retention balloon 404 is proximal of the side opening(s) 418. Temperature sensor wires can be positioned in lumen 438, running parallel to the tubular portion (described below) of the inner balloon in embodiments where the balloon has the tubular portion, e.g., balloon 458, with the thermistor sensor located near the drainage holes 418. The temperature sensor wires can be positioned in the same lumen as the lumen for filling the outer balloon or the inner balloon or an additional lumen can be provided for the temperature sensor wire(s).

Catheter 400 also has three angled extensions/ports at its proximal end 420 (FIG. 30B): 1) port 428 for access to lumen 438 to inflate the inner balloon 408; 2) port 426 for access to lumen 434 to inflate outer balloon 406; and 3) port 422 for access to lumen 436 to inflate stabilizing balloon 404. Drainage lumen 432 extends linearly terminating at a distal region proximal of core pin 410 and terminating proximally at port 424. Note the location of the ports can vary from that illustrated in FIG. 30B. Also, the location of the lumens and the cross-sectional dimension and size of the lumens can vary from that shown in FIG. 30C as FIG. 30C provides just one example of the location and size, e.g., diameter, of the lumens as well as the shape/cross-sectional configuration and location.

Figure 32A:
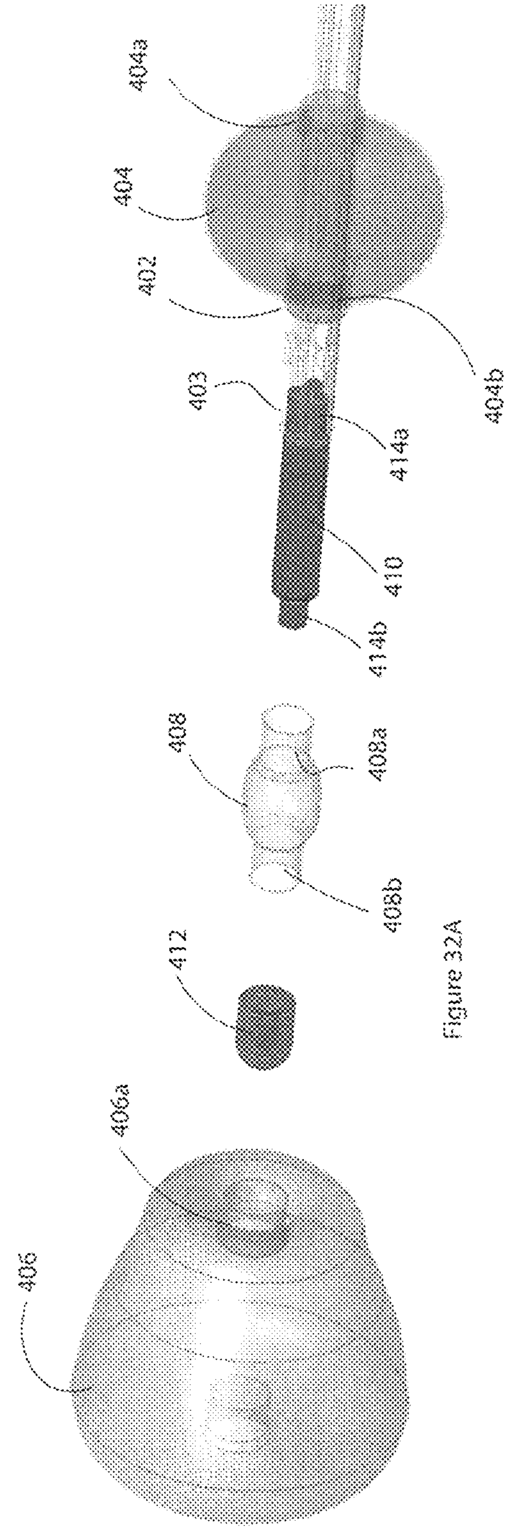

The steps of manufacture (assembly) of the balloons to the catheter will now be described with reference to FIGS. 32A-32C. The assembly steps are shown with the balloons inflated for ease of illustration but the assembly would preferably be made with the balloons deflated. In manufacture, the stabilizing balloon 404, which is identical in function and can be the same shape as the stabilizing (retention) balloons discussed above, such as a donut shape as shown, is placed over the outer shaft 402 and proximal and distal extensions 404*a*, 404*b* of balloon 404 are attached, e.g., welded to the shaft 402. In the illustrated embodiment, the stabilizing balloon 404 is composed of the same material as the distal region 402*a* of shaft 402. In one embodiment by way of example, the material is silicone, although other materials are also contemplated. After the stabilizing balloon 404 is placed over the shaft 402, positioned proximal of the distal end of the shaft 402, and preferably after it is also attached to the shaft 402, the bonding pin 410 is inserted into the shaft 402. More specifically, proximal extension 414*a* extends into distal opening 402*b* of shaft 402, with a portion of the pin 410 including the distal extension 414*b* extending distally from and exposed from the shaft 402 as shown in FIG. 32A. The bonding pin 410 is preferably mechanically fixed, such as by a press fit into the lumen of the shaft 402. The shaft 402 contains small holes overlying the inserted pin 410 and the small holes are filled with material, e.g., silicone, to secure the pin 410 to the shaft 402.

Figure 32B:
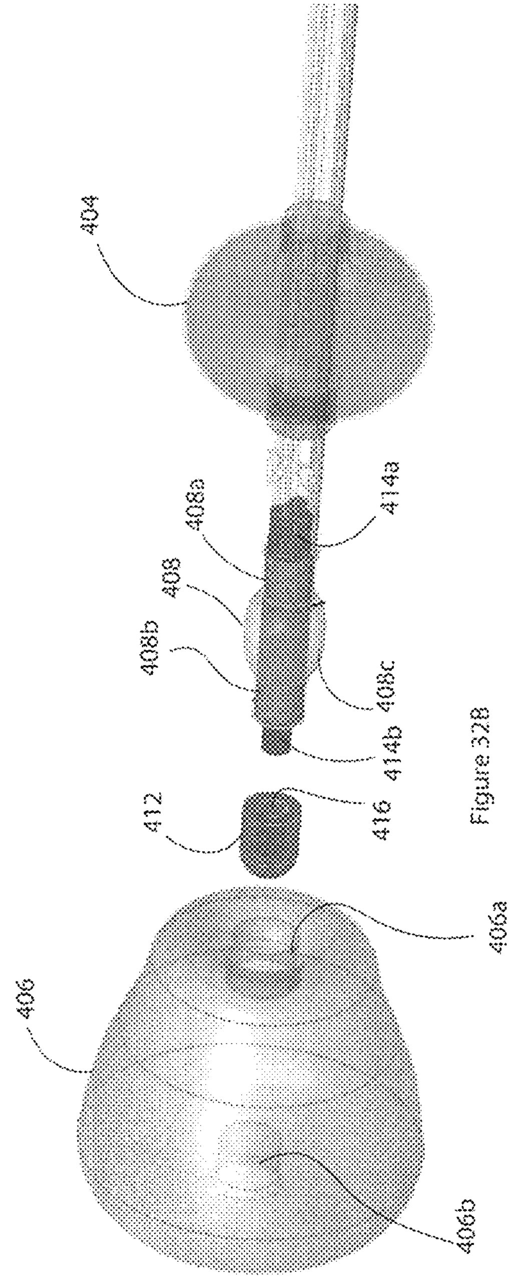
Figure 32C:
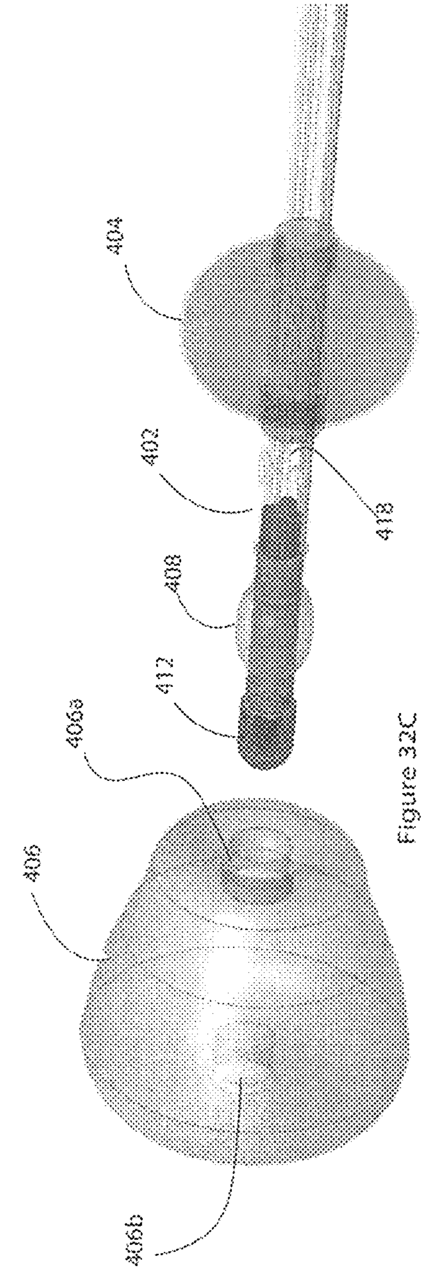
Figure 32D:
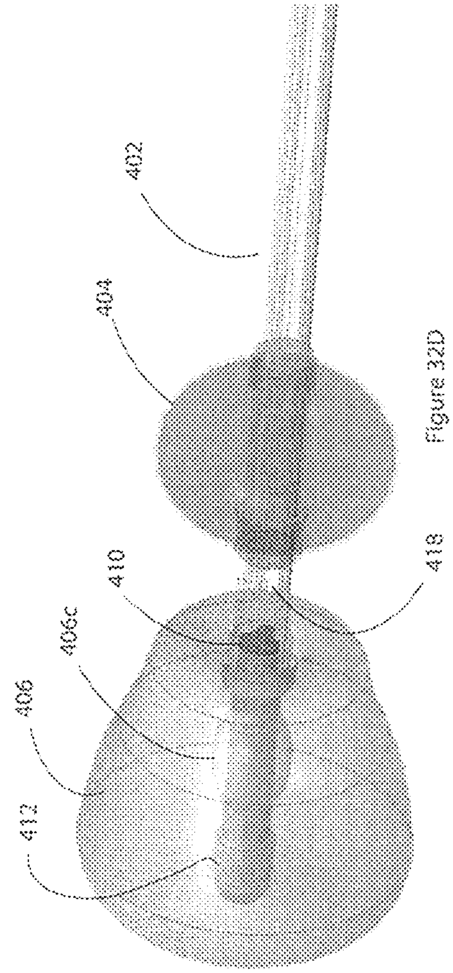
Figure 33:
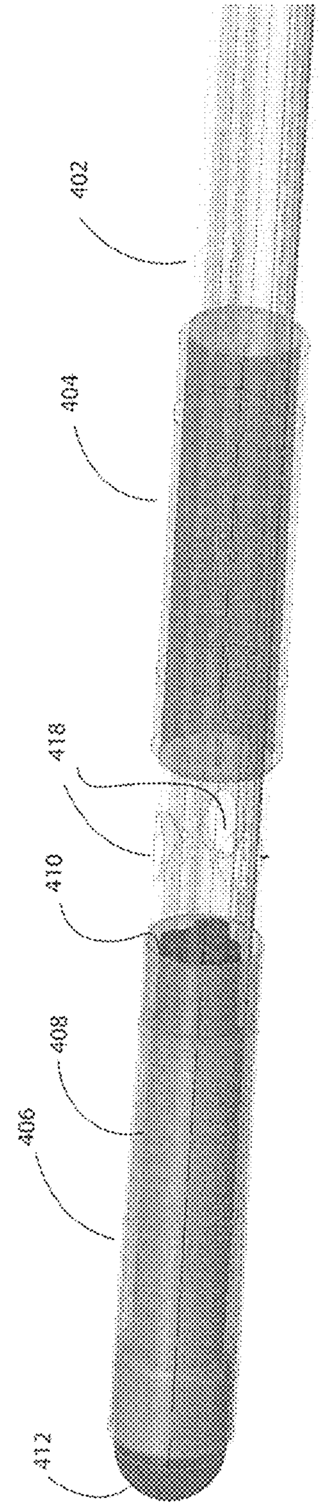
FIG. 33 is a side perspective of the distal end of the catheter of FIG. 30A showing the balloons in the deflated condition.

Next, with reference to FIG. 32B, the inner balloon 408 is placed over the bonding pin 410 and proximal and distal extensions 408*a*, 408*b* are attached, e.g., welded, to the bonding pin 410. The balloon 408 is attached to the center cylindrical region of the pin 410, leaving the proximal and distal extensions 414*a*, 414*b* exposed. In the illustrated embodiment, the inner balloon 408 is composed of the same material as the bonding pin 410 and both the bonding pin 410 and inner balloon 408 are composed of a different material than the distal region 402*a* of the shaft 402. (The distal region 402*a* can be the same material as the remainder or other portions of the shaft 402 or composed of a different material). After placement of the inner balloon 408 over the bonding pin 410, and either before or after attachment (e.g., welding) of the inner balloon 408 to the pin 410, distal tip or plug 412 is placed over distal extension 414*b* of pin 410 (FIG. 32C). Distal tip 412 has an opening 416 to receive extension 414*b* and is mechanically fixed, e.g., by a press fit, to the pin extension 414*b*. As shown, the tip 412 is spaced distally from the inner balloon 408. The tip 412 in some embodiments is composed of a different material than the core pin 410 and is preferably composed of the same material as the outer balloon 406, e.g., silicone, although other materials can be utilized. FIG. 32D illustrates the next step in assembly as the outer balloon 406 is inserted over the distal tip 412 and over the inner balloon 408 and bonded at a proximal extension 406*a* to the outer shaft 402 and at the distal extension 406*b* to the tip 412. Thus, as can be appreciated, in this embodiment, the outer balloon 406 is bonded at both ends to structure composed of the same material as the outer balloon 406; and the inner balloon 408 is bonded at both ends to structure composed of the same material as the inner balloon 408. Also, the retention balloon 404 is bonded at both ends to structure composed of the same material as the retention balloon 404. In other words, as can be appreciated, the embodiment of FIGS. 31-34 enables inner and outer balloons of different materials to be attached to the shaft of the catheter, e.g., materials that do not bond. Additionally, or alternatively, it enables a balloon of a different material than the shaft to be attached to the shaft. In one embodiment by way of example, the shaft is composed of silicone, the inner balloon is composed of EVA and the outer balloon is composed of silicone so EVA is bonded to EVA and silicone is bonded to silicone. In such embodiment, the core pin by way of example is composed of EVA. It should be appreciated that these materials are provided by way of example as other materials are also contemplated.

Figure 34:
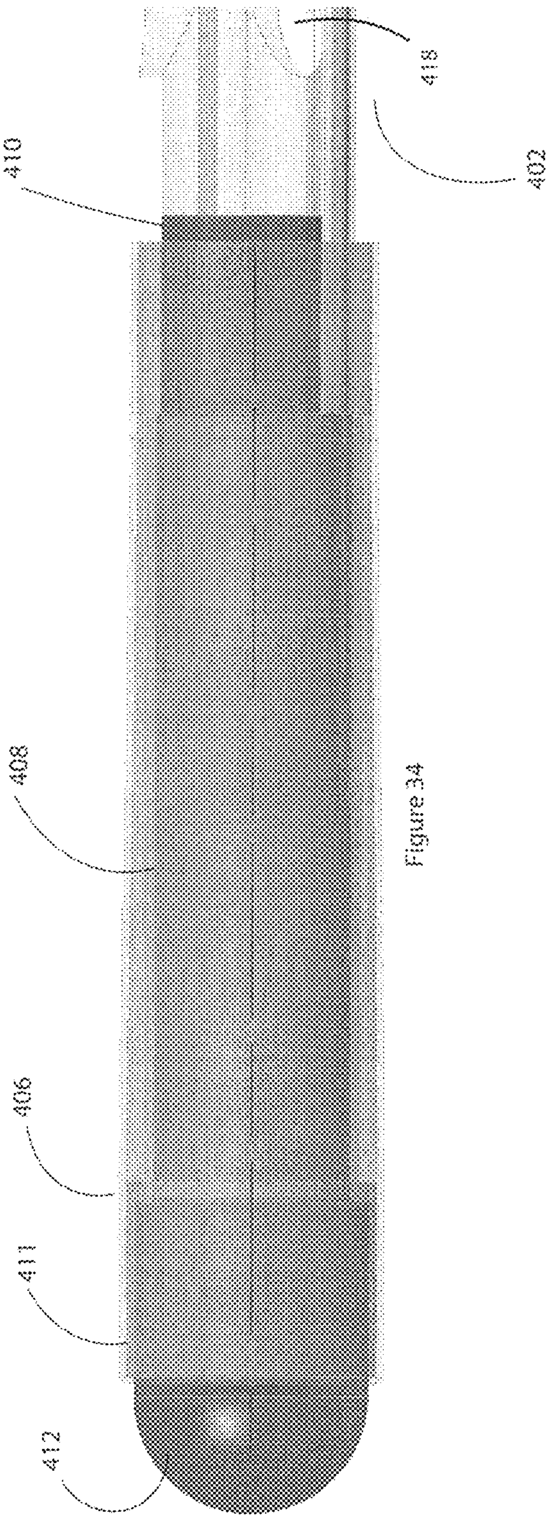
FIG. 34 is a close up view of the outer balloon of FIG. 33 in the deflated condition shown folded over itself.
Figure 35:
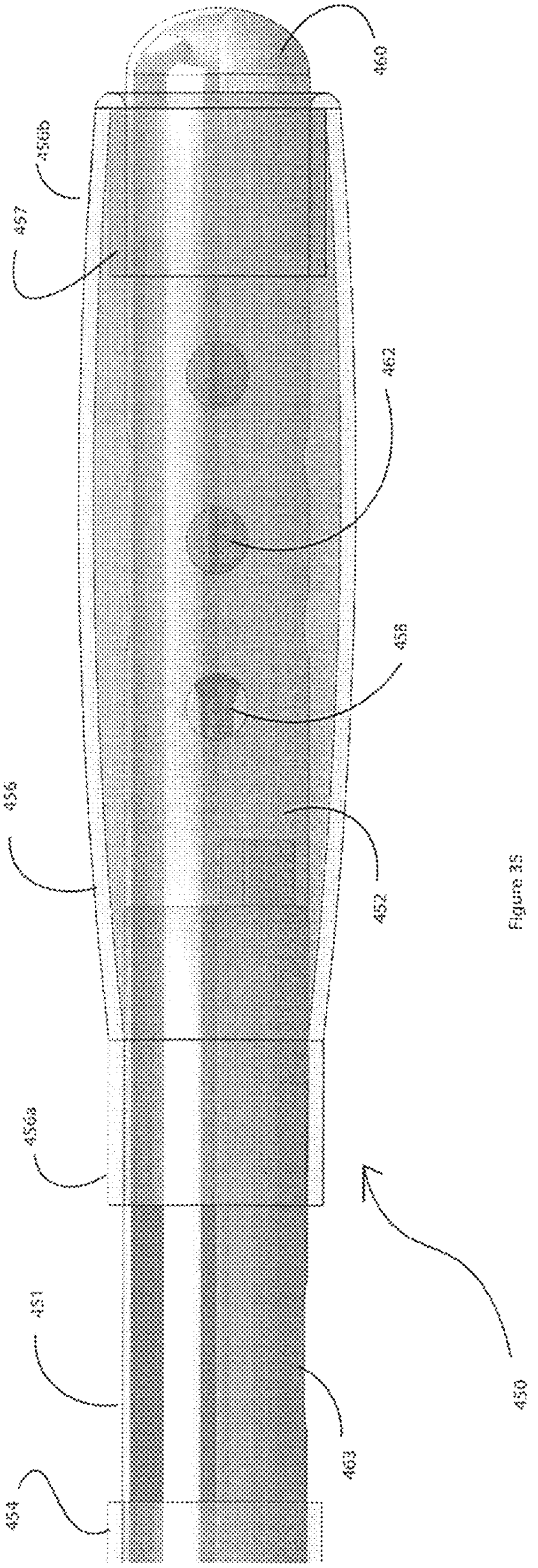
FIG. 35 is a side view of the distal region of the catheter of an alternate embodiment.
Figure 36:
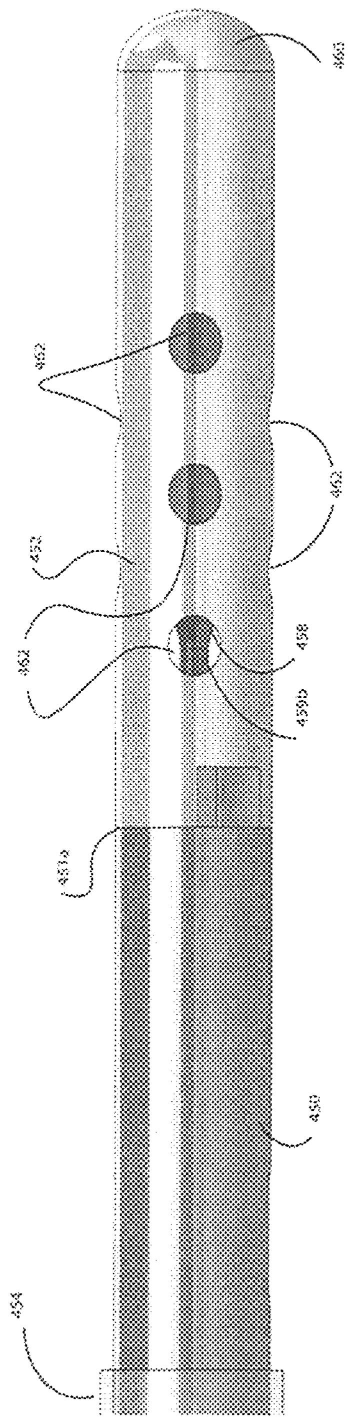
FIG. 36 is a view similar to FIG. 35 with the outer balloon removed for clarity.
Figure 37:
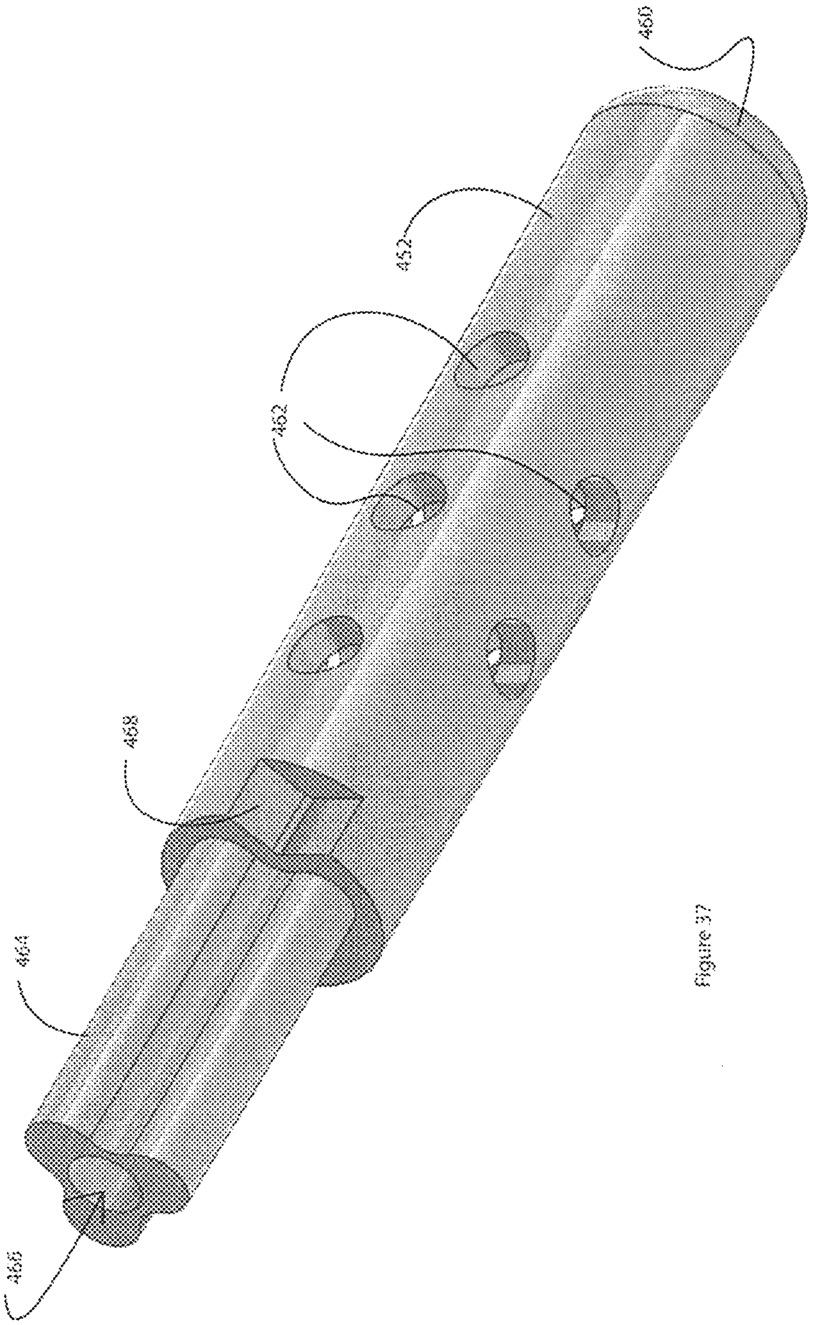
FIG. 37 is a perspective view of the inner balloon chamber of the catheter of FIG. 35.
Figure 38:
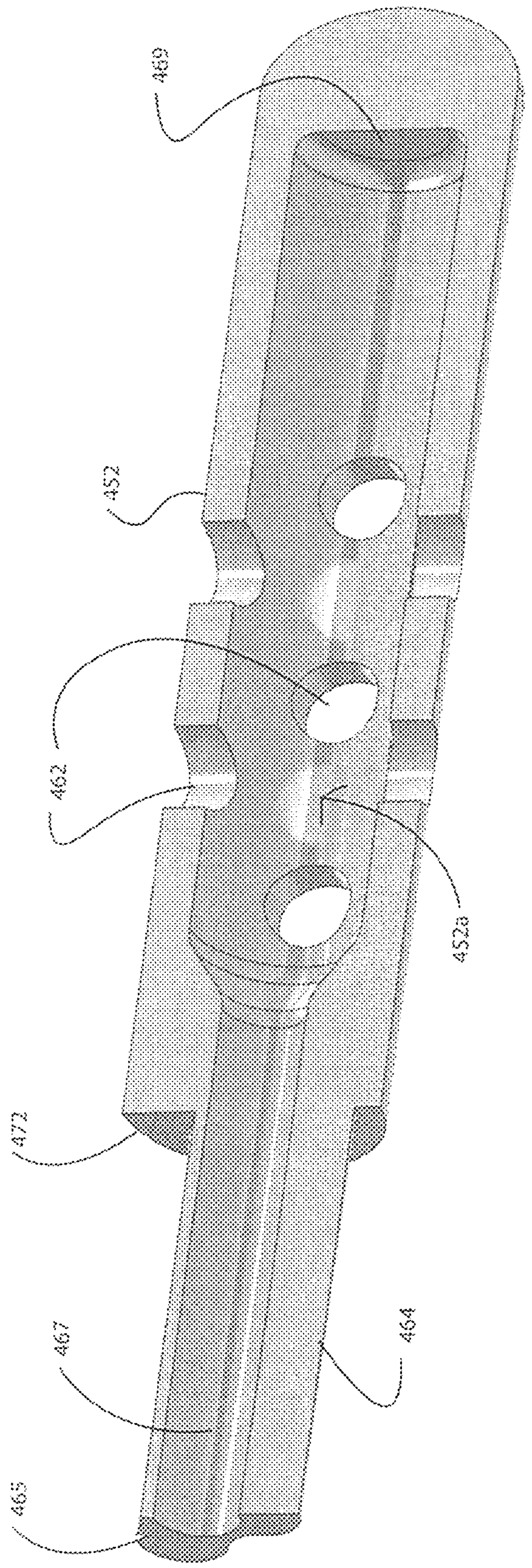
FIG. 38 is a cutaway view of the chamber of FIG. 37.
Figure 39:
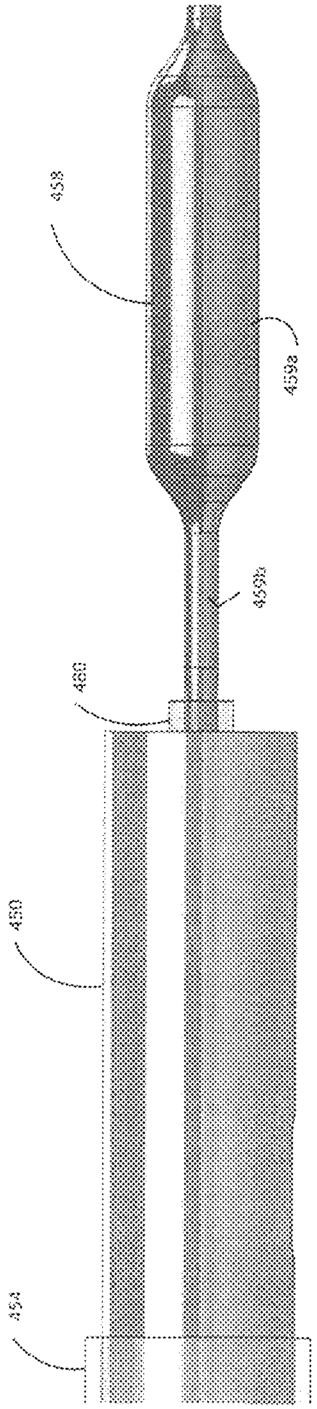
FIG. 39 is a view similar to FIG. 35 with the outer balloon and chamber removed for clarity.
Figure 40:
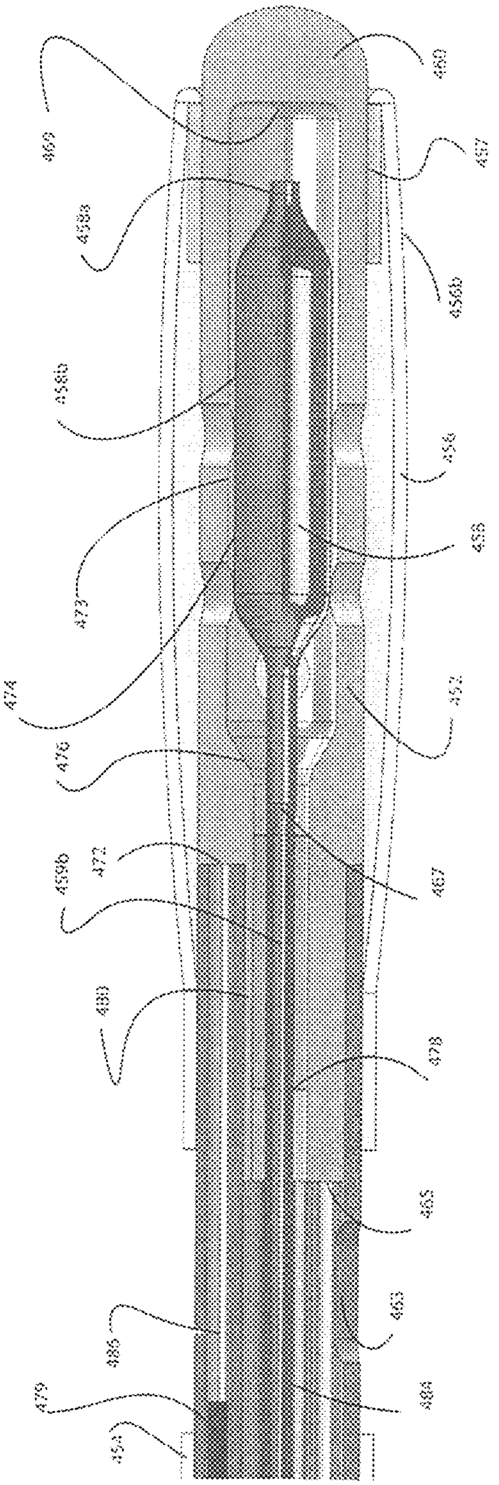
FIG. 40 is a cutaway view of the catheter of FIG. 35.
Figure 41:
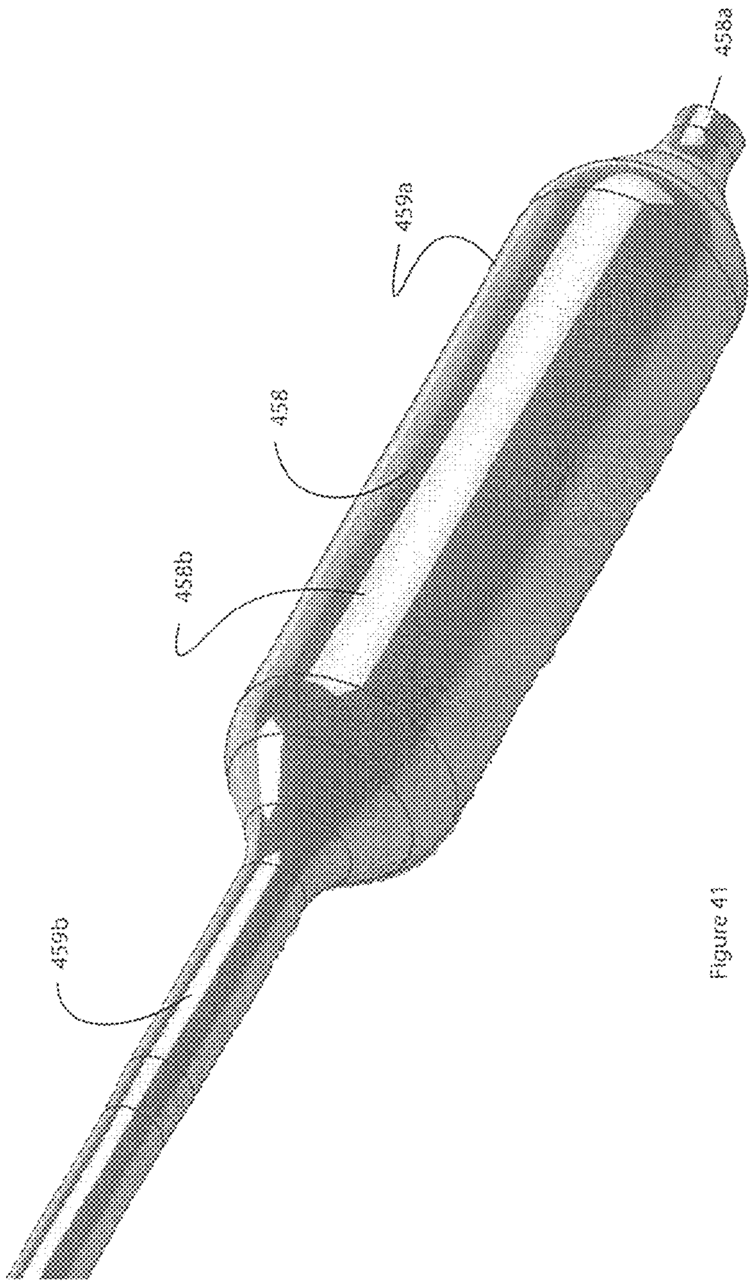
FIG. 41 is a perspective view of the inner balloon of the catheter of FIG. 35.
Figure 42:
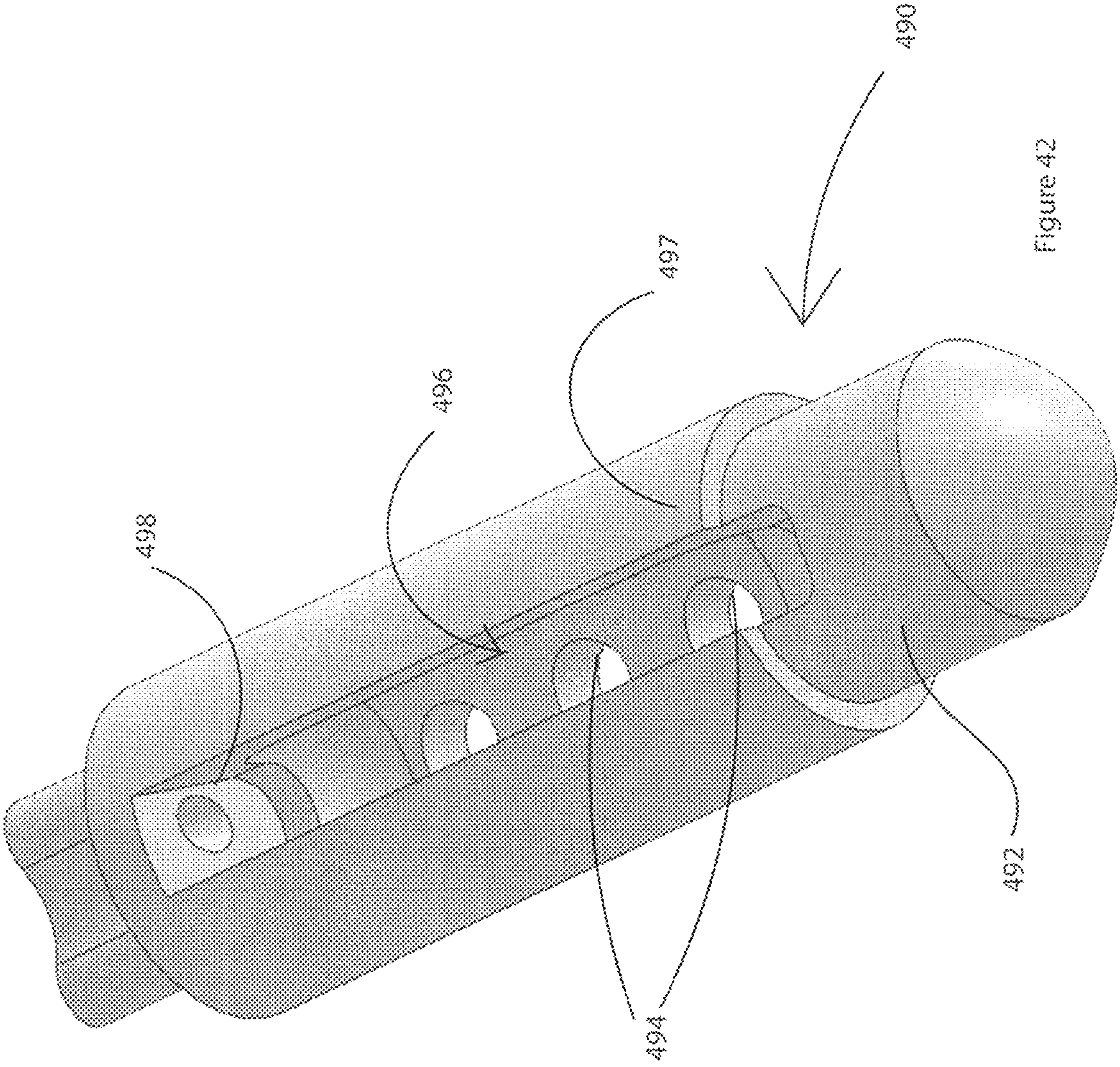
FIG. 42 is a perspective view of an alternate embodiment of the inner balloon chamber.
Figure 43:
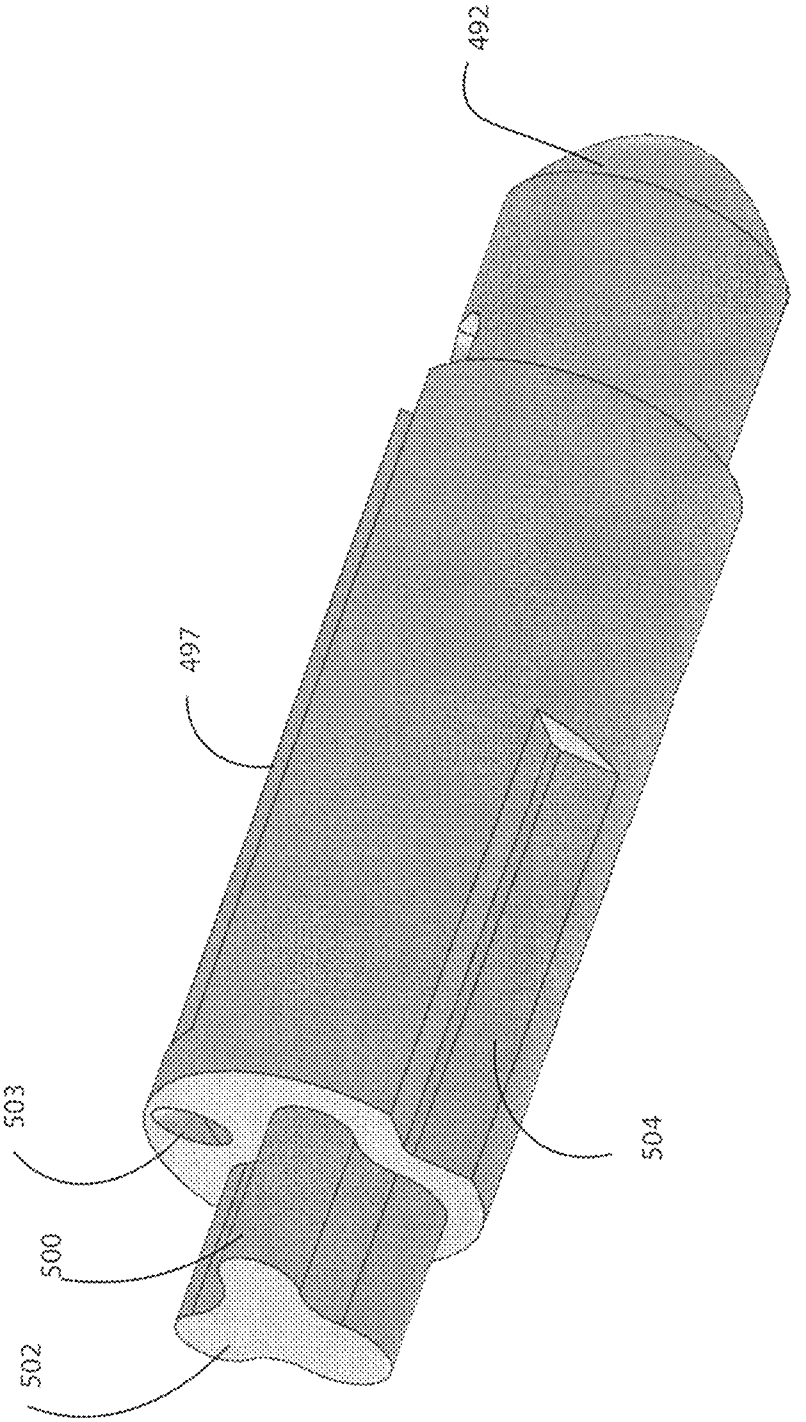
FIG. 43 is a perspective view of the chamber of FIG. 42 from the other side.
Figure 44:
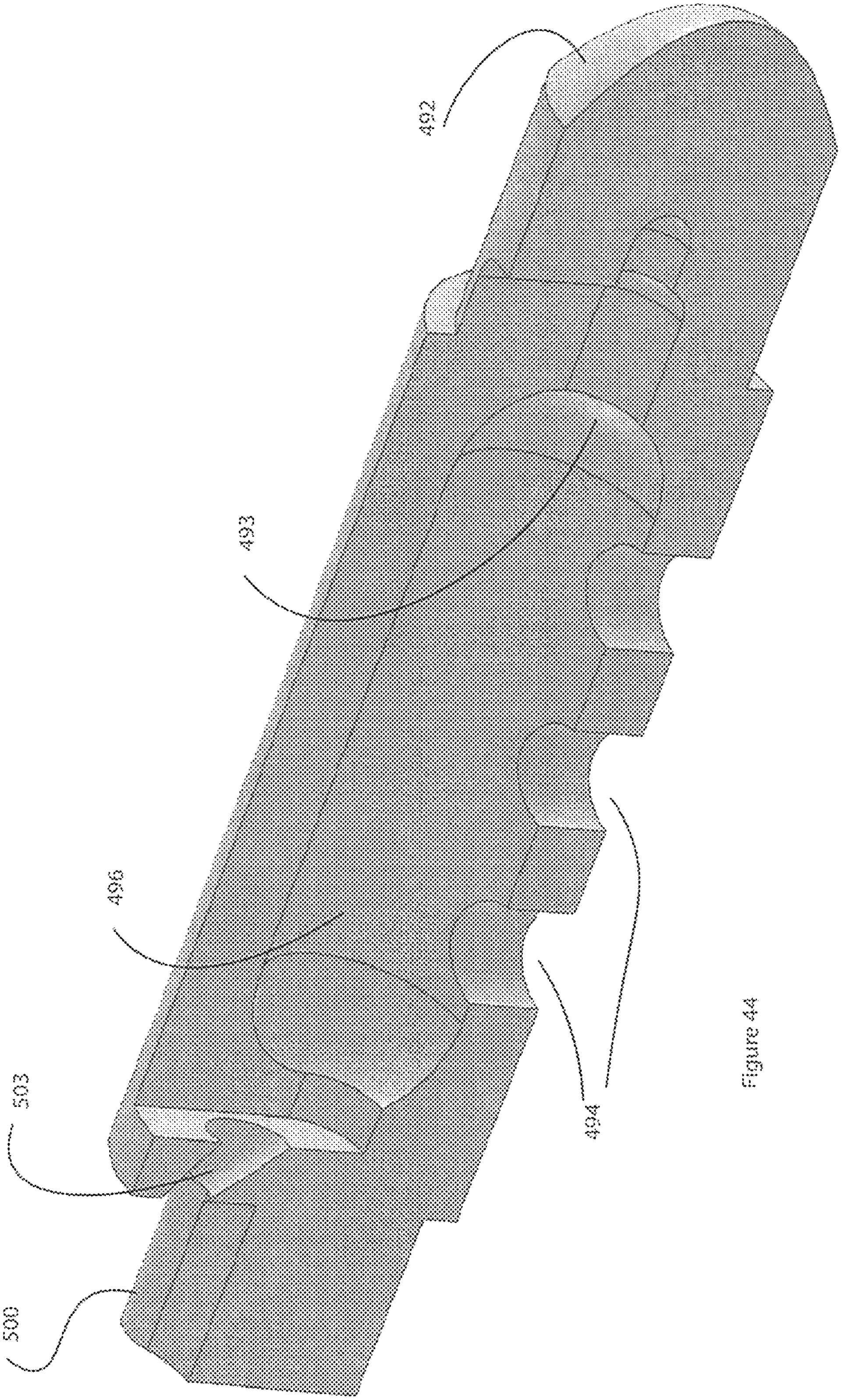
FIG. 44 is a cutaway view of the chamber of FIG. 43.
Figure 45A:
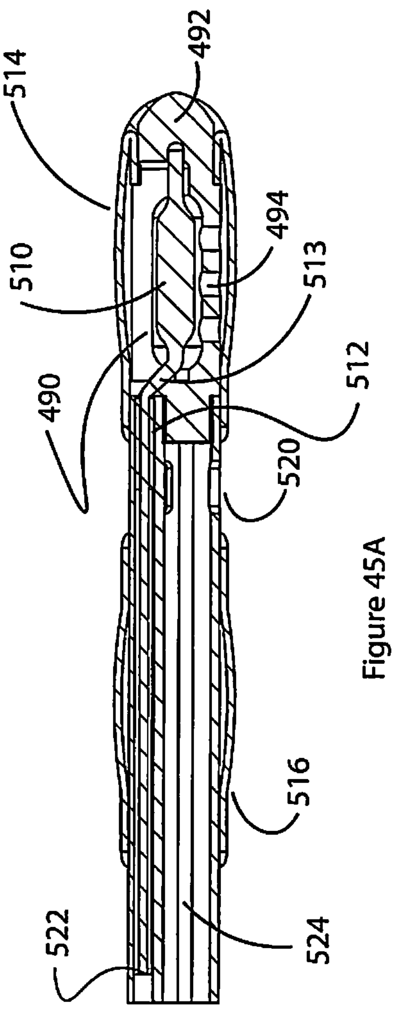
FIG. 45A is a longitudinal cross-sectional view of the distal region of a catheter of an alternate embodiment containing the chamber of FIG. 42.
Figure 45B:
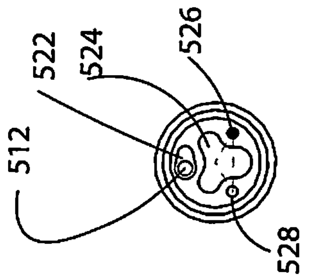
FIG. 45B is a transverse cross-sectional view taken along line A-A of FIG. 45A.
Figure 46A:
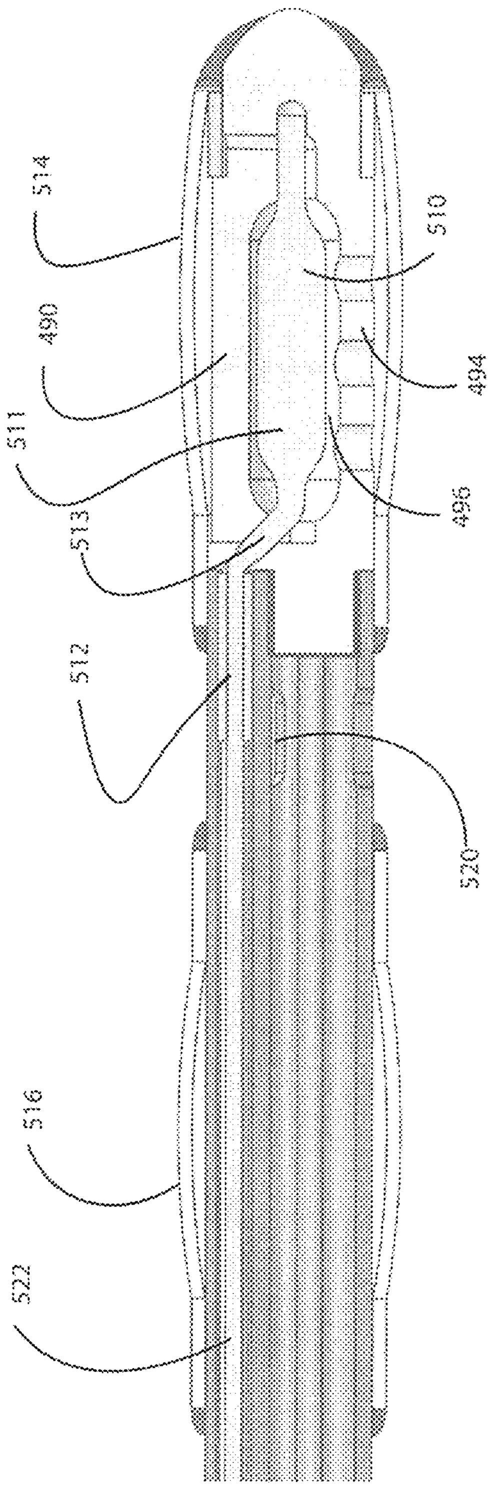
FIG. 46A is a cutaway view similar to the cross-sectional view of FIG. 45A.
Figure 46B:
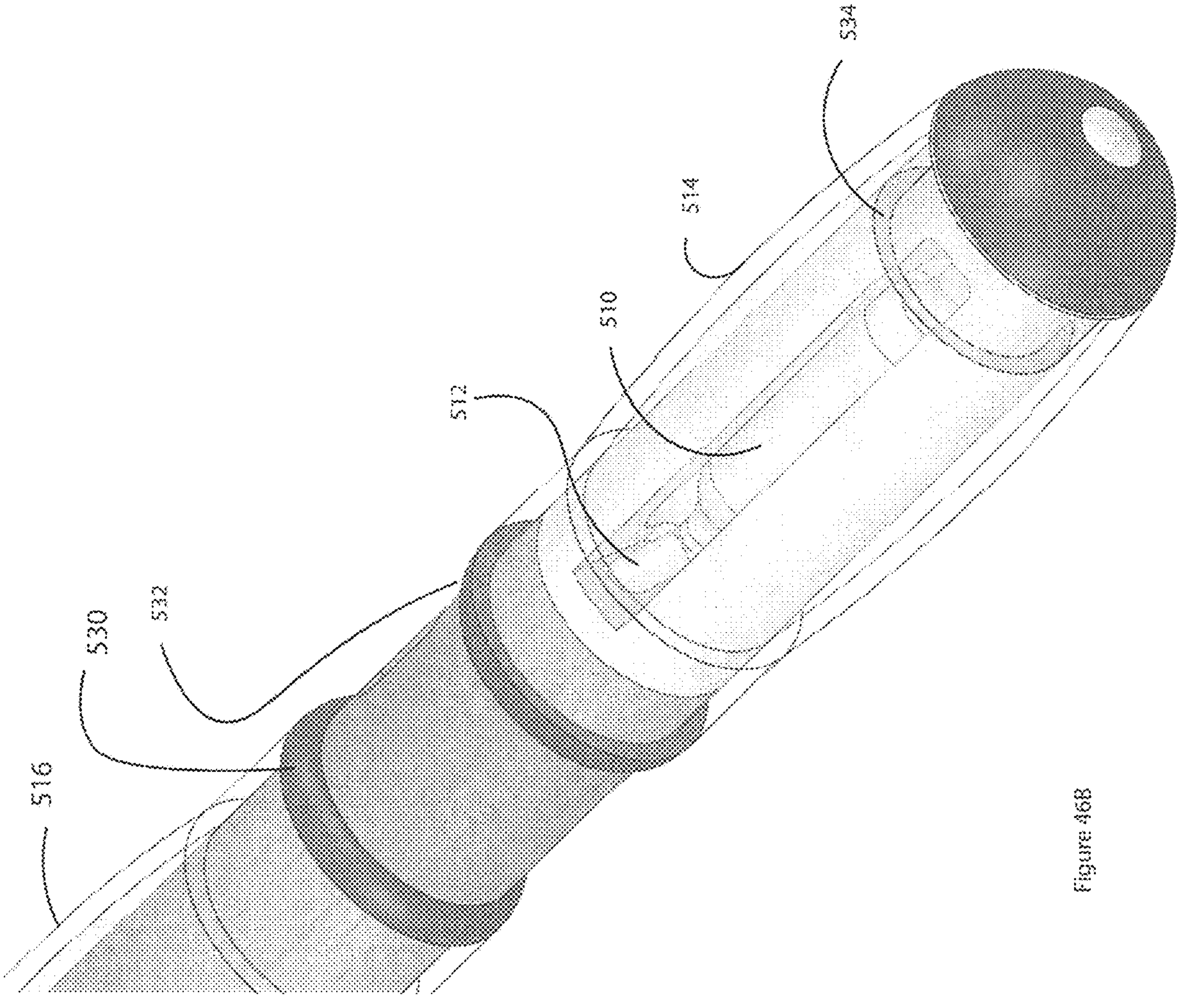
FIG. 46B is a perspective view of the distal end of the catheter of FIG. 46A.
Figure 47A:
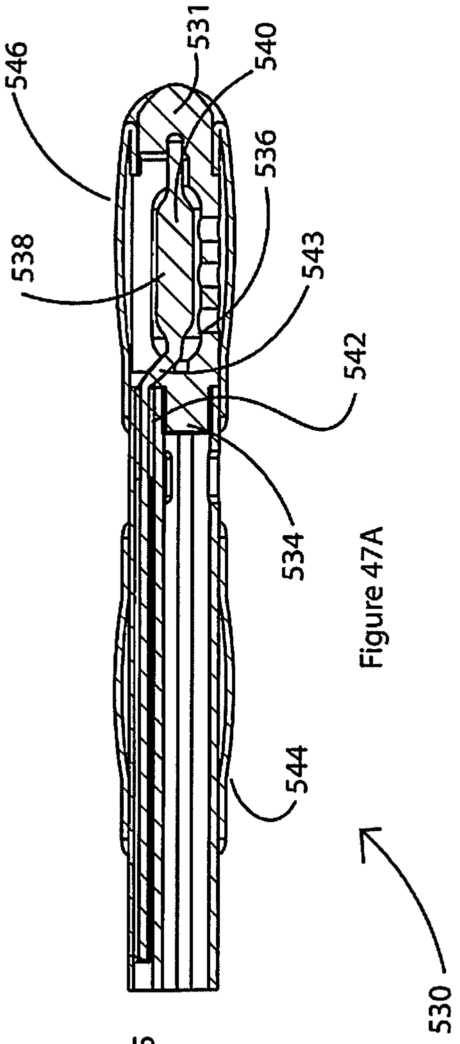
FIG. 47A is a longitudinal cross-sectional view of the distal region of an alternate embodiment of the catheter of the present invention.
Figure 47B:
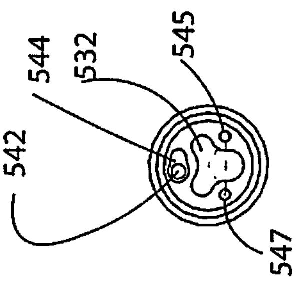
FIG. 47B is a transverse cross-sectional view taken along line A-A of FIG. 47A.
Figure 47C:
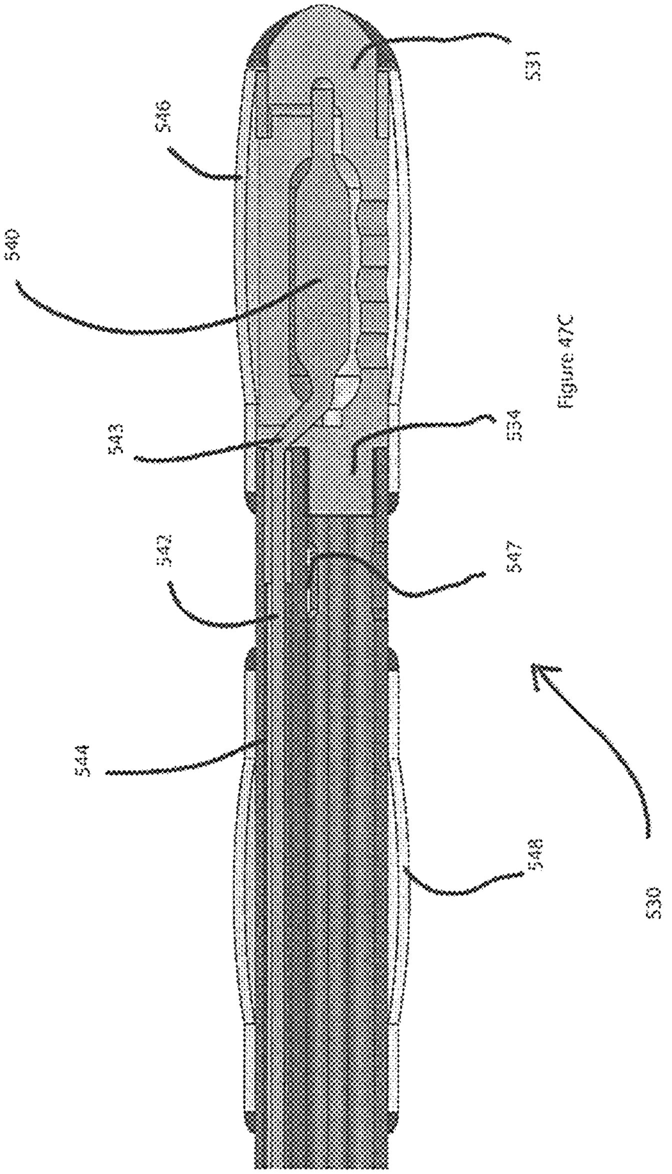
FIG. 47C is a cutaway view similar to the cross-sectional view of FIG. 47A.
Figure 43A:
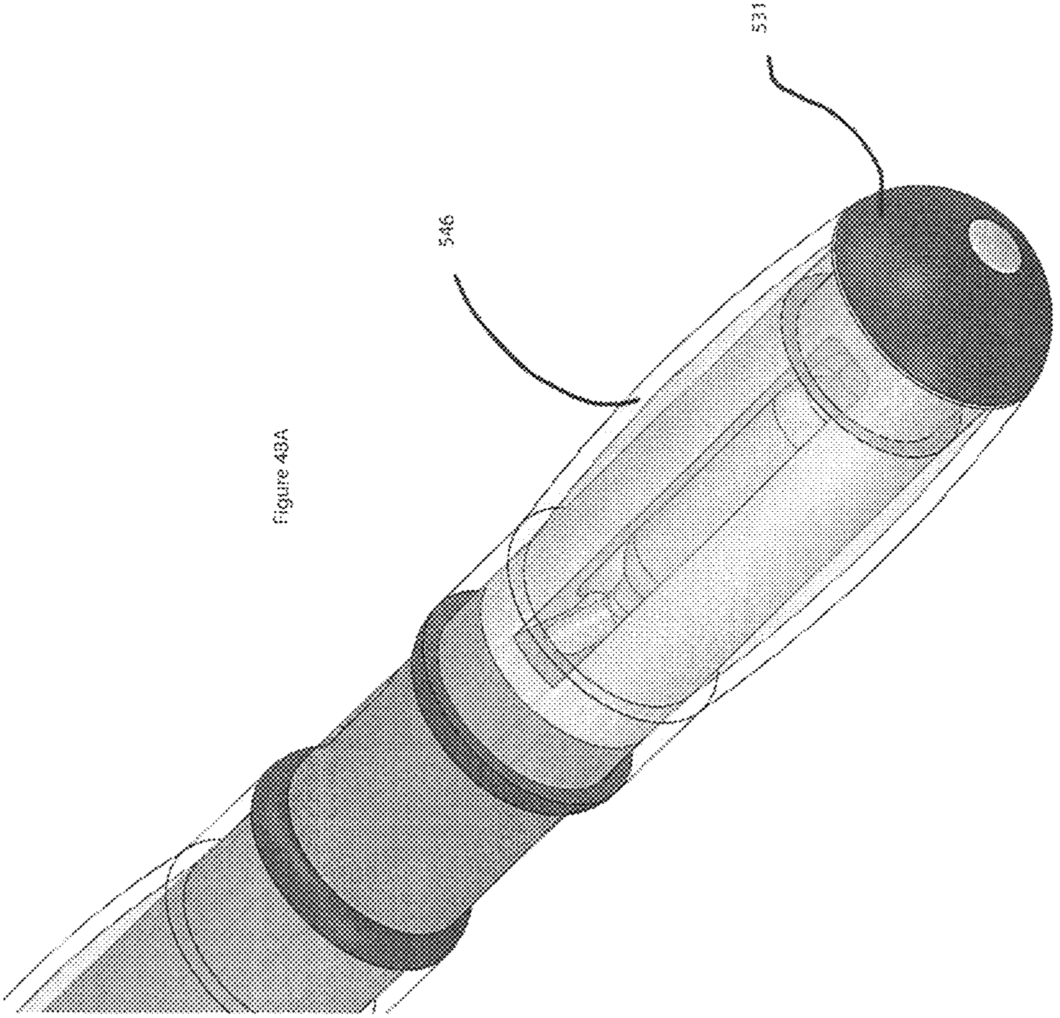
Figure 48B:
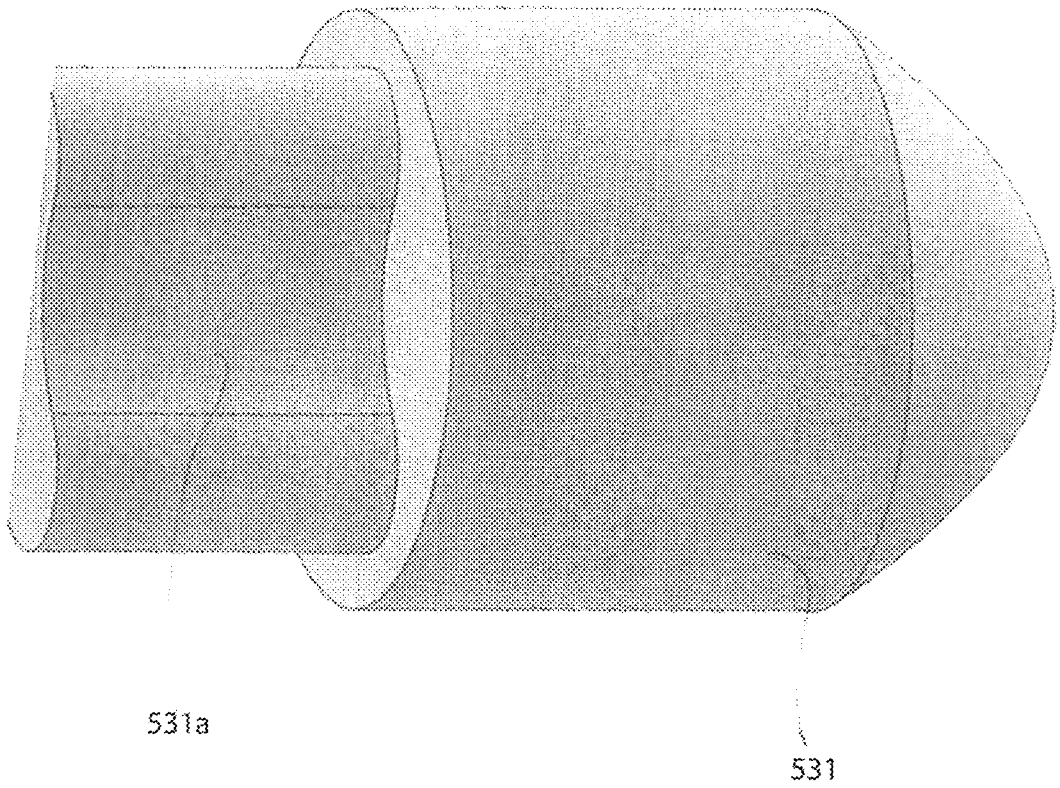
FIG. 48B is a perspective view of the distal tip of the catheter of FIG. 47A.
Figure 48C:
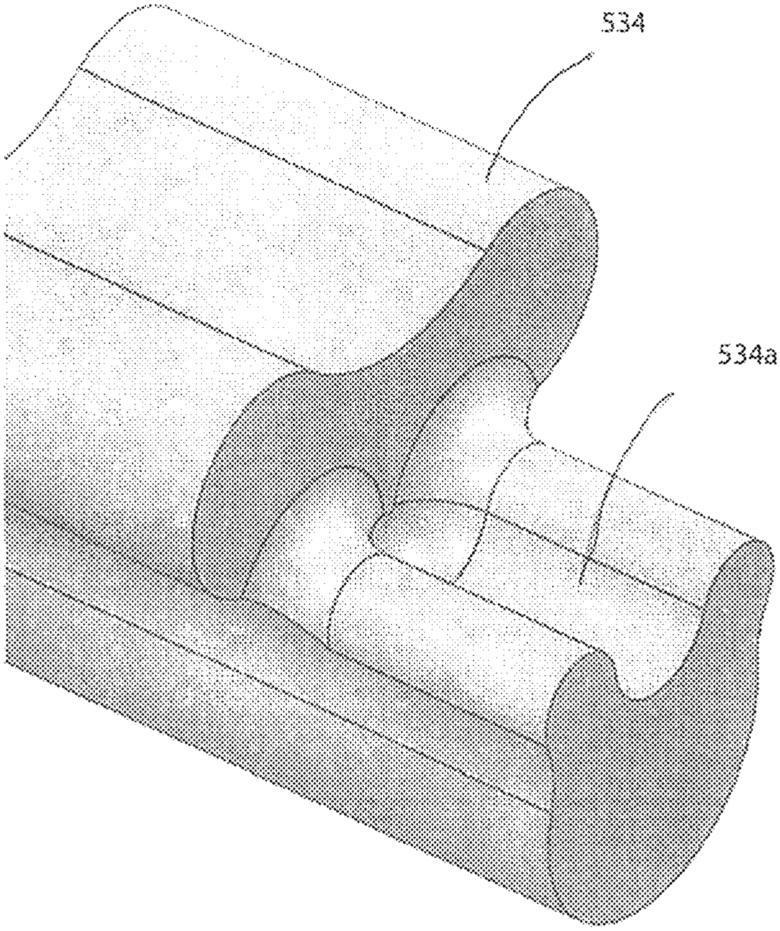
FIG. 48C is a perspective view of the plug of the catheter of FIG. 47A.
Figure 49:
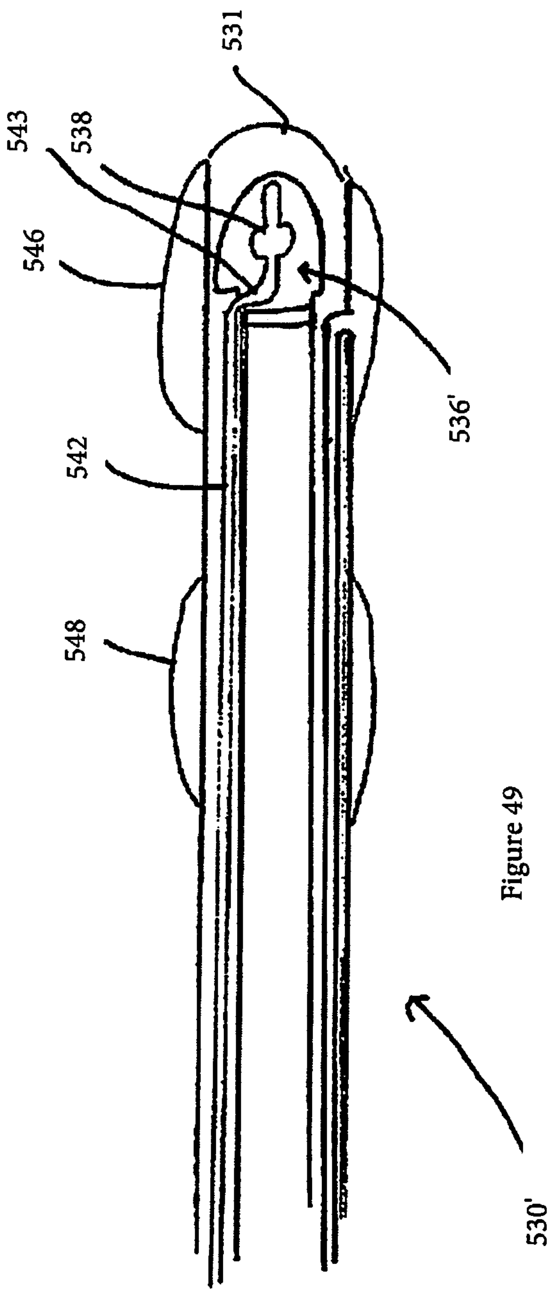
FIG. 49 is a side view of an alternate embodiment of the catheter of the present invention.
Figure 50A:
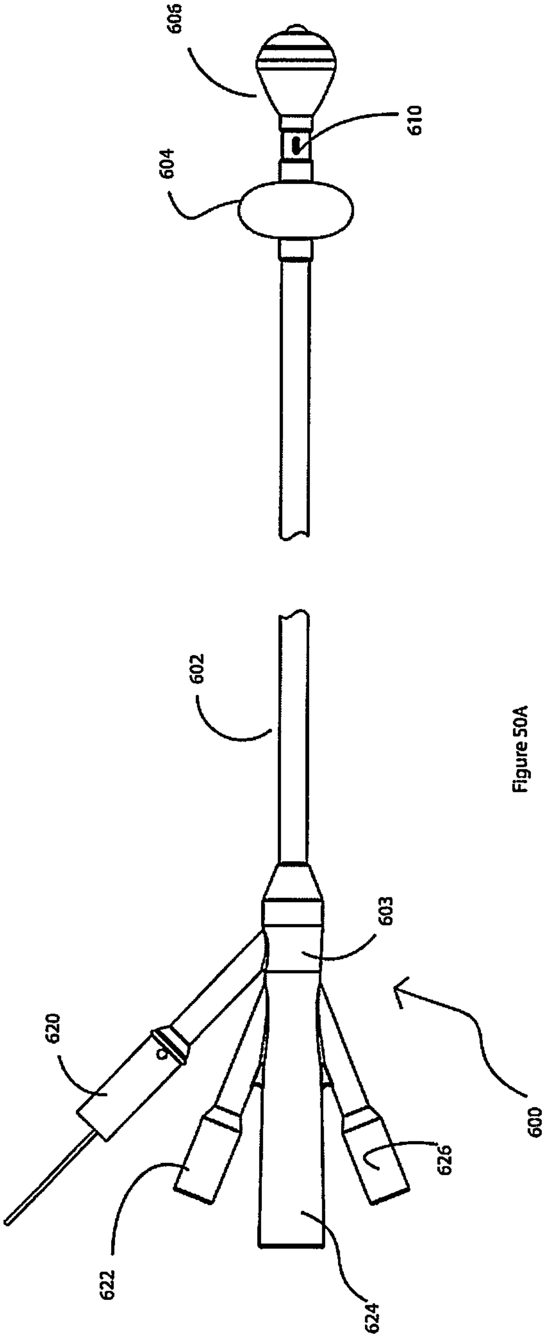
FIG. 50A is a side view of an alternate embodiment of the catheter of the present invention showing the balloons in the inflated condition.
Figure 50B:
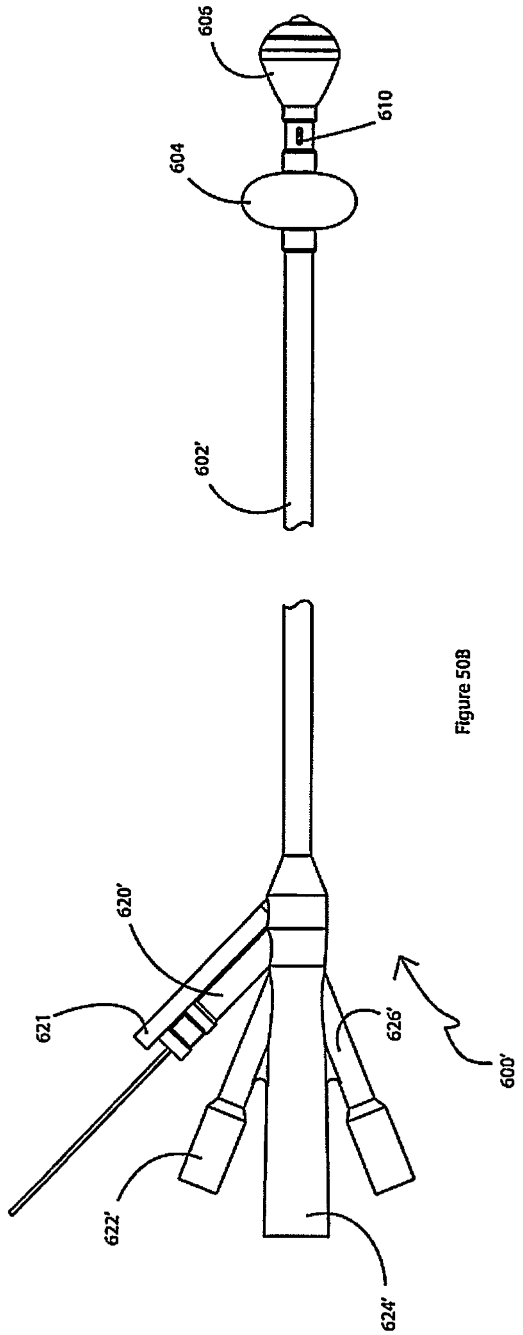
FIG. 50B is a side view of an alternate embodiment of the catheter of FIG. 50A having an additional port for the thermistor wires.
Figure 50C:
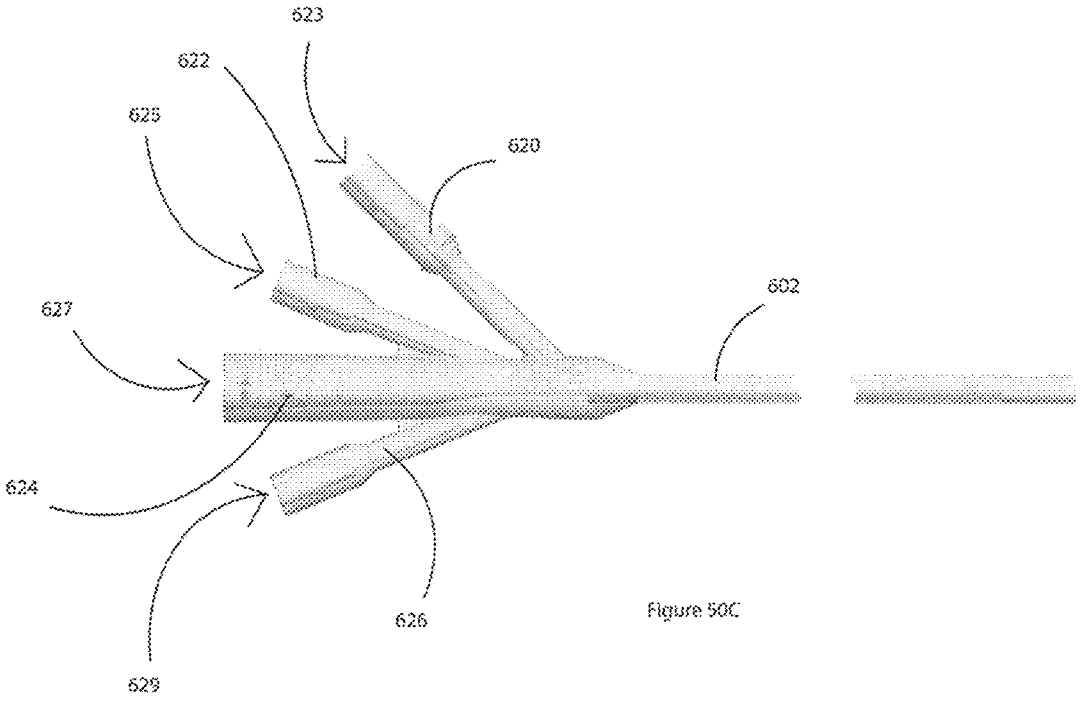
FIG. 50C is a side view of the proximal portion of the catheter of FIG. 50A.
Figure 51:
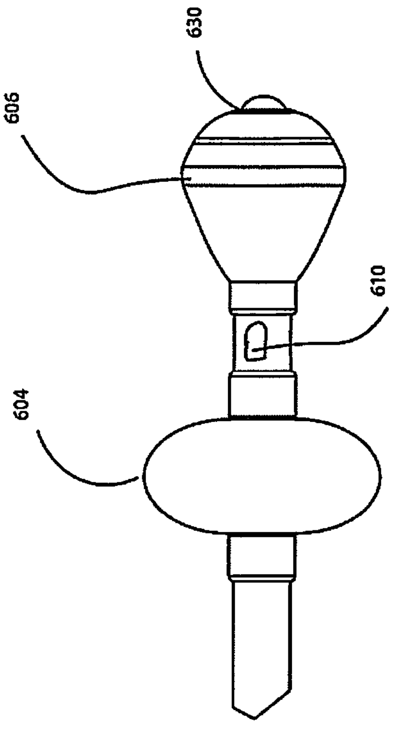
FIG. 51 is a close up view of the distal end of the catheter of FIG. 50A with the balloons in the inflated condition.
Figure 53:
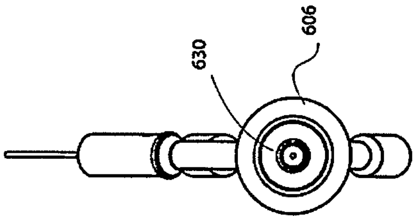
FIG. 53 is a front view of the catheter of FIG. 50A.
Figure 52:
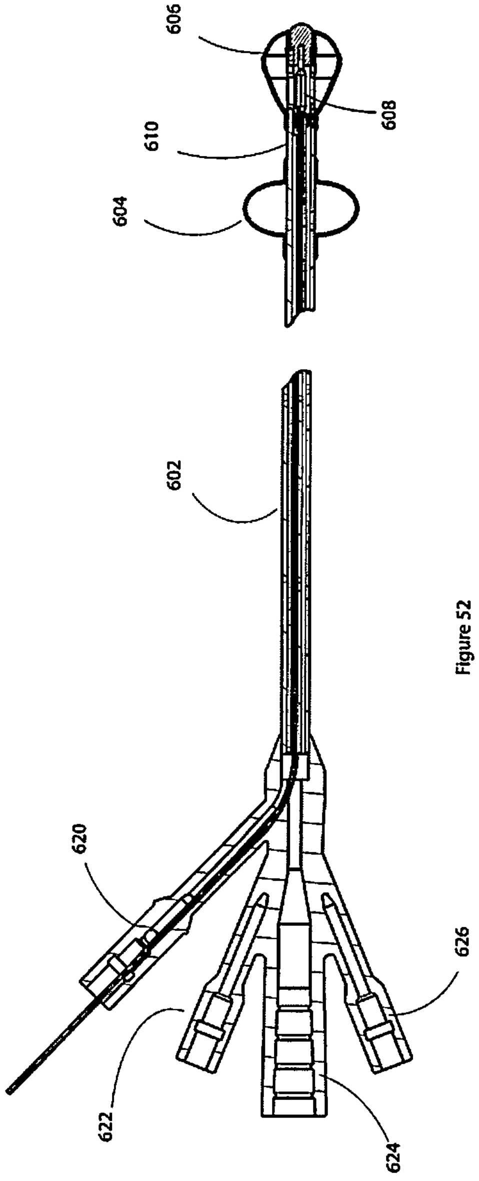
FIG. 52 is a cross-sectional view of the catheter of FIG. 50A.
Figure 54:
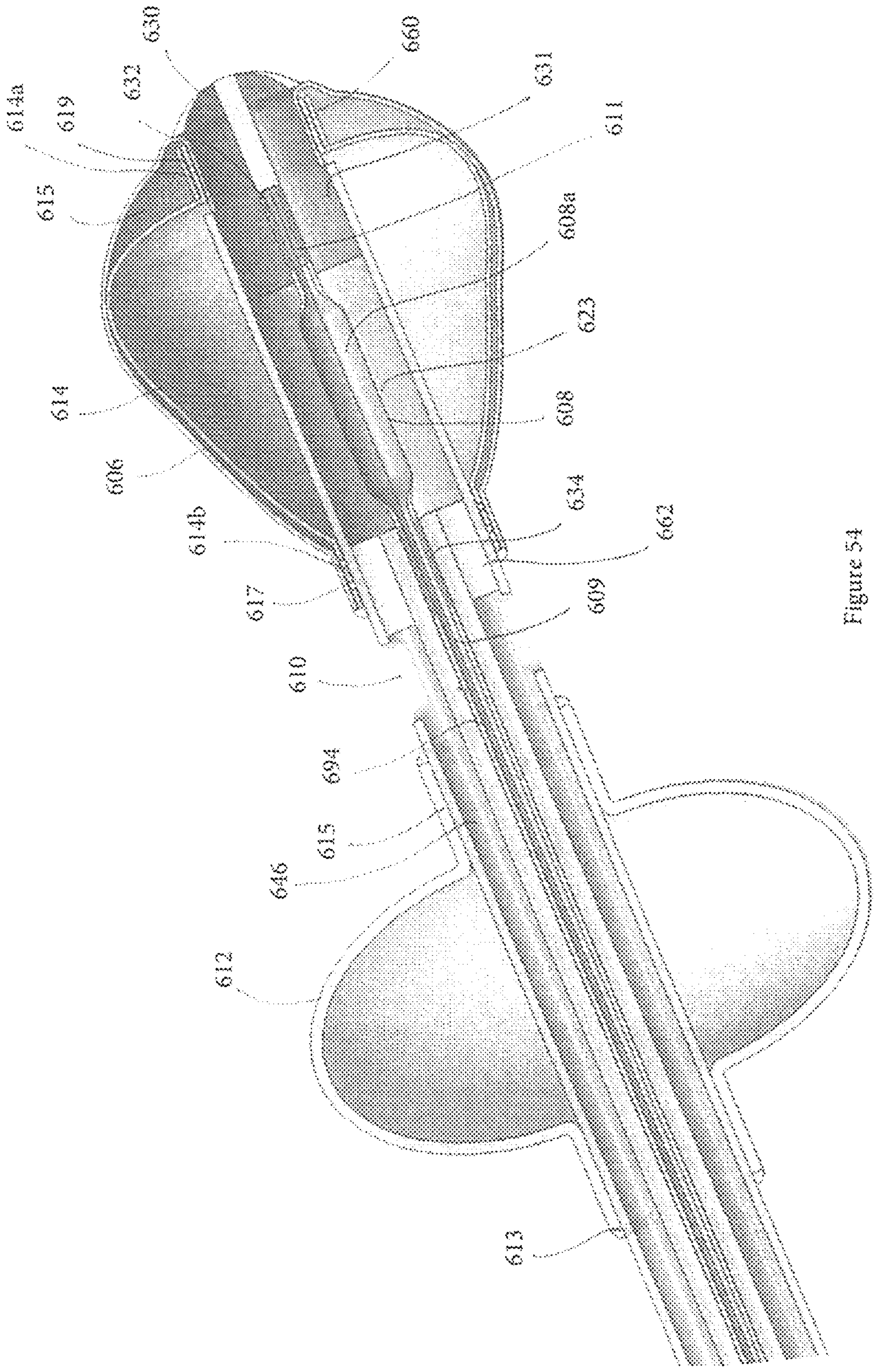
FIG. 54 is a cutaway side view illustrating the inside of a catheter similar to the catheter of FIG. 50A.
Figure 55:
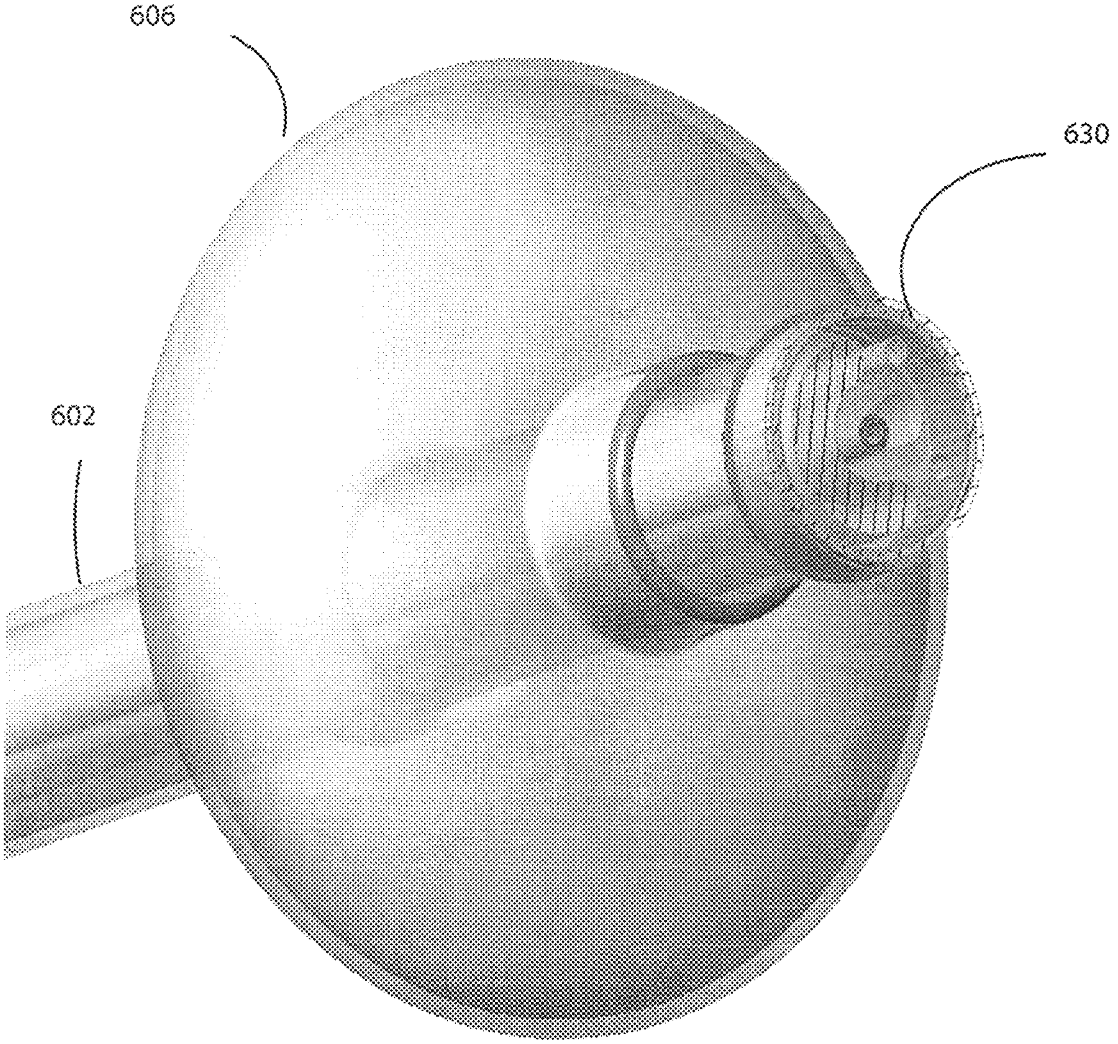
FIG. 55 is an enlarged view of the distal tip of the catheter of FIG. 50A.
Figures 56, 57, 58A, 58B, 58C, 58D:
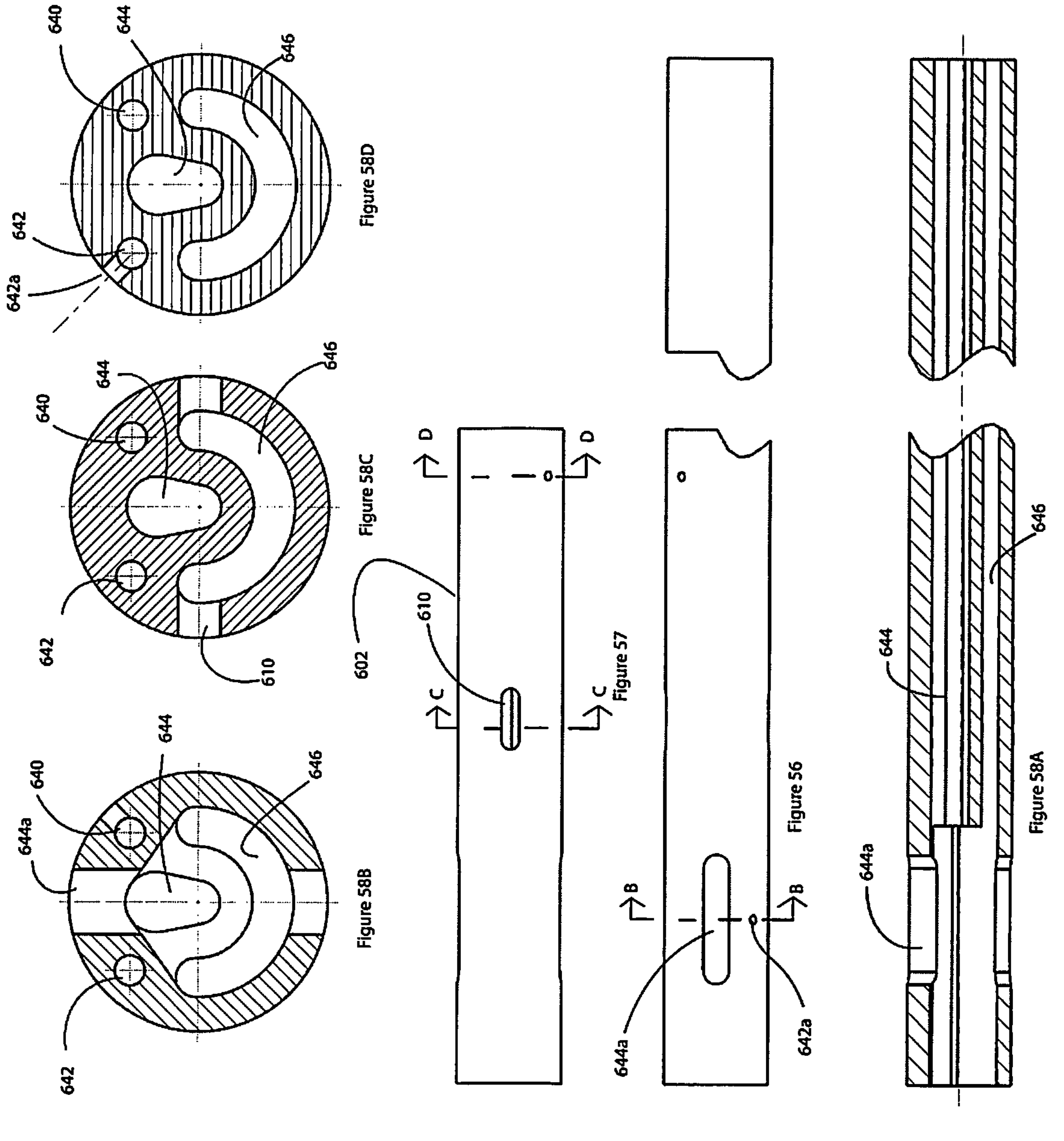
FIG. 56 is a side view of a portion of the shaft of the catheter of FIG. 50A showing the openings for communicating with the outer wall of the inner balloon.
FIG. 57 is a side view of a portion of the shaft of the catheter of FIG. 50A showing the drainage opening.
FIG. 58A is a longitudinal cross-sectional view of the catheter shaft of FIG. 56.
FIG. 58B is a transverse cross-sectional view taken along line B-B of FIG. 56.
FIG. 58C is a transverse cross-sectional view taken along line C-C of FIG. 57.
FIG. 58D is a transverse cross-sectional view taken along line D-D of FIG. 57.
Figure 59A:
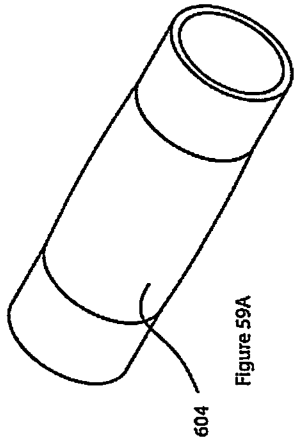
FIG. 59A is a perspective view of the retention balloon of the catheter of FIG. 50A.
Figure 59B:
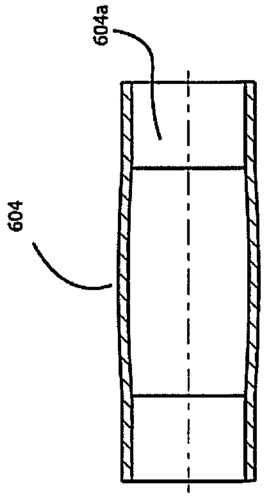
FIG. 59B is a cross-sectional view of the retention balloon of FIG. 59A.
Figure 60A:
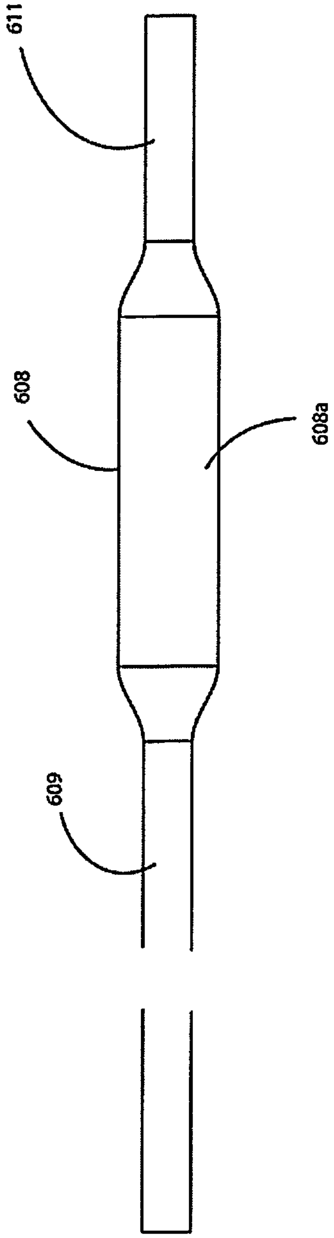
FIG. 60A is a side view of the inner balloon of the catheter of FIG. 50A.
Figure 60C:
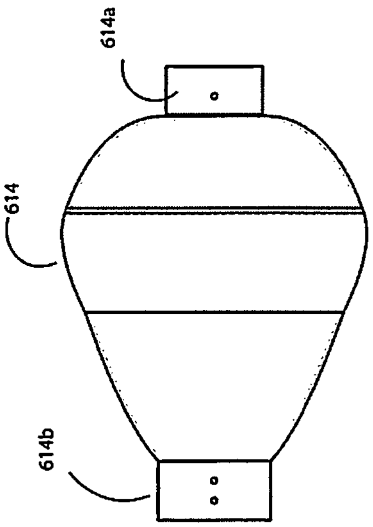
FIG. 60C is a side view of the intermediate balloon (inner liner) of the catheter of FIG. 50A.
Figure 61B:
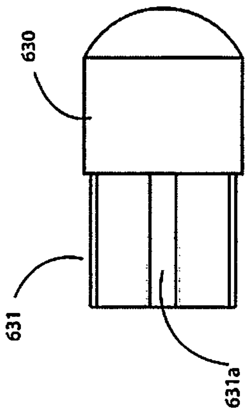
FIGS. 61A and 61B are side views of the distal tip of the catheter of FIG. 50A.
Figure 60B:
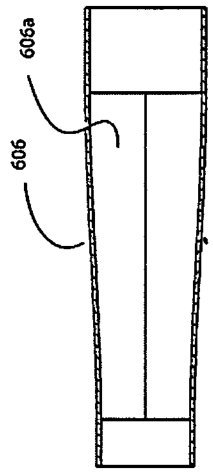
FIG. 60B is a side view of the distal outer balloon of the catheter of FIG. 50A.
Figure 61A:
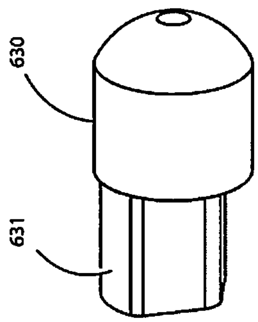
Figure 60D:
FIG. 60D is a side view of an insert for the inner balloon in accordance with an alternate embodiment.
Figure 63A:
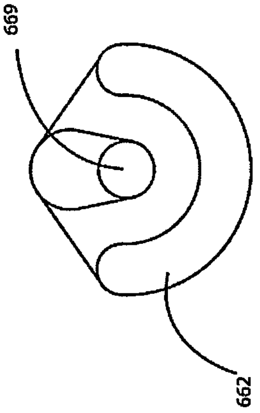
FIG. 63A is a front view of the proximal plug of the catheter of FIG. 50A.
Figure 63B:
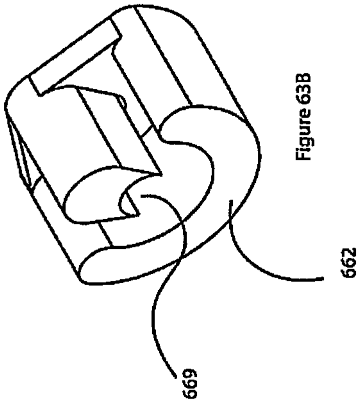
FIG. 63B is a perspective view of the proximal plug of FIG. 63A.
Figure 62:
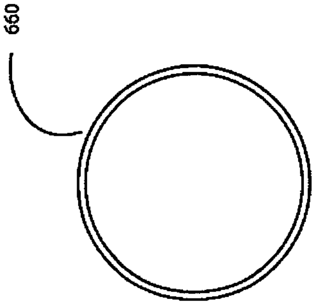
FIG. 62 is a front view of the distal inner sleeve of the catheter of FIG. 50A.
Figure 64:
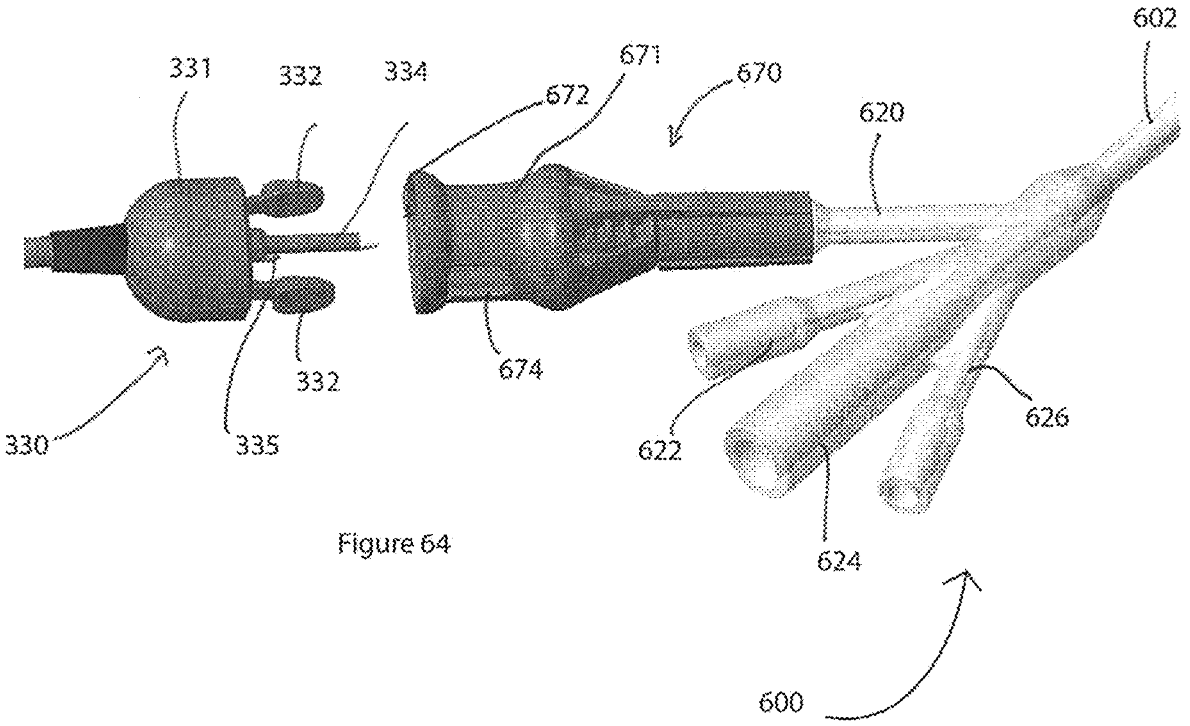
FIG. 64 is a perspective view of an alternate embodiment of the hub and connector of the present invention.
Figure 65:
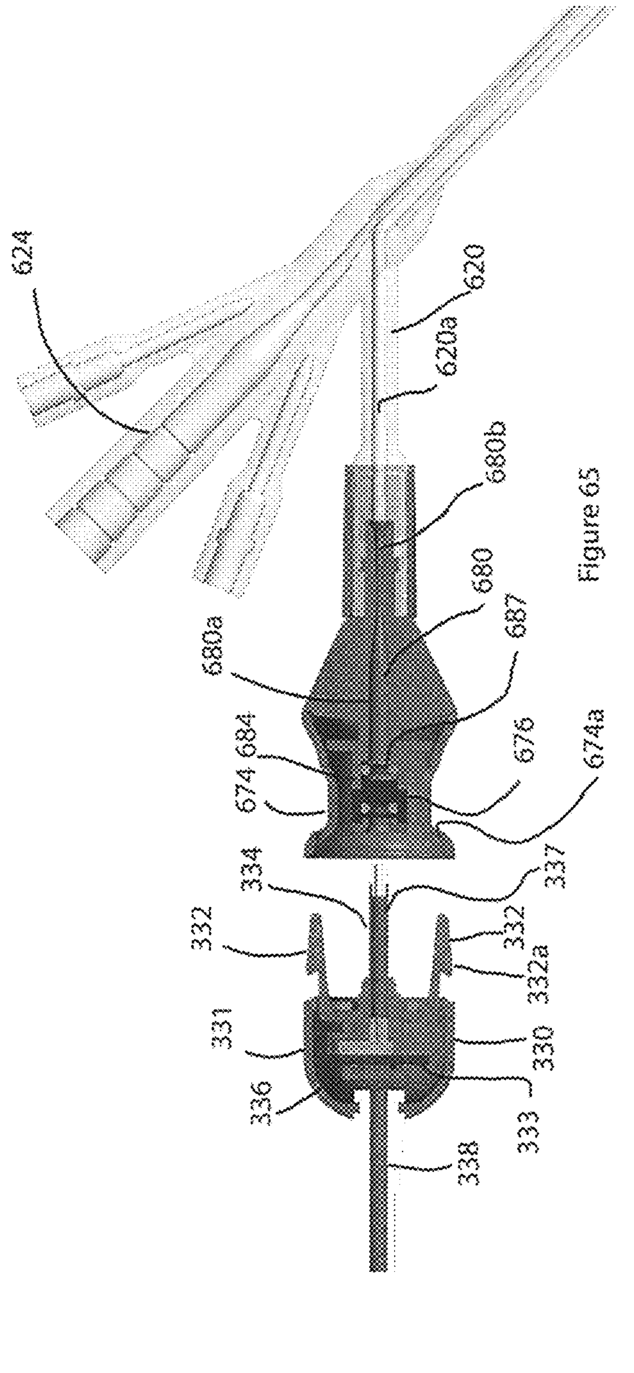
FIG. 65 is a cutaway side view of the hub and connector of FIG. 64.
Figure 66A:
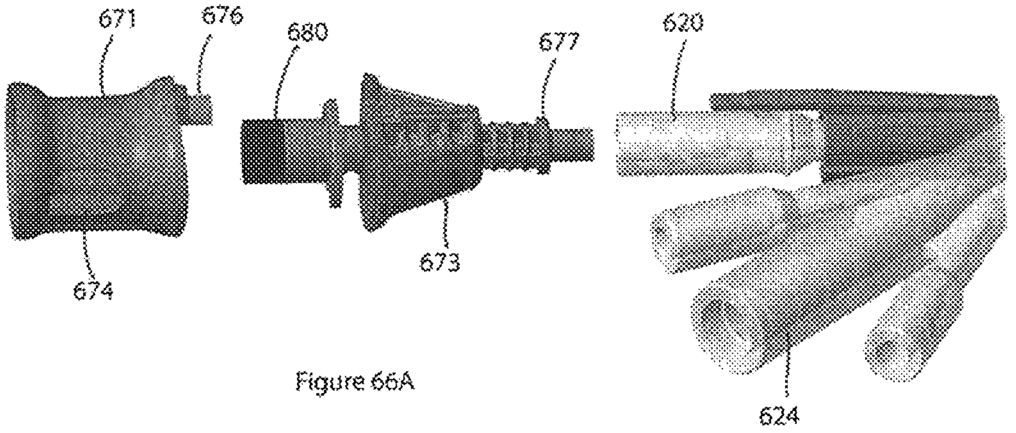
FIG. 66A is an exploded perspective view of a hub and connector of FIG. 64.
Figure 66B:
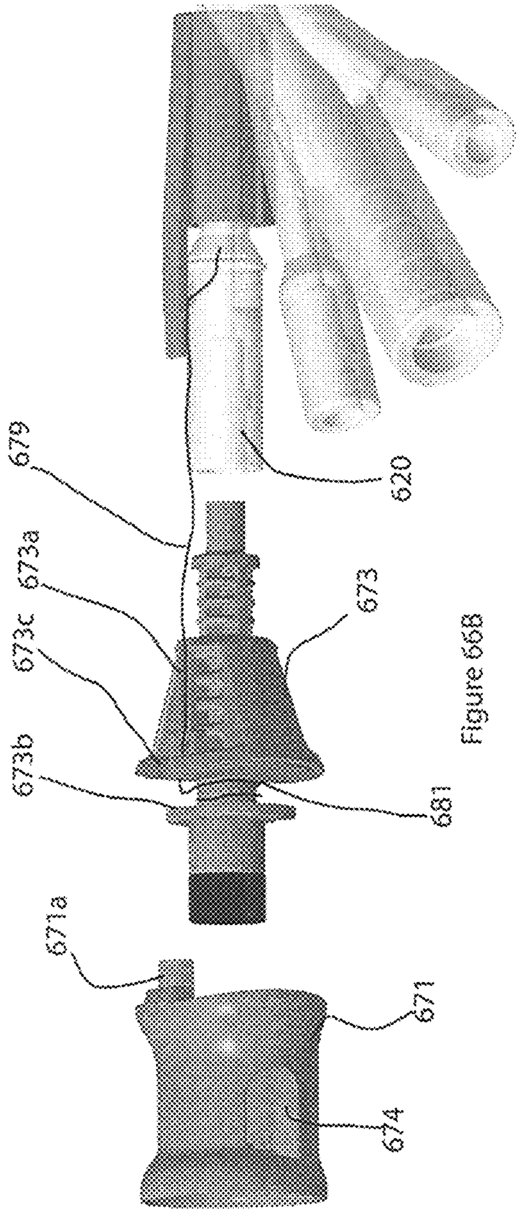
FIG. 66B is an exploded perspective view of the connector showing the thermistor wires.
Figure 66C:
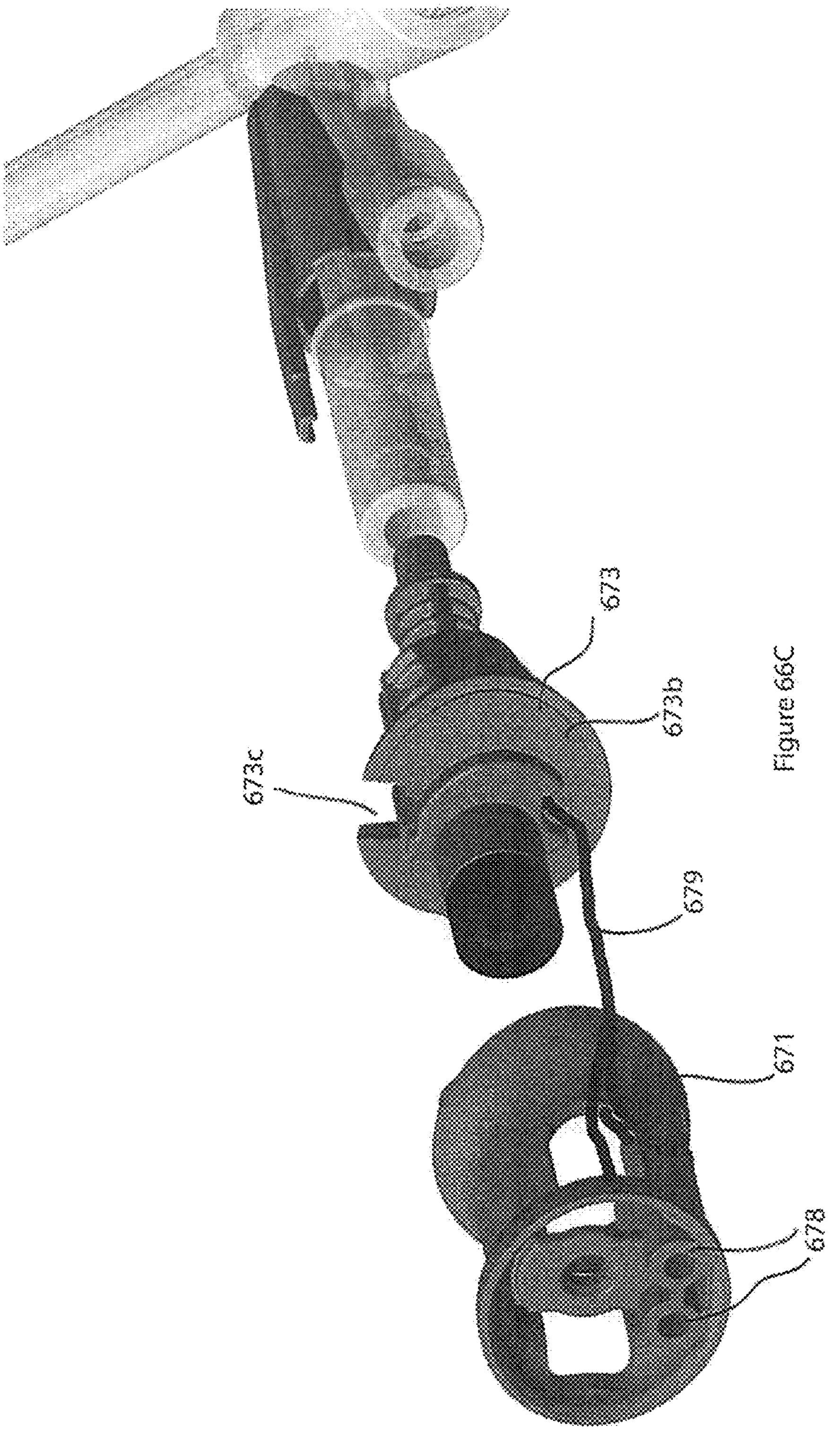
FIG. 66C is an exploded perspective of the connector of FIG. 64 showing the thermistor wires.
Figure 67:
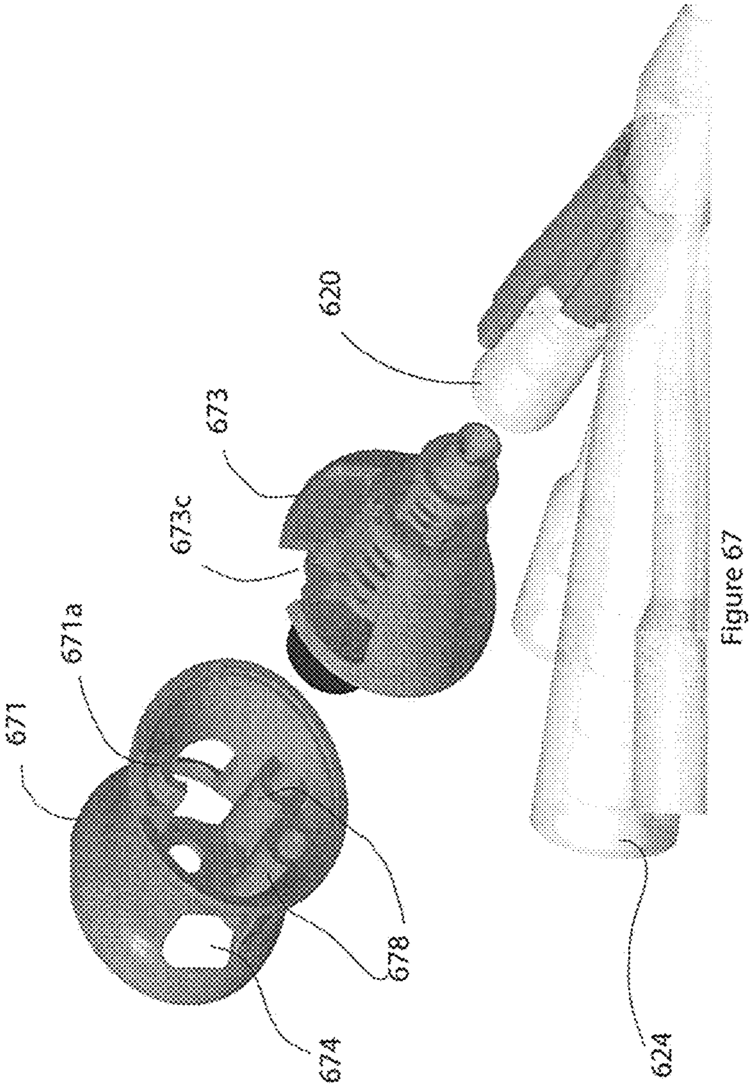
FIGS. 67 and 68 are exploded perspective views of the hub and connector of FIG. 64.
Figure 68:
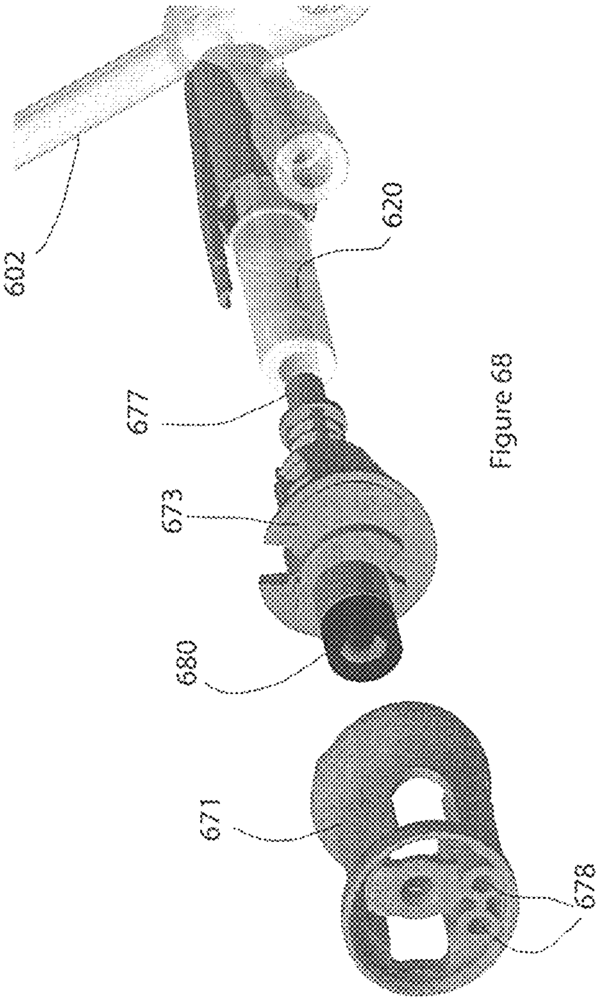

In some embodiments, the outer balloon 406 is folded over itself as shown in FIG. 34 to allow the balloon 406 when inflated to extend out and fully cover the distal tip 412. Thus, the outer balloon 406 in its deflated condition has a distal cuff 411 which exposes the distal tip 412 for atraumatic insertion of the catheter 400, and expands to cover the distal tip 412 when inflated when the catheter 400 is fully inserted and placed at the target location. The balloons 404, 406 and 408 can be of the various shapes of the stabilizing, outer and inner balloons disclosed herein. In FIGS. 30A to 34 the outer balloon 406 by way of example is shown as pear shaped.

Figure 28A:
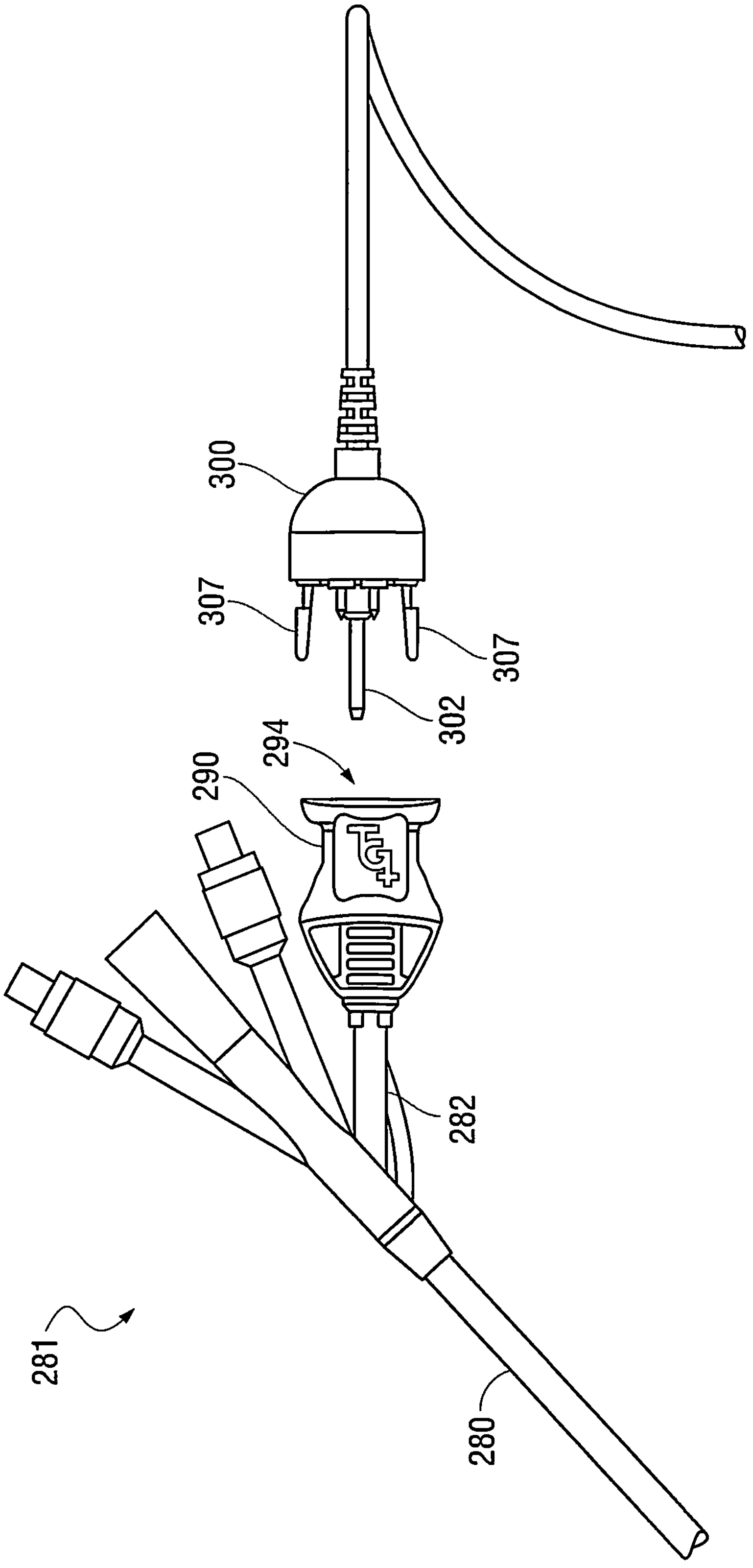
FIG. 28A is a perspective view of an alternate embodiment of the transducer hub and connector.
Figure 28B:
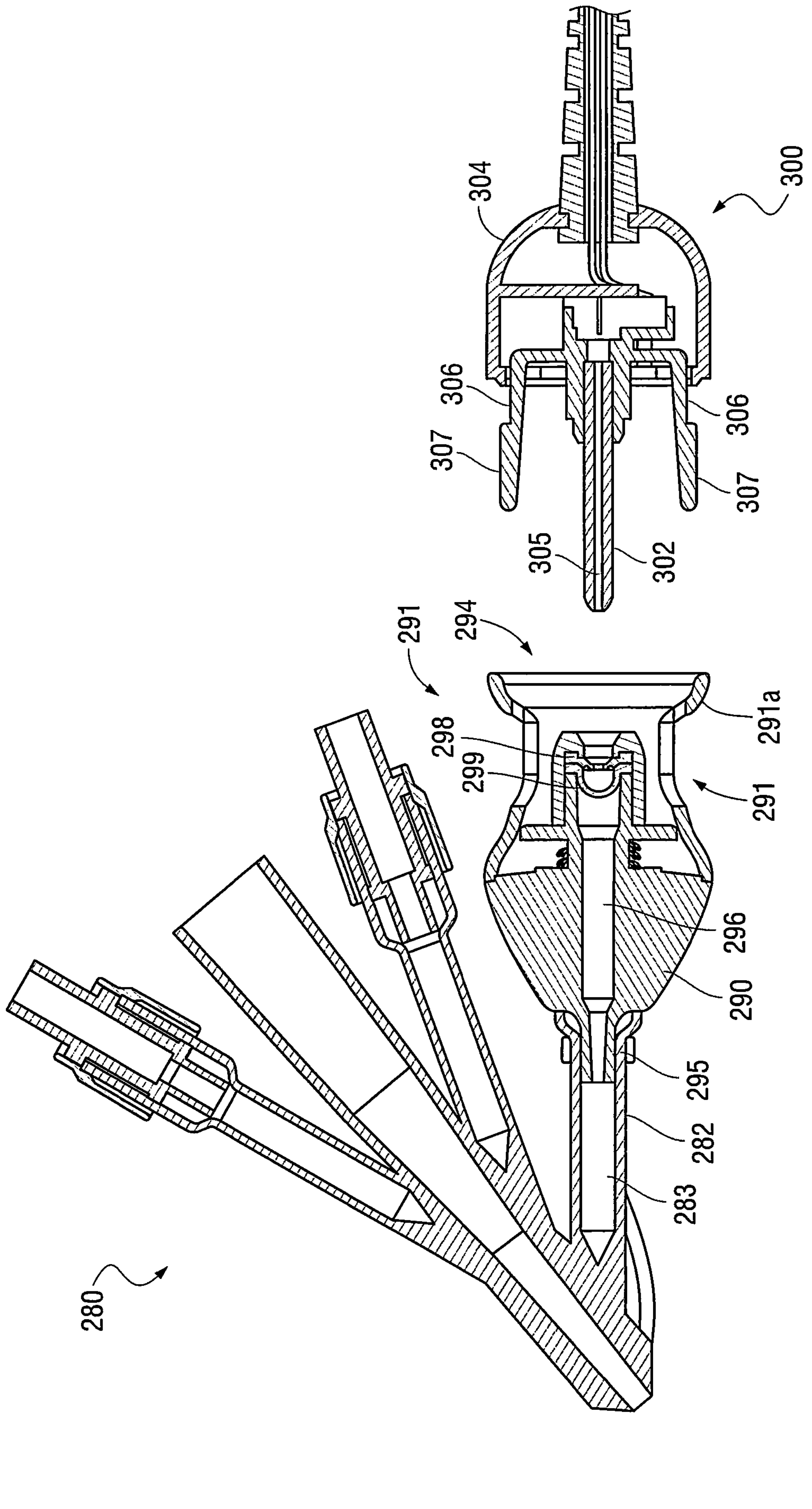
FIG. 28B is a cutaway side view of the hub and connector of FIG. 28A showing the pressure transducer prior to connection to the catheter of FIG. 18A, a portion of the hub wall and connector removed to show internal components.
Figure 28C:
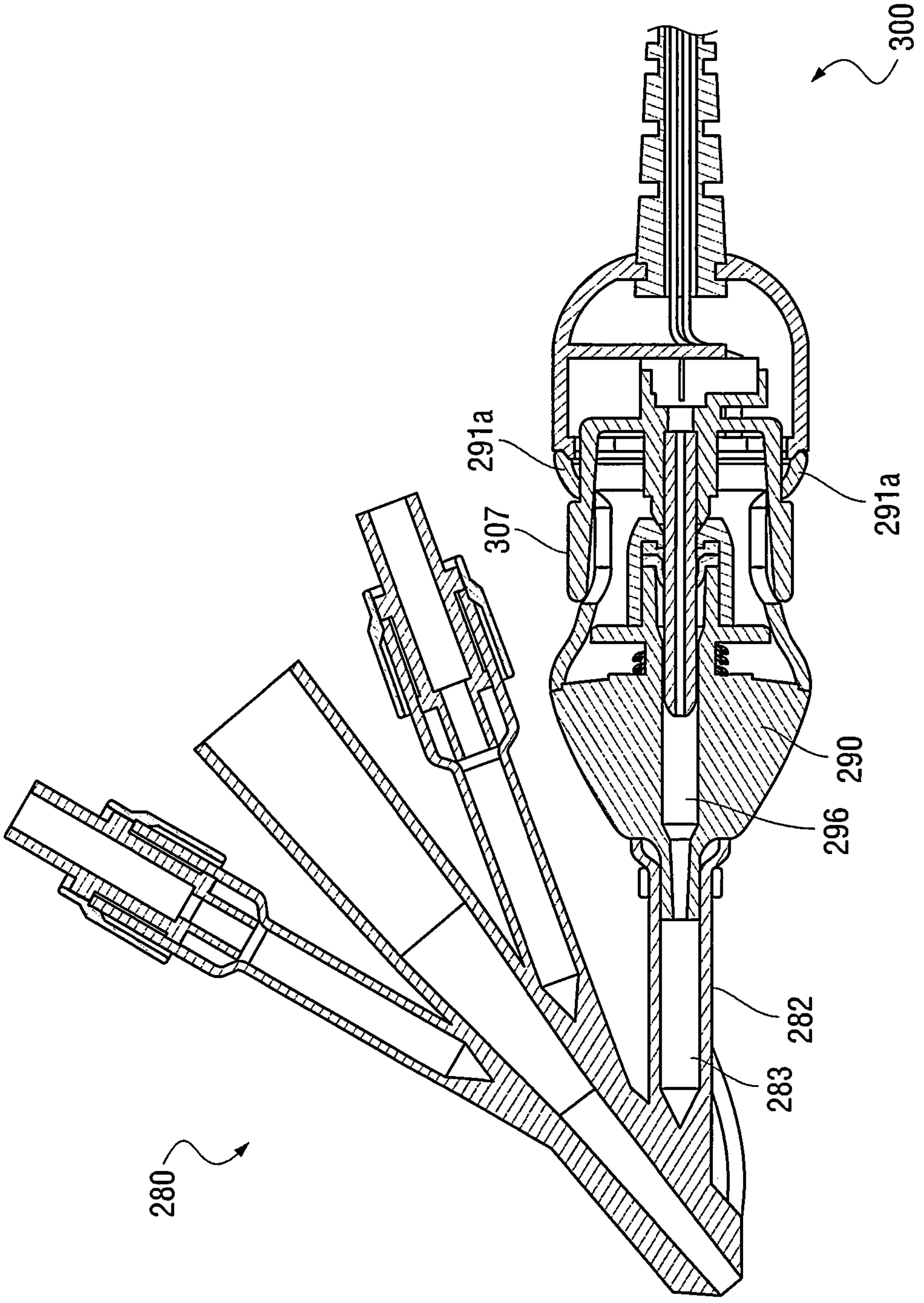
FIG. 28C is a cutaway side view similar to FIG. 28B showing the hub attached to the catheter.
Figure 28D:
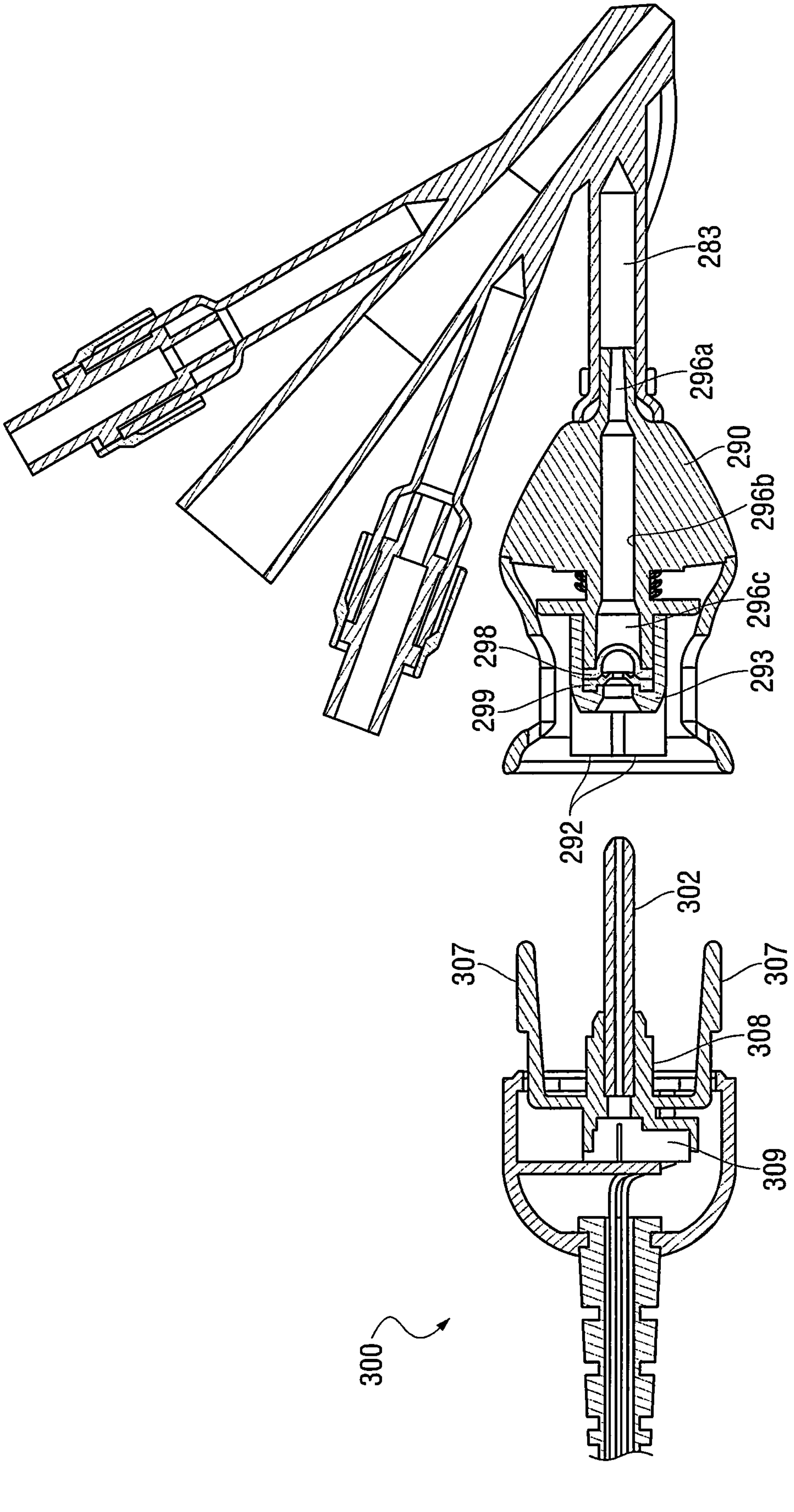
FIG. 28D is a cutaway side view similar to FIG. 28B from the other side.
Figure 29A:
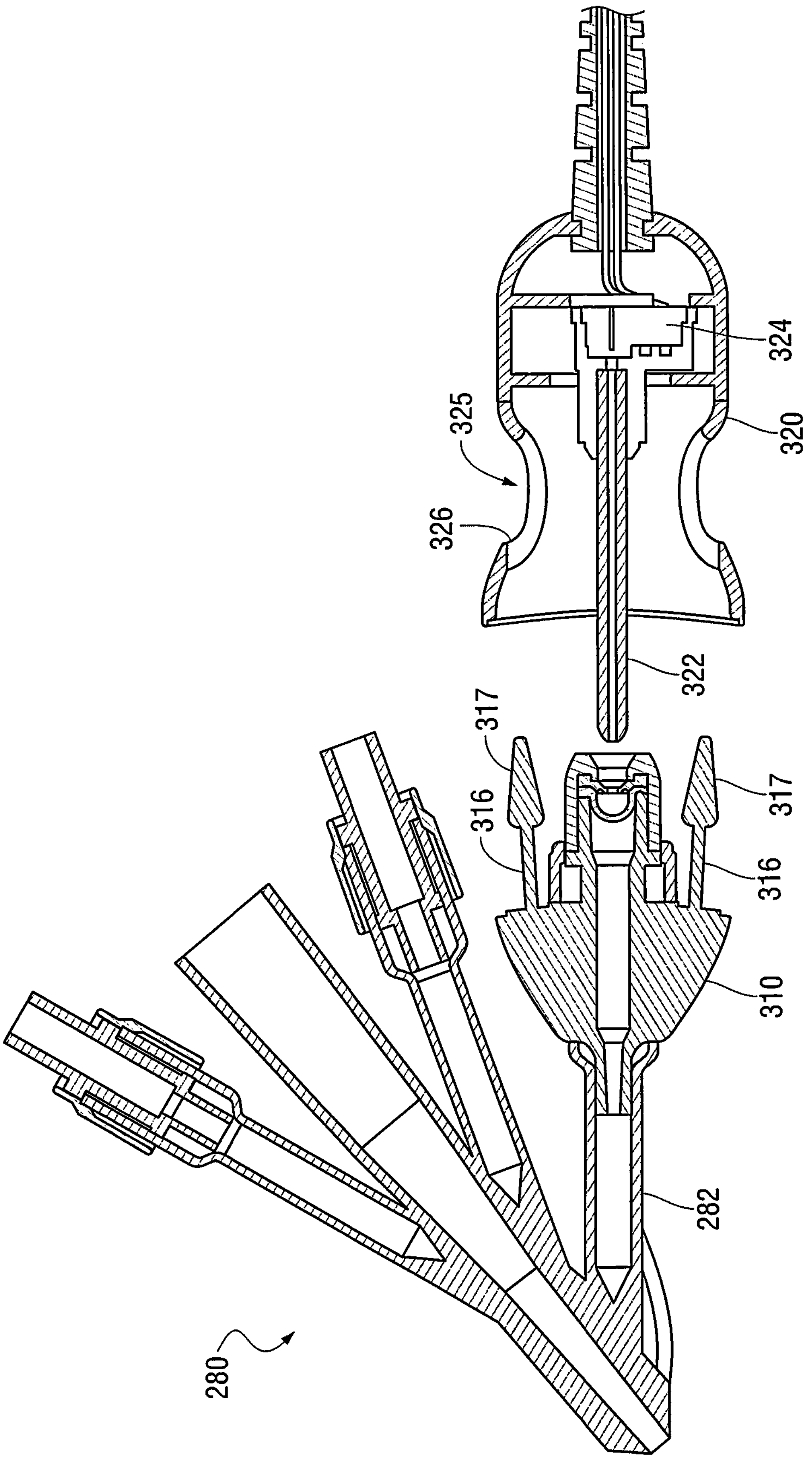
FIG. 29A is a cutaway side view of the hub and connector of an alternate embodiment showing the pressure transducer prior to connection to the catheter of FIG. 18A, a portion of the hub wall and catheter connector removed to show internal components
Figure 29B:
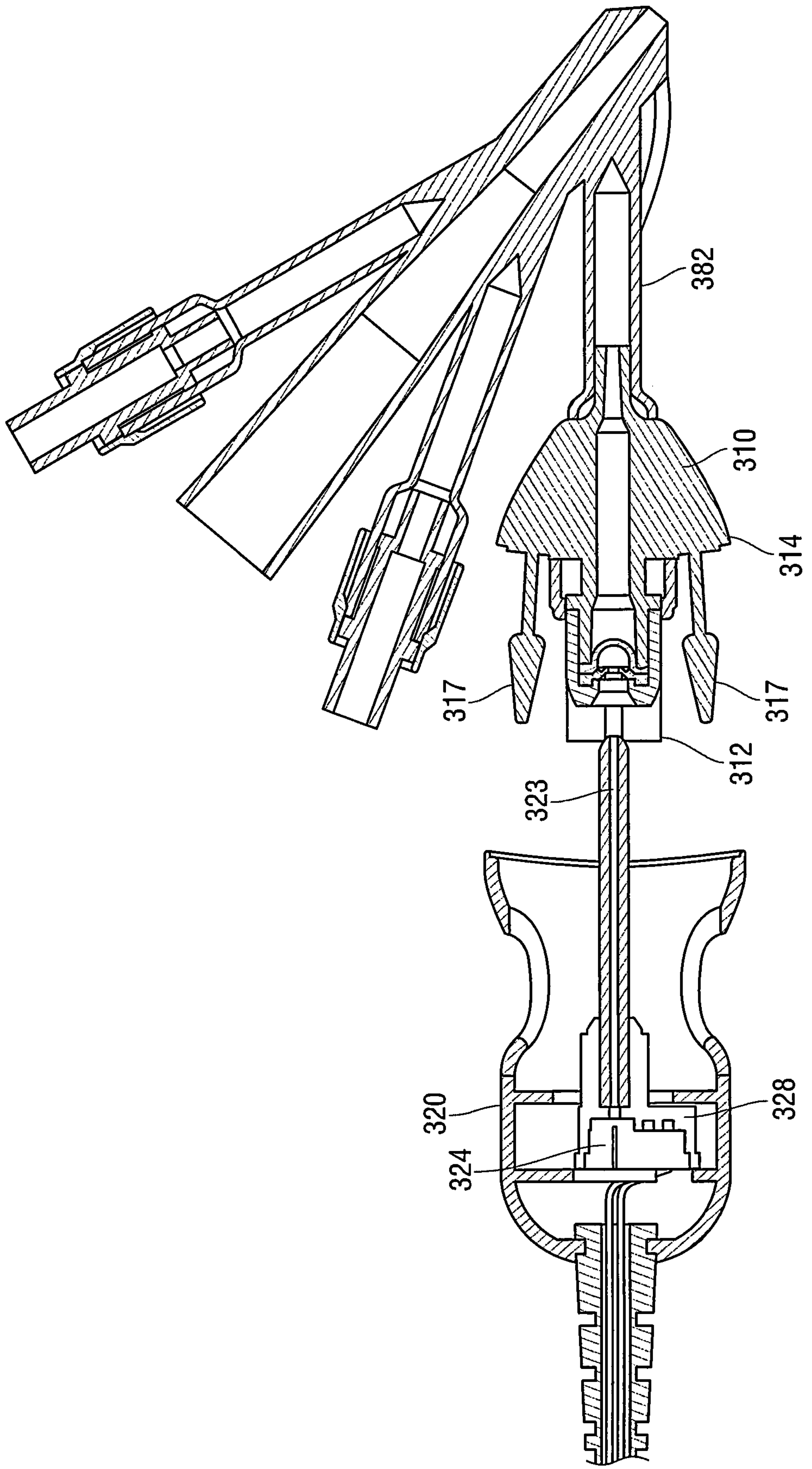
FIG. 29B is a cutaway side view of the hub and connector of FIG. 29A.
Figure 29C:
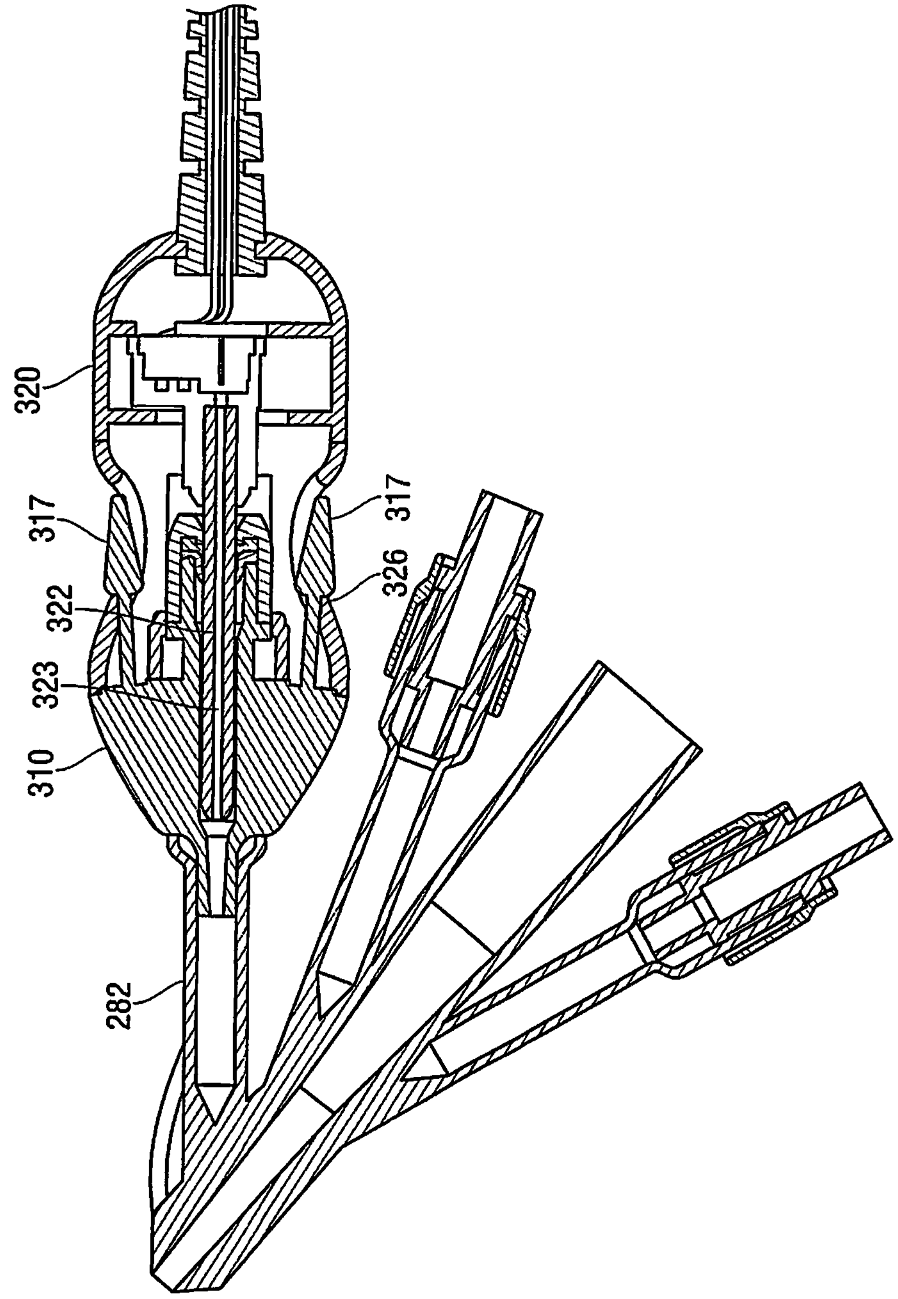
FIG. 29C is a cutaway view similar to FIG. 29B showing the hub attached to the connector of FIG. 29A.

FIGS. 30A-34 illustrate the fully assembled catheter 400 which is used to measure pressure in the same manner as catheter 200 of FIG. 18A. Thus, a transducer hub 430, which can be any of the transducer hubs disclosed herein, such as hub 240 of FIG. 24A, hub 300 of FIG. 28A, etc., is attached to port 420 to advance gas, e.g., air through the lumen to inflate inner balloon 408. The lumens 438, 434 for inflation of the inner balloon 408 and outer balloon 406 are radially spaced from core pin 410 as core pin occupies the drainage lumen 432 (distal of side openings 418) and does not interfere with the balloon inflation lumens 434, 438.

Side opening(s) 418 in catheter 400 communicate with the drainage lumen 432 for draining the bladder. As shown, the drainage opening(s) 418 in this embodiment is positioned between the a) outer balloon 406/inner balloon 408 and b) retention balloon 404. More than one drainage opening can be provided. It should be appreciated that such location of the drainage opening(s) between the retention balloon and pressure balloon(s), rather than distal of the pressure balloon(s) can be utilized with any of the catheter embodiments disclosed herein.

As noted herein, the catheters of the present invention can be utilized for measuring other pressure in a patient and are not limited to intra-abdominal pressure nor limited to measuring bladder pressure.

In the foregoing embodiments, the inner balloon is positioned within the outer balloon (with its outer wall radially spaced from the outer wall of the outer balloon) and deformation of the outer balloon based on changes in pressure within the patient, e.g., within the bladder in response to abdominal pressure, causes deformation of the inner balloon as the fluid within the outer balloon (or wall) exerts a pressure against the wall of the inner balloon. This deforms the inner balloon to provide a pressure reading. In the alternate embodiment of FIGS. 35-41, the inner balloon is positioned within a chamber (or cage). This chamber forms an inner balloon encapsulating member as it encircles/encapsulates the inner balloon and is positioned between the inner balloon and outer balloon. Thus, the encapsulating member (chamber) separates the outer wall of the inner balloon from the interior of the outer balloon. However, the chamber has a series of openings so that the fluid within the outer balloon can pass through the chamber and apply a pressure against the outer wall of the inner balloon to deform the inner balloon to provide pressure readings in the same manner as the other embodiments disclosed herein. As in other outer/inner balloon embodiments, the catheter can be used is a voided cavity, e.g. a voided bladder, since fluid, e.g., water, does not need to be injected since the fluid within the outer balloon acts as a transmission medium.

With reference now to FIGS. 35-41, the catheter 450 has an elongated shaft 451. Note only the distal end of the catheter 450 is shown; the proximal end, hub, connector, etc. being the same as in the foregoing inner and outer balloon embodiments, e.g., catheter 200 of FIG. 18A. The catheter 450 has a retention balloon 454 identical to retention (stabilizing) balloon 206 of catheter 200 (or other stabilizing balloons disclosed herein), an inner balloon 458 and an outer balloon 456. In the gap (space) between the proximal end of the outer balloon 458 and the distal end of the retention balloon 454, is a drainage hole 463 (or multiple drainage holes) for draining the cavity, e.g., the bladder. A thermistor can be placed adjacent the drainage opening 463 for temperature readings, and the thermistor wire can extend through a lumen of the catheter 450, e.g., the drainage lumen, the pressure lumen or a separate lumen, for electrical connection to a temperature monitor. Catheter 450 has three lumens: 1) lumen 486 communicating with outer balloon 456 for inflating outer balloon 456; 2) a lumen communicating with the retention balloon 454 to inflate retention balloon 454; and 3) drainage lumen 484 having one or more side openings 463 at a distal region of the catheter for drainage of the bladder. In this embodiment, the tubular The inner (and outer) balloon can by way of example be made of urethane, although other materials are also contemplated.

The wire connector of the foregoing embodiments can plug into the openings of a connector positioned on or in the hub. The wire connector can be internal of the hub with an opening in the wall of the hub to enable access for the wire connector. Also note that alternatively the wire can include a female connector and the hub can have a male connector. Other types of connectors/connections are also contemplated.

In alternate embodiments, any of the catheters disclosed here can include a pulse oximetry sensor to measure oxygen saturation in the urethral or bladder tissue. The sensor can be located either proximal (see e.g., oxygen sensor 131 of FIG. 13B) or distal to the pressure balloon and/or either proximal (see e.g., oxygen sensor 131 of FIG. 13B) or distal to the stabilizing balloon. It could also alternatively be mounted within one of the balloons.

Figure 14A:
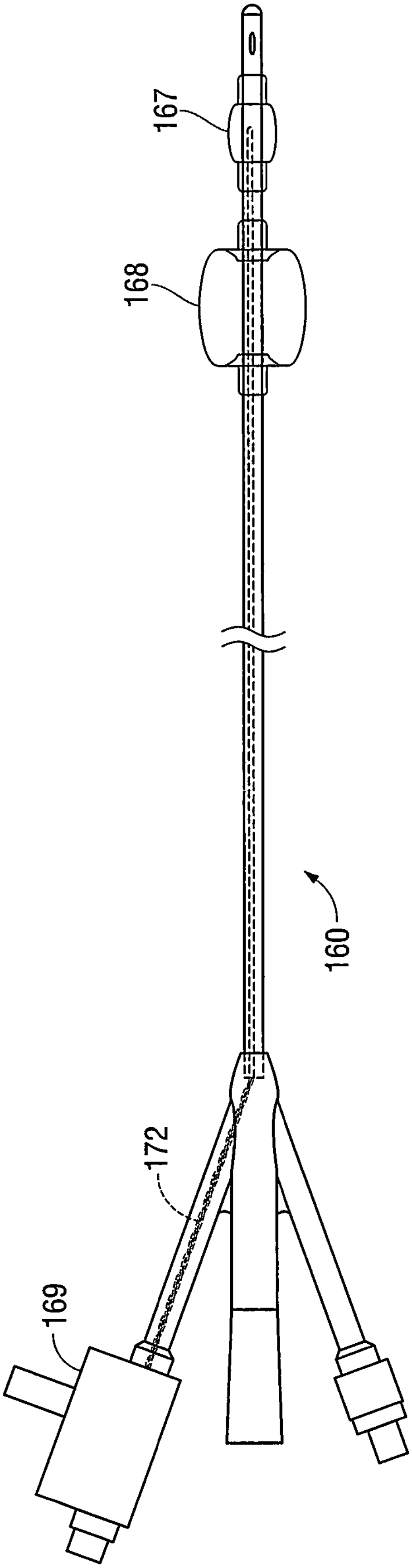
FIG. 14A is a side view of another alternate embodiment of the catheter of the present invention having dual pressure sensors, the first sensor positioned within the air lumen and the second sensor positioned external of the catheter, the two balloons shown in the inflated condition.
Figure 14B:
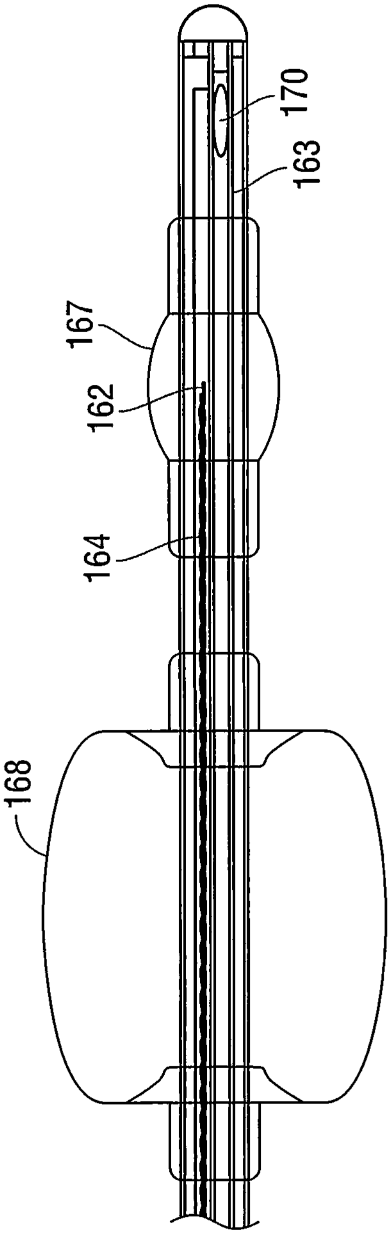
FIG. 14B is an enlarged view of the distal portion of the catheter of FIG. 14A.

It is also contemplated that in some embodiments a backup system be provided to determine pressure. The backup system can provide a double check of pressure readings to enhance accuracy. Such backup system can be used with any of the embodiments disclosed herein to provide a second pressure reading system. One example of such backup system is disclosed in FIGS. 14A and 14B. In this embodiment, catheter 160 has the pressure transducer/pressure sensor 162 like sensor 30 of FIG. 1 within the air (or other gas) lumen 164 communicating with pressure balloon 167, forming a "first system", plus a pressure transducer/pressure sensor 169 at a proximal end of the catheter as in FIG. 12 or external of the catheter forming a "second system". Thus, the pressure sensor 162 is at a distal end of the air charged lumen 164 and pressure sensor 169 is at proximal end of the air charged lumen 164. Both sensors 162 and 169 are electrically connected to a monitor which provides a graphic display of pressure readings. The catheter 160 also includes a temperature sensor either as part of the sensor 162 or a separate component that can be positioned for example in the lumen 164 distal of sensor 162 as in the embodiment of FIG. 8. A stabilizing balloon 168 and an inflation lumen to inflate balloon 168 can also be provided. Lumen 163, having a side opening 170 at its distal end, which can be located distal or proximal of balloon 167, is configured to drain the bladder similar to lumen 20 and side opening 22 of the embodiment of FIG. 1.

In use, catheter 160 is inserted into the bladder and stabilizing balloon 168 is inflated to secure the catheter 160 in place. The system is charged by inflation of the balloon 167, i.e., preferably partially inflated for the reasons discussed above, by insertion of air through side port 172 which is in fluid communication with the air lumen in a closed system formed by the internal space of the balloon 167 and the internal lumen 164 communicating with the internal space of balloon 167. With the balloon 167 inflated, pressure monitoring can commence as external pressure applied to an outer surface of the balloon 167 compresses the air (or other gas) within the chamber. The sensor 162 at the distal end of lumen 64 provides continuous pressure readings, converted to an electrical signal by the transducer within the distal end of lumen, and then electrically communicates through its transmission wires extending through the air lumen to an external monitor either directly or via a converter. Additionally, pressure within the air charged column is measured at a proximal region by sensor 169 within side port 172 of catheter 160. The sensor 162 at the distal end of lumen 164 provides continuous pressure readings, and such pressure readings can be confirmed by the proximal sensor. Such pressure readings can be performed continuously (along with continuous temperature monitoring) or alternatively can also be adapted if desired for periodic monitoring so the pressure and/or temperature readings can be taken at intervals or on demand by the clinician. Thus, air pressure readings at a proximal end plus microtip pressure readings at the distal end are provided. The sensors 162 and 169 can electrically communicate with an external monitor to display both pressure readings from sensors 162, 169, or alternatively, if the pressure readings are different, they can be averaged to display a single measurement. Clearly, other displays of information can be provided to display the information from the two sensors 162, 169.

The sensors disclosed herein can be microtip sensors within the air (or other gas) lumen or balloon. In alternative embodiments, fiber optic sensors within the air (or other gas) lumen or balloon can by utilized to transmit circumferential/area pressure. The pressure transducers can be housed within the catheter or alternatively external to the catheter. Additionally, core temperature sensors can be part of the pressure sensor or a separate axially spaced component.

The multi-lumen or single lumen catheters disclosed herein provide an air (or other gas) charged balloon (air containing chamber) giving precise readings of intra-abdominal pressure (or for other pressure measurements) and the systems are charged via insertion of air through a side port. The multi-lumen catheters are easily inserted into the bladder in the same manner as standard bladder drainage catheters and enable continuous drainage of urine while continuously recording IAP without interrupting urine flow and without requiring retrograde filling of the bladder with water. Thus, these catheters provide a closed system. The catheters also have a balloon providing a large reservoir (large capacity) and large circumferential area/interface for obtaining more information from the bladder over multiple reference points (rather than a single point sensor) that provides an average pressure to provide a more accurate assessment of the surrounding environment as pressure measurement is not limited to one side of the bladder but can determine measurements on the opposing side as well. The balloon can have a sufficiently large circumferential area so that it is in contact with the bladder wall, and in some embodiments, could distend the bladder wall, thus enabling pressure measurement without insertion of fluid into the bladder. When used in other body cavities for other pressure measurements, the pressure balloon of the multi-lumen or single lumen catheters disclosed herein can be of sufficiently large to contact or in some embodiments, distend the cavity wall, thus enabling pressure measurement without insertion of fluid into the cavity. The balloon, as noted above, of the multi-lumen or single lumen catheters disclosed herein can be impermeable or have an impermeable membrane (as defined herein) to prevent escape of gas to prevent loss of accurate pressure readings.

As noted above the catheters in some embodiments can be connected to a bedside monitor through either a wire or blue-tooth wireless connection. The system can also in some embodiments include an indicator or alarm system to alert the staff at the site as well as remote staff through wired or wireless connections to external apparatus, e.g., hand held phones or remote monitors.

As noted above, an alarm or indicator can be provided in some embodiments to alert the staff. The indicator can be a visual indicator such as a light, LED, color change, etc. Alternatively, or additionally, the indicator can be an audible indicator which emits some type of sound or alarm to alert the staff. The indicator can be at the proximal region of the catheter or at other portions of the catheter, e.g., at a distal end portion, where known imaging techniques would enable the user to discern when the indicator is turned on. It is also contemplated that in addition to providing an alert to the user in some embodiments, the pressure monitoring system can be tied into a system to directly reduce abdominal pressure so that if the pressure exceeds a threshold level (value), the abdominal pressure can automatically be reduced. In such systems, an indicator can be provided on the proximal portion of the catheter, e.g., at a proximal end outside the patient's body, or separate from the catheter. The sensor can be in communication with the indicator, either via connecting wires extending through a lumen of the catheter or a wireless connection. The sensor can be part of a system that includes a comparator so that a comparison of the measured pressure to a predetermined threshold pressure value is performed and a signal is sent to the indicator to activate (actuate) the indicator if the measured pressure exceeds the threshold pressure to alert the clinician or staff that pressure within the abdomen is too high and a signal is also sent to a device or system to automatically actuate the device or system to reduce the abdominal pressure. If the measured temperature is below the threshold, the indicator is not activated. A similar system can be used for temperature measurement and indication.

It is also contemplated that a micro-air charged sensor could be provided in the retention (stabilizing) balloon.

It is also contemplated that microtip sensors and/or fiber optic sensors can be utilized to measure pressure, and these sensors can be utilized instead of or in addition to the air pressure readings utilizing the aforedescribed balloon(s) for measuring pressure.

Pulse oximeters for measuring oxygen levels (oxygen saturation) in the urethral and/or bladder tissue could also be provided. In some embodiments, the pulse oximetry sensors can be positioned on the catheter proximal to the retention balloon. Alternatively, the sensors can be positioned within the retention balloon, on the catheter distal to the pressure balloon or on other regions of the catheter. Another channel in the catheter can be provided for the sensor and its connector to external devices, e.g. readers.

The catheters disclosed herein are designed for insertion into the bladder. However, it is also contemplated that they can be adapted for insertion into the rectum, colostomy pouch, stomach, supra-pubic bladder drain, or other orifice directly connected with the abdominal cavity. They can also be inserted into other areas connected with other cavities. Uses include by way of example, cardiac use, labor and delivery use, rectal placement for abdominal cavity, use for gastric pressure, esophageal motility, endocranial pressures ERCP, gall bladder, etc.

Although the apparatus and methods of the subject invention have been described with respect to preferred embodiments, those skilled in the art will readily appreciate that changes and modifications may be made thereto without departing from the spirit and scope of the present invention as defined by the appended claims.

The invention claimed is:

1. A catheter insertable into a patient comprising:
- a first lumen;
- a second lumen independent of the first lumen;
- an expandable pressure balloon in fluid communication the second lumen;
- a pressure sensor positioned within the pressure balloon for measuring pressure within a bladder of the patient;
- an expandable stabilizing balloon positioned proximal of a distalmost end of the catheter and proximal of the pressure balloon, the stabilizing balloon communicating with the first lumen for expansion from a first configuration to a second expanded configuration to stabilize a position of the catheter, the stabilizing balloon expanding radially outwardly with respect to the catheter; and
- an oxygen sensor measuring oxygen levels in urethral tissue, wherein an entirety of the oxygen sensor is positioned proximal of the stabilizing balloon and the expandable pressure balloon and adapted for positioning in a urethra of the patient.

2. The catheter of claim 1, further comprising a drainage lumen drainage of the bladder, the drainage lumen independent of the first lumen.

3. The catheter of claim 2, further comprising a side opening in a wall of the catheter in communication with the drainage lumen, the side opening positioned distal of the stabilizing balloon and distal of the oxygen sensor.

4. The catheter of claim 1, wherein the catheter includes a temperature sensor positioned within another lumen of the catheter to measure core body temperature.

5. The catheter of claim 1, wherein the catheter is configured for insertion into the bladder.

6. The catheter of claim 1, further comprising a drainage lumen and a side opening in a wall of the catheter communicating with the drainage lumen.

7. A catheter insertable into a patient comprising:
- a first lumen;
- first pressure balloon positioned at a distal region of the catheter, the first balloon communicating with the first lumen for expansion from a first configuration to a second expanded configuration, the balloon expanding radially outwardly with respect to the catheter,
- a pressure sensor positioned within the first balloon, wherein pressure is measured based on compression of gas caused by deformation of the expanded balloon; and
- an oxygen sensor measuring oxygen levels in urethral tissue, wherein an entirety of the oxygen sensor is positioned proximal of the pressure balloon and adapted for positioning in a urethra of the patient.

8. The catheter of claim 7, further comprising a drainage lumen communicating with a body cavity to remove fluid from the body cavity, the drainage lumen independent of the first lumen.

9. The catheter of claim 7, wherein the catheter includes a temperature sensor positioned within another lumen of the catheter to measure core body temperature.

10. The catheter of claim 7, wherein the catheter is configured for insertion into a bladder of the patient.

11. The catheter of claim 9, further comprising a drainage lumen and a side opening in a wall of the catheter communicating with the drainage lumen.

12. The catheter of claim 1, wherein the pressure balloon is partially inflated during use.

13. The catheter of claim 7, wherein pressure balloon is partially inflated during use.

14. The catheter of claim 1, wherein the stabilizing balloon has a greater cross-sectional dimension than the pressure balloon.

15. The catheter of claim 14, wherein the pressure balloon has a different configuration than the stabilizing balloon.

16. The catheter of claim 1, wherein the pressure as a different configuration than the stabilizing balloon.

17. The catheter of claim 11, wherein the oxygen sensor is positioned proximal of the side opening.

* * * * *